United States Patent
Bornhoft et al.

(10) Patent No.: US 11,389,178 B2
(45) Date of Patent: Jul. 19, 2022

(54) BONE AND TISSUE RESECTION DEVICES AND METHODS

(71) Applicant: Medos International Sàrl, Le Locle (CH)

(72) Inventors: Stephen Bornhoft, Raynham, MA (US); John C. Voellmicke, Franklin, MA (US); Eric Buehlmann, Duxbury, MA (US); Roman Lomeli, Plymouth, MA (US); Thomas Gamache, Westport, MA (US); Katherine Selover, Westport, MA (US); Duane Jeffrey Enck, West Palm Beach, FL (US)

(73) Assignee: Medos International Sarl, Le Locle (CH)

( * ) Notice: Subject to any disclaimer, the term of this patent is extended or adjusted under 35 U.S.C. 154(b) by 211 days.

(21) Appl. No.: 16/390,995

(22) Filed: Apr. 22, 2019

(65) Prior Publication Data

US 2020/0330106 A1     Oct. 22, 2020

(51) Int. Cl.
*A61B 17/16* (2006.01)
*A61B 17/00* (2006.01)

(52) U.S. Cl.
CPC ...... *A61B 17/1611* (2013.01); *A61B 17/1628* (2013.01); *A61B 17/1637* (2013.01); *A61B 2017/00402* (2013.01); *A61B 2017/00407* (2013.01); *A61B 2017/00539* (2013.01); *A61B 2017/00544* (2013.01)

(58) Field of Classification Search
CPC ............ A61B 17/1604; A61B 17/1608; A61B 17/1611; A61B 17/1628; A61B 17/32002; A61B 2017/320024; A61B 2017/320028
See application file for complete search history.

(56) References Cited

U.S. PATENT DOCUMENTS

| | | |
|---|---|---|
| 2,435,863 A | 2/1948 | Wydro |
| 3,829,925 A | 8/1974 | Kirkland et al. |
| 3,978,862 A | 9/1976 | Morrison |
| 4,598,710 A | 7/1986 | Kleinberg et al. |
| 4,844,088 A | 7/1989 | Kambin |
| 4,923,441 A | 5/1990 | Shuler |

(Continued)

FOREIGN PATENT DOCUMENTS

WO     2017/160940 A1     9/2017

OTHER PUBLICATIONS

International Search Report and Written Opinion for Application No. PCT/IB2020/053772, dated Jul. 15, 2020 (14 pages).

(Continued)

*Primary Examiner* — Matthew J Lawson

(74) *Attorney, Agent, or Firm* — Barnes & Thornburg LLP

(57) ABSTRACT

Embodiments of bone and tissue resection devices are disclosed herein. In one embodiment, a device can include a blade having a distal cutting edge configured to perform a cutting action that produces a plug or core from a media being cut by the cutting edge, a drive mechanism arranged to transfer an oscillating force to the cutting edge for oscillating the cutting edge, a shield positioned to block contact with a portion of the cutting edge, and a depth adjustment mechanism configured to translate the cutting edge along a proximal-distal axis of the shield to adjust an axial position of the cutting edge relative to the shield.

29 Claims, 42 Drawing Sheets

(56) References Cited

U.S. PATENT DOCUMENTS

| | | |
|---|---|---|
| 5,201,731 A | 4/1993 | Hakky |
| 5,201,749 A | 4/1993 | Sachse et al. |
| 5,451,227 A | 9/1995 | Michaelson |
| 5,709,698 A | 1/1998 | Adams et al. |
| 5,873,866 A | 2/1999 | Kondo et al. |
| 5,879,365 A | 3/1999 | Whitfield et al. |
| 5,980,528 A | 11/1999 | Salys |
| 6,224,617 B1 | 5/2001 | Saadat et al. |
| 8,080,011 B2 | 12/2011 | Harp |
| 8,241,290 B2 | 8/2012 | Michelson |
| 8,292,909 B1 | 10/2012 | DuBois et al. |
| 8,323,302 B2 | 12/2012 | Robertson et al. |
| 8,529,593 B2 | 9/2013 | Berberich |
| 8,531,064 B2 | 9/2013 | Robertson et al. |
| 8,574,167 B2 | 11/2013 | Smith et al. |
| 8,702,702 B1 | 4/2014 | Edwards et al. |
| 8,814,871 B2 | 8/2014 | Mansmann |
| 9,095,366 B2 | 8/2015 | Sullivan et al. |
| 9,226,792 B2 | 1/2016 | Bloom |
| 9,232,937 B2 | 1/2016 | Alleyne |
| 9,532,796 B2 | 1/2017 | Dubois et al. |
| 9,636,132 B2 | 5/2017 | Nguyen et al. |
| 9,655,640 B2 | 5/2017 | Hedstrom et al. |
| 9,681,913 B2 | 6/2017 | Orczy-Timko et al. |
| 9,687,254 B2 | 6/2017 | Shadeck et al. |
| 9,962,170 B2 | 5/2018 | Jansen et al. |
| 9,968,371 B2 | 5/2018 | Todd |
| 10,022,140 B2 | 7/2018 | Germain et al. |
| 10,117,667 B2 | 11/2018 | Robertson et al. |
| 10,179,002 B2 | 1/2019 | Wasicek et al. |
| 2001/0029372 A1 | 10/2001 | Quick |
| 2004/0102783 A1 | 5/2004 | Sutterlin et al. |
| 2004/0147934 A1* | 7/2004 | Kiester ............ A61B 17/32002 606/80 |
| 2005/0283175 A1 | 12/2005 | Tanner et al. |
| 2006/0155210 A1 | 7/2006 | Beckman et al. |
| 2007/0162062 A1 | 7/2007 | Norton et al. |
| 2007/0265633 A1 | 11/2007 | Moon et al. |
| 2008/0103504 A1 | 5/2008 | Schmitz et al. |
| 2008/0188878 A1 | 8/2008 | Young |
| 2011/0106088 A1 | 5/2011 | Raus |
| 2011/0190773 A1 | 8/2011 | Michelson |
| 2013/0046316 A1* | 2/2013 | Sullivan .................. A61B 10/04 606/115 |
| 2013/0072935 A1 | 3/2013 | Matsuda et al. |
| 2013/0103067 A1 | 4/2013 | Fabro et al. |
| 2014/0121656 A1 | 5/2014 | McKay |
| 2014/0276848 A1* | 9/2014 | Leguidleguid ..... A61B 17/1671 606/83 |
| 2015/0127013 A1 | 5/2015 | Mani et al. |
| 2015/0157228 A1 | 6/2015 | Marino et al. |
| 2015/0289887 A1* | 10/2015 | Pedicini ............. A61B 17/1628 606/80 |
| 2016/0206328 A1 | 7/2016 | Lo et al. |
| 2016/0206342 A1 | 7/2016 | Robertson et al. |
| 2016/0235469 A1 | 8/2016 | Prisco et al. |
| 2016/0262785 A1 | 9/2016 | Dubois et al. |
| 2016/0296247 A1 | 10/2016 | Walen |
| 2017/0172586 A1 | 6/2017 | Wallace et al. |
| 2017/0258519 A1 | 9/2017 | Germain et al. |
| 2017/0265881 A1 | 9/2017 | O'Neil et al. |
| 2018/0214162 A1 | 8/2018 | King et al. |
| 2018/0360495 A1 | 12/2018 | Adams et al. |
| 2019/0021765 A1* | 1/2019 | Magno ............. A61B 17/32002 |
| 2019/0117249 A1 | 4/2019 | Bono et al. |
| 2020/0170660 A1* | 6/2020 | Bono ............... A61B 17/32002 |
| 2020/0268401 A1 | 8/2020 | Edwards et al. |
| 2020/0268402 A1* | 8/2020 | Edwards .......... A61B 17/32002 |
| 2020/0268404 A1 | 8/2020 | Collinson et al. |
| 2020/0275944 A1* | 9/2020 | Goldberg ........... A61B 17/1659 |
| 2020/0330105 A1 | 10/2020 | Bornhoft |
| 2020/0330115 A1 | 10/2020 | Bornhoft et al. |
| 2020/0330116 A1 | 10/2020 | Bornhoft et al. |
| 2021/0153931 A1* | 5/2021 | Germain ............ A61B 18/1492 |

OTHER PUBLICATIONS

U.S. Appl. No. 16/391,002, filed Apr. 22, 2019, Bone and Tissue Resection Devices and Methods.
U.S. Appl. No. 16/391,004, filed Apr. 22, 2019, Bone and Tissue Resection Devices and Methods.
U.S. Appl. No. 16/391,005, filed Apr. 22, 2019, Bone and Tissue Resection Devices and Methods.

* cited by examiner

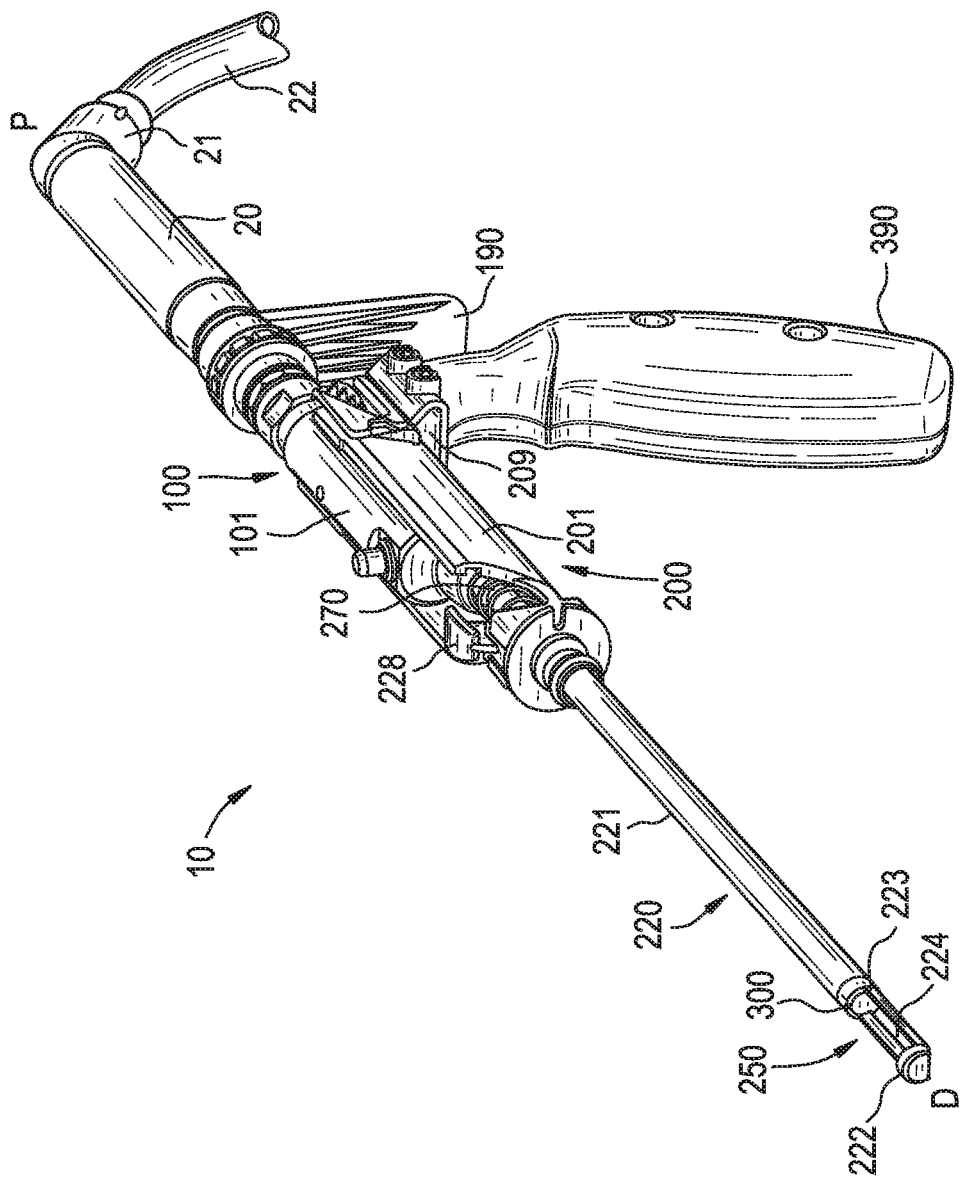

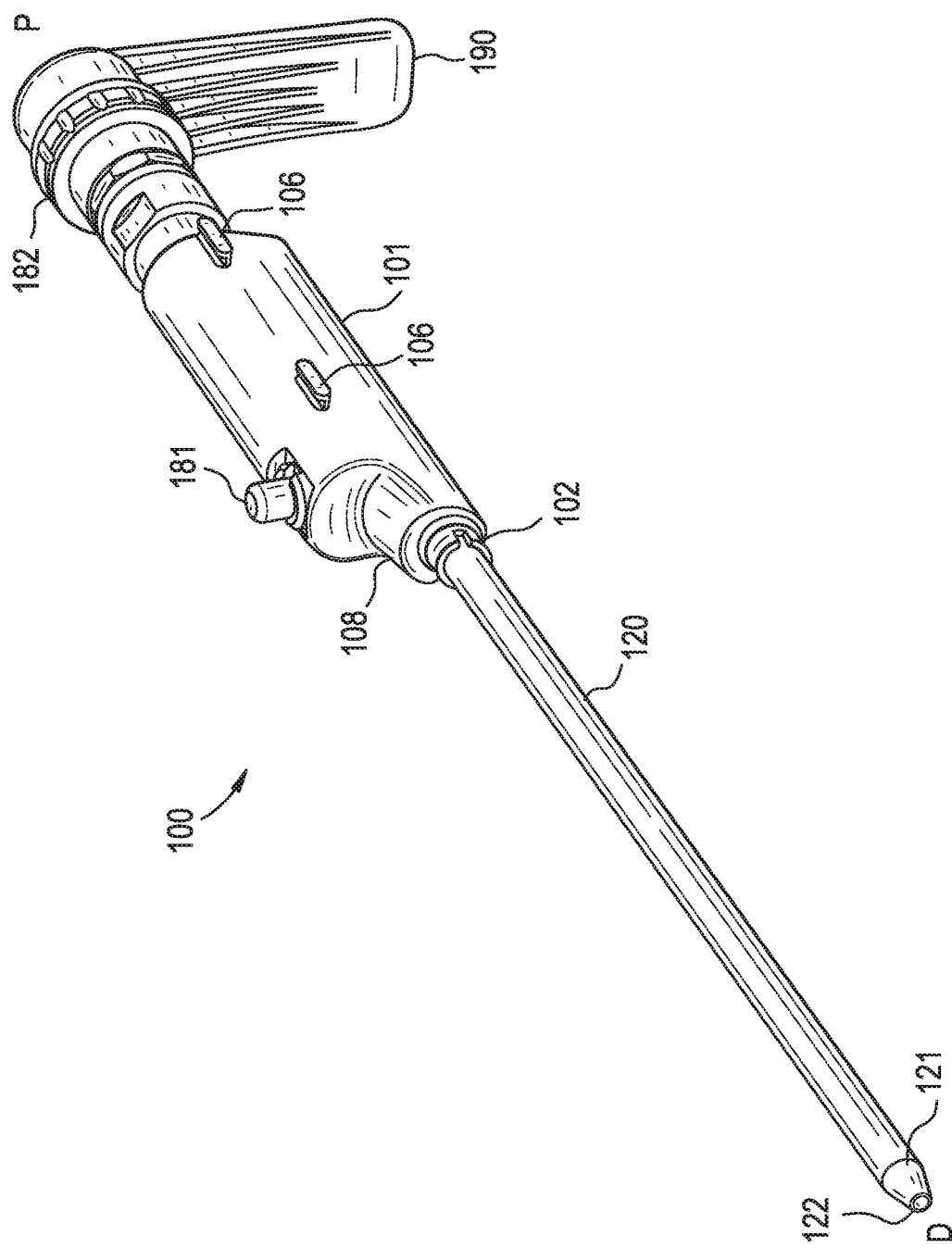

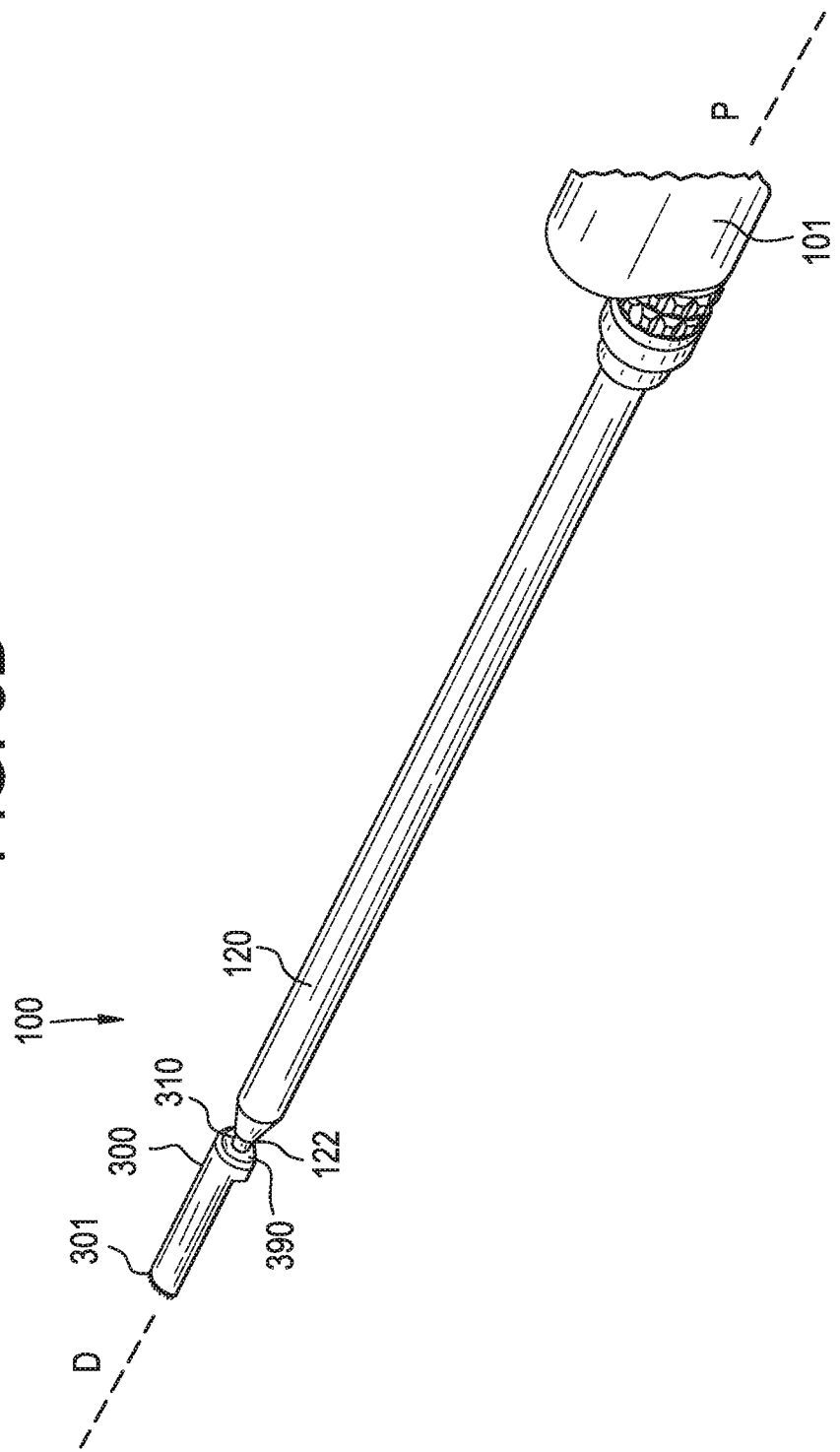

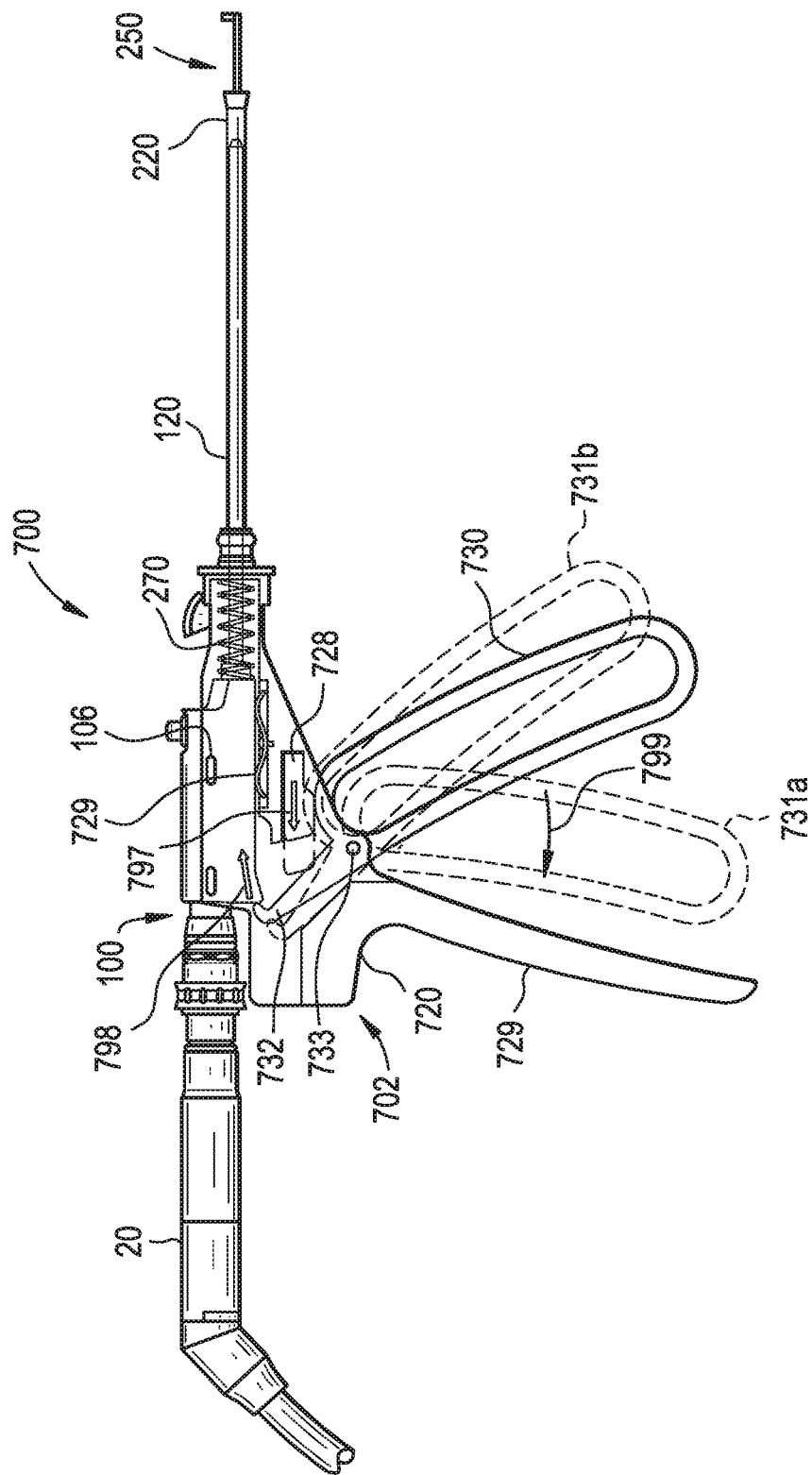

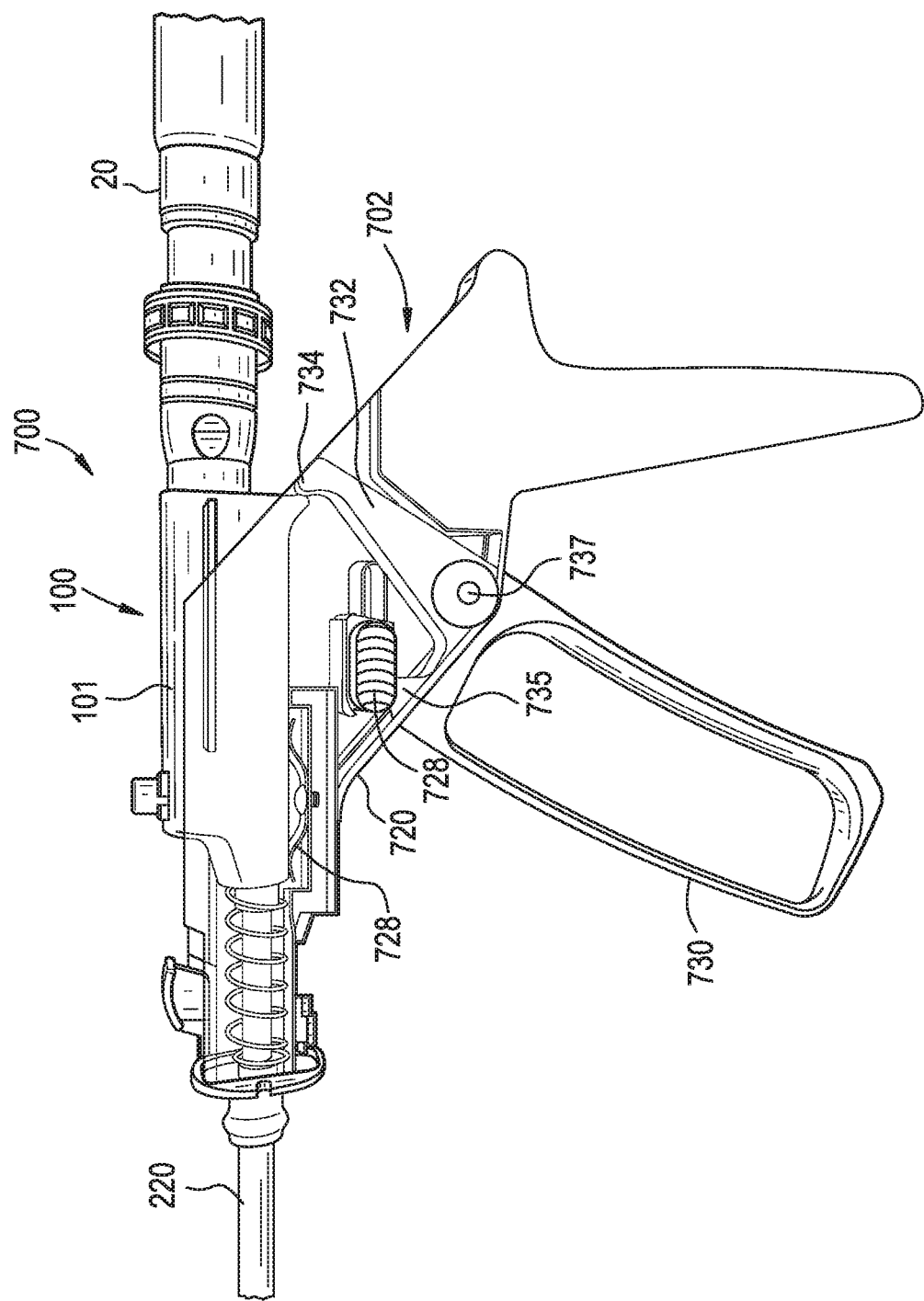

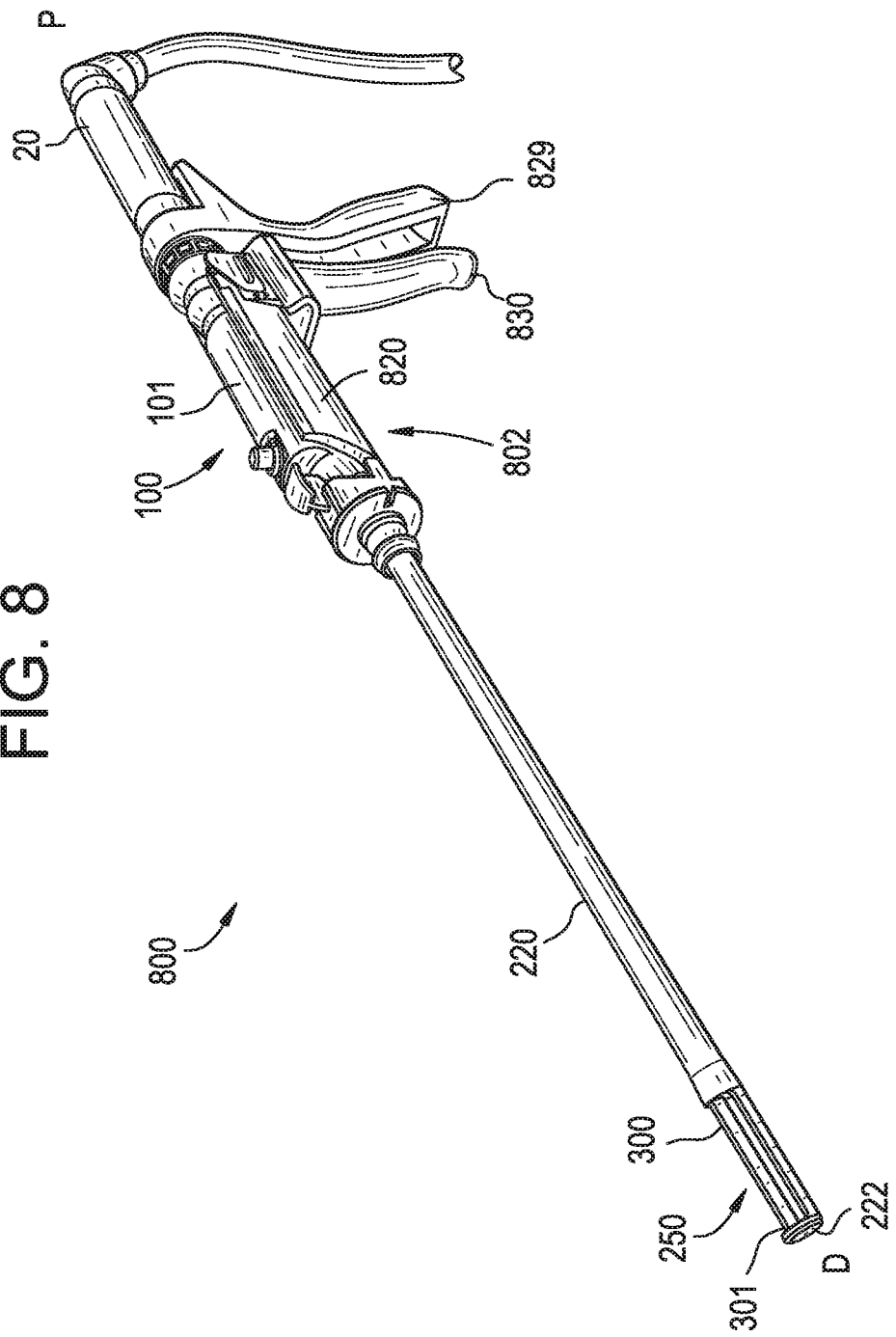

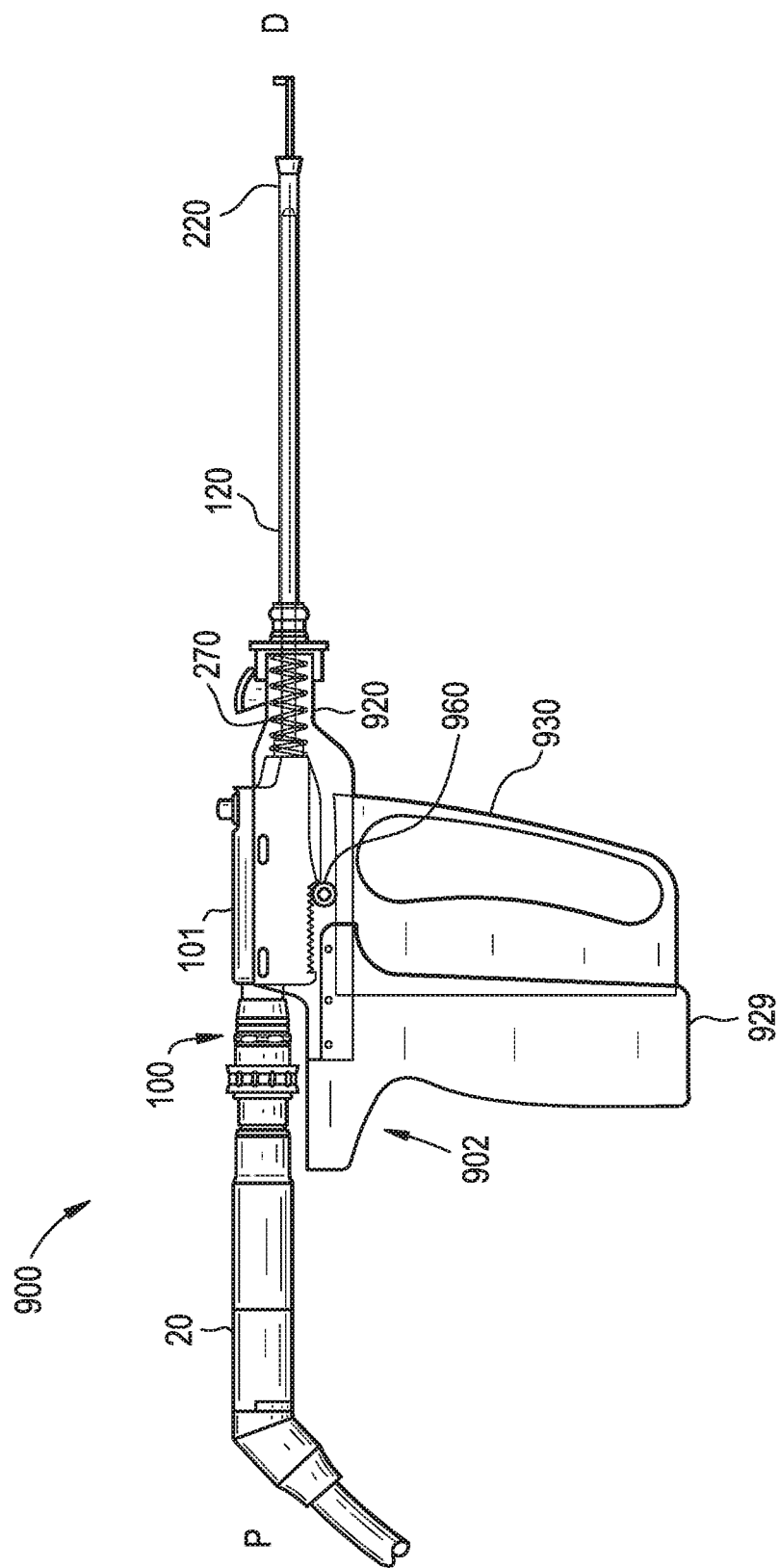

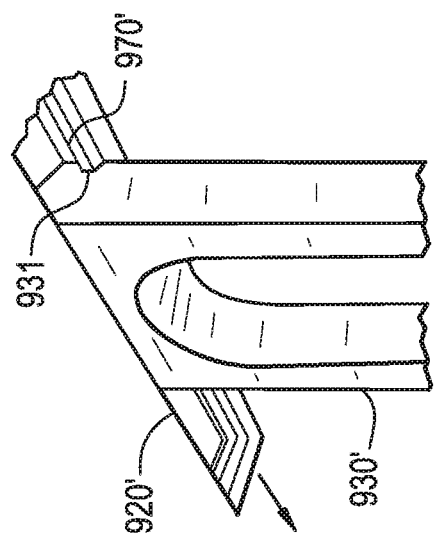
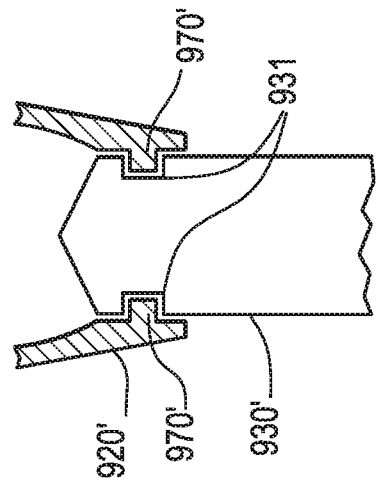
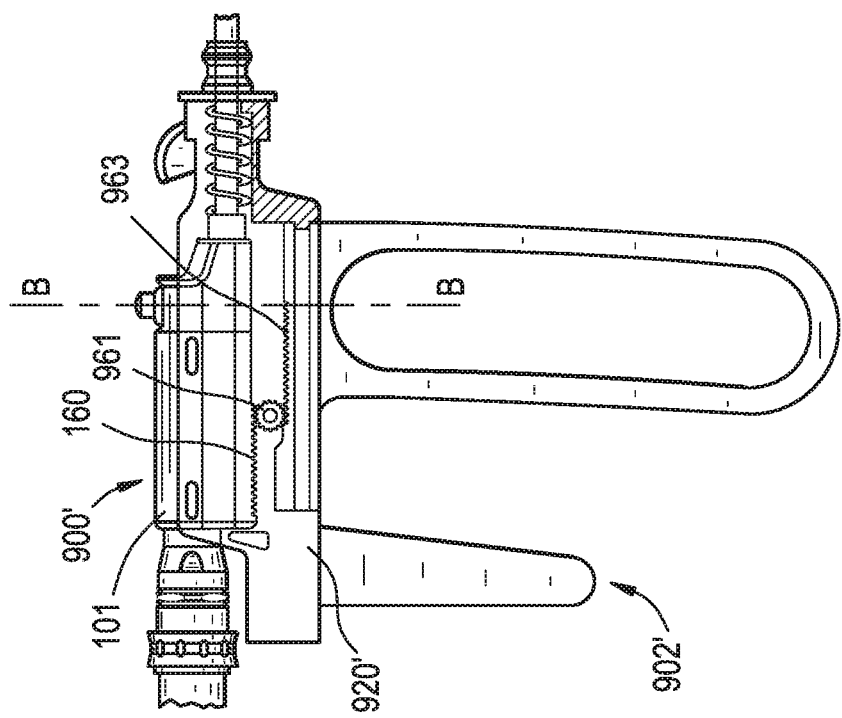

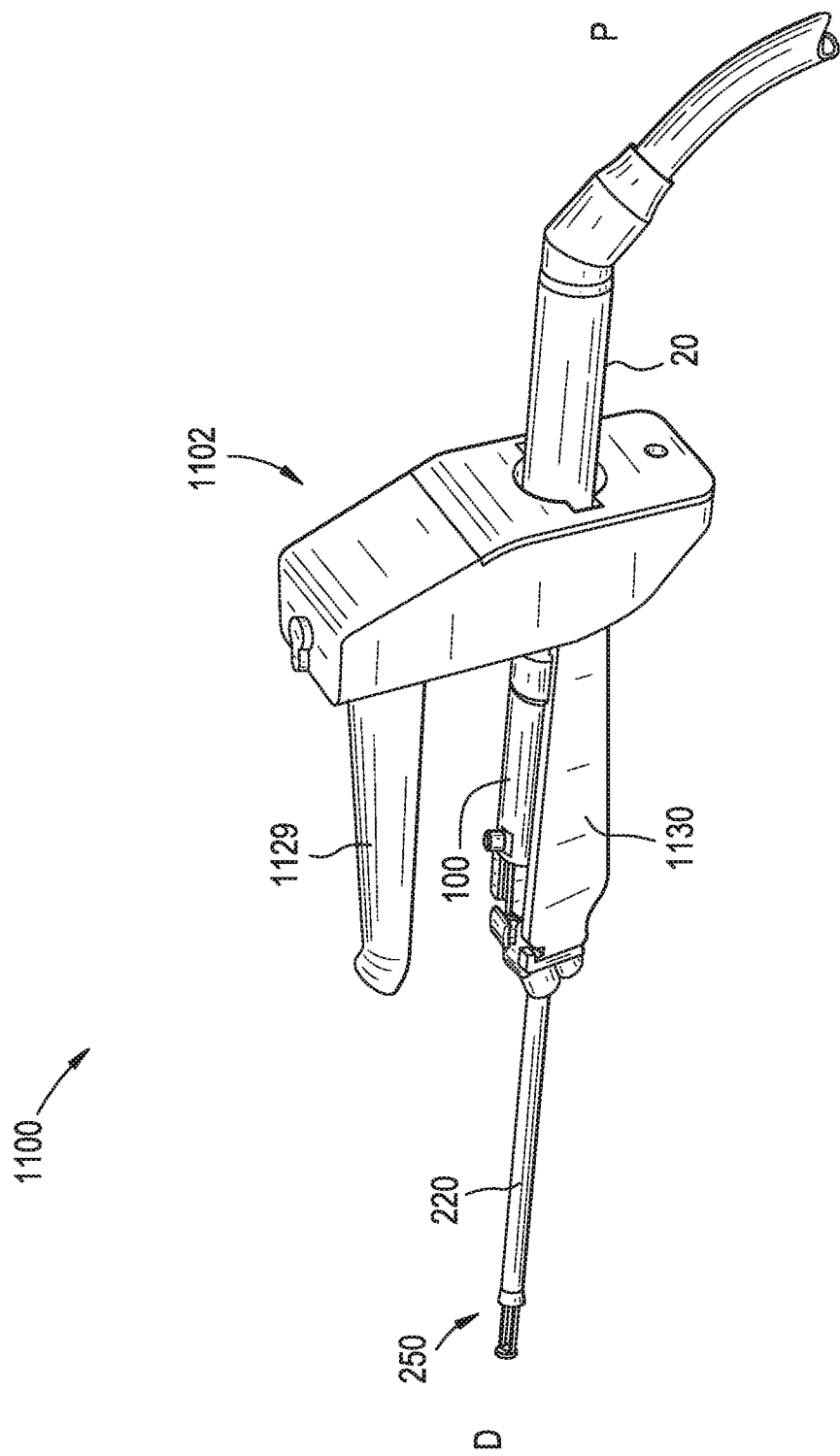

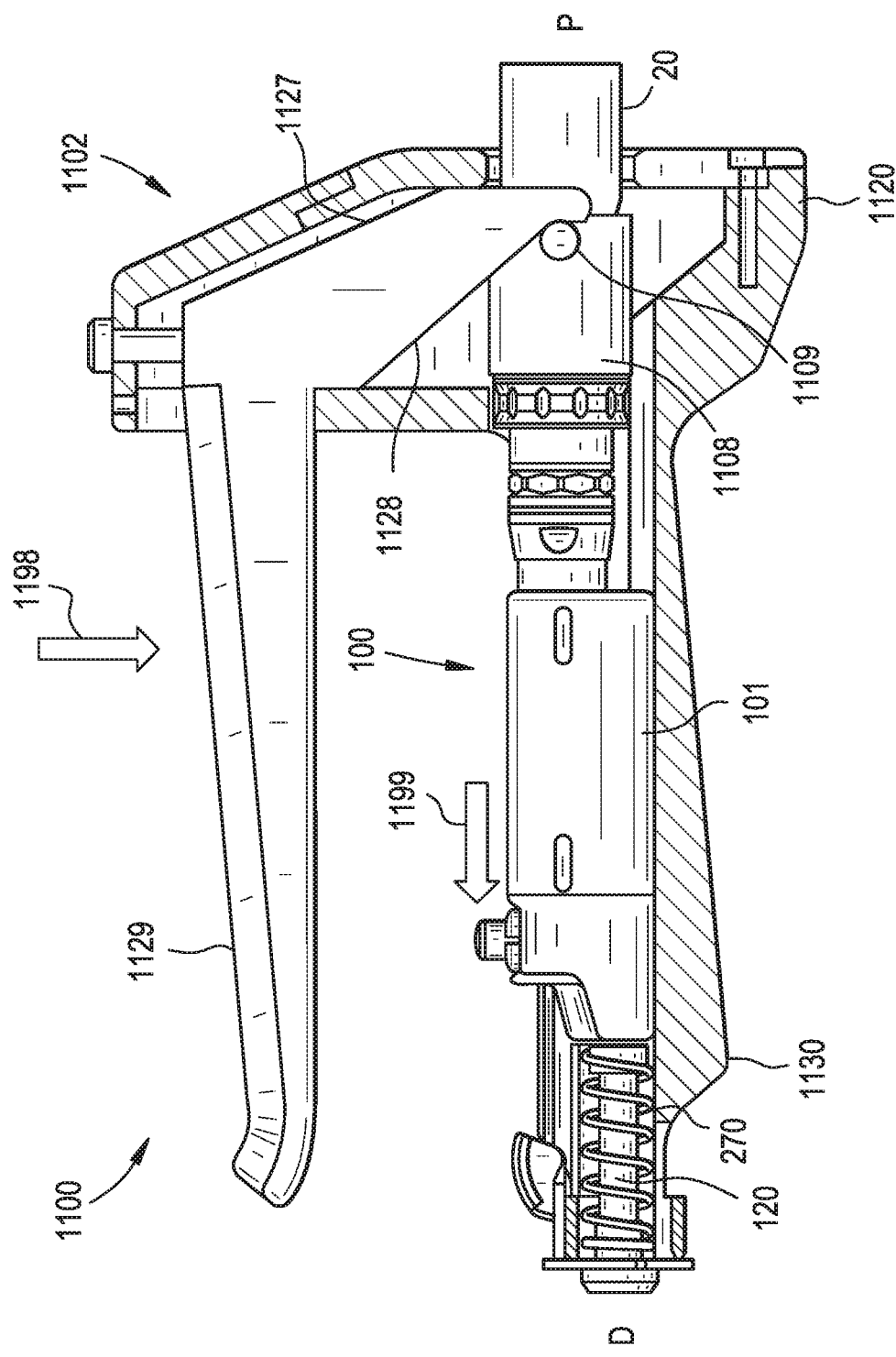

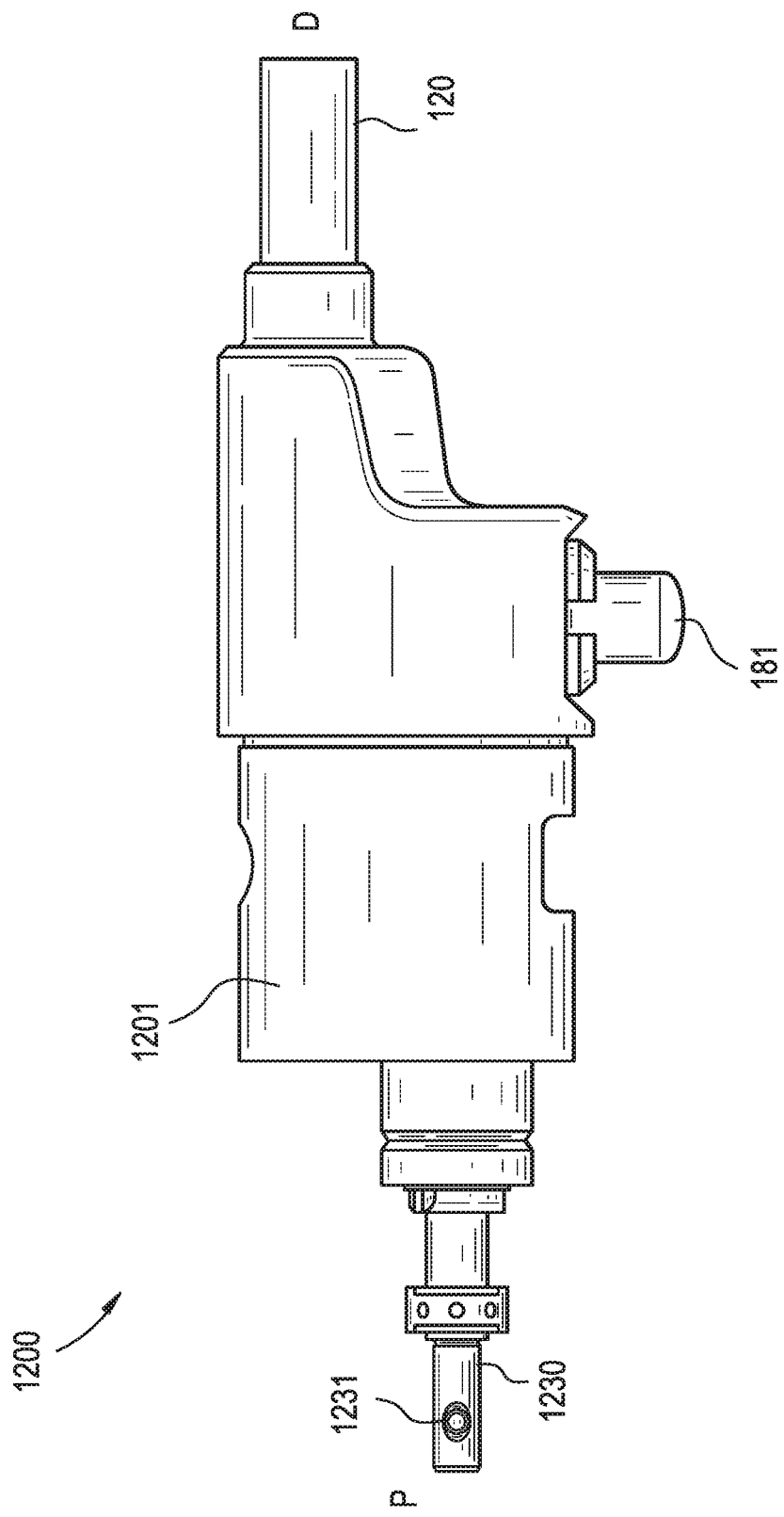

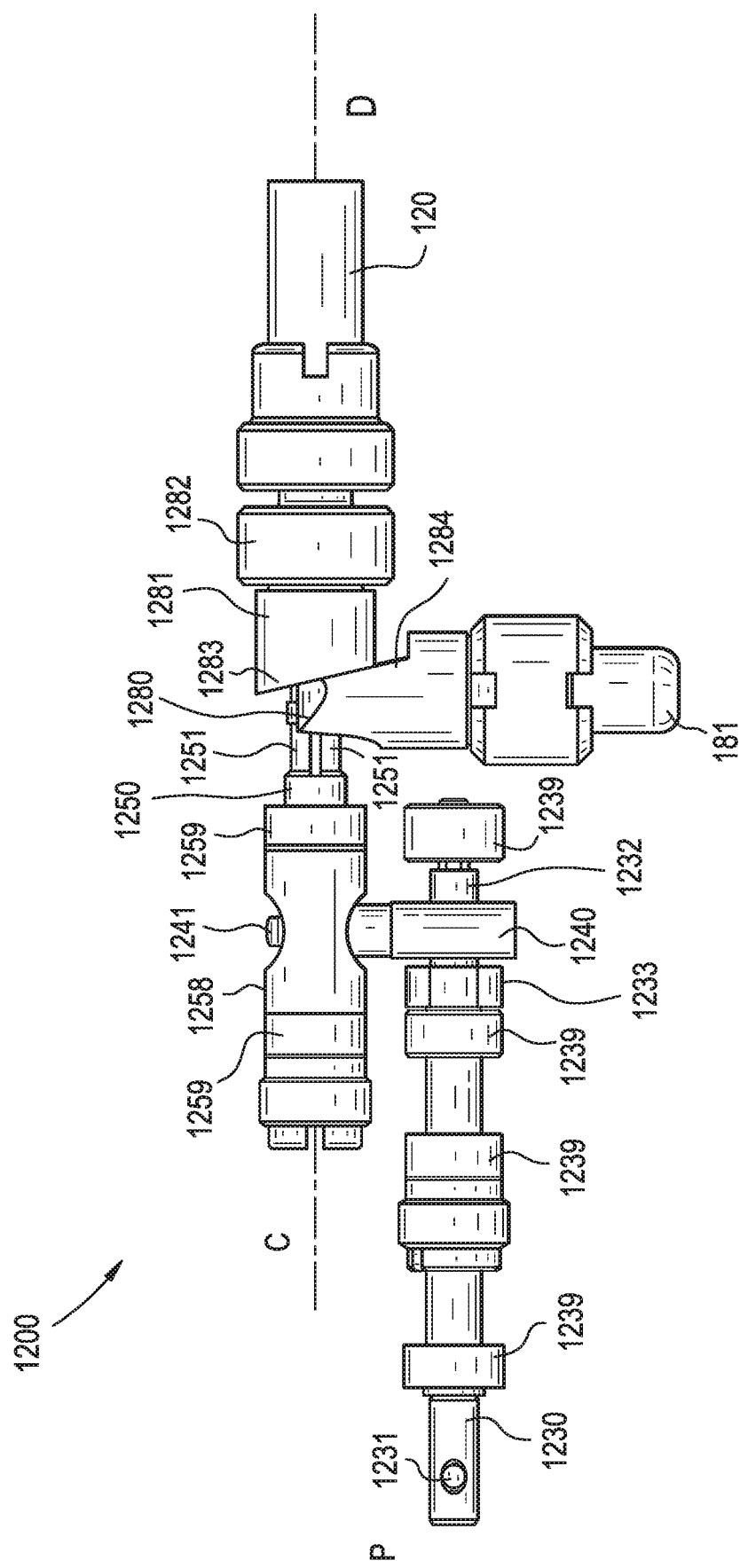

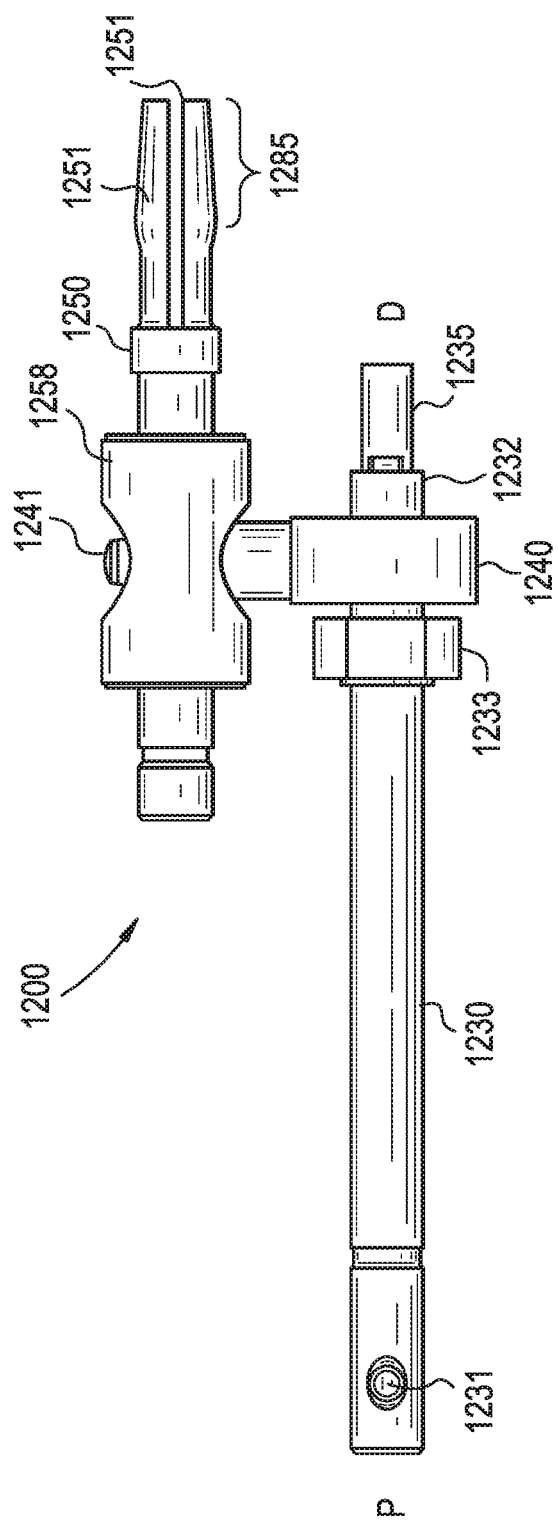

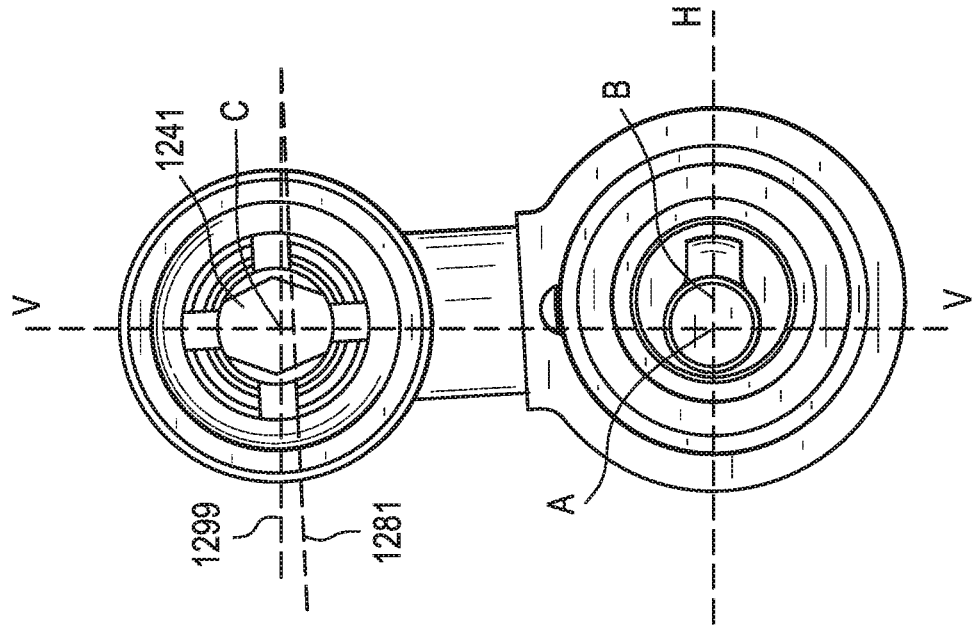
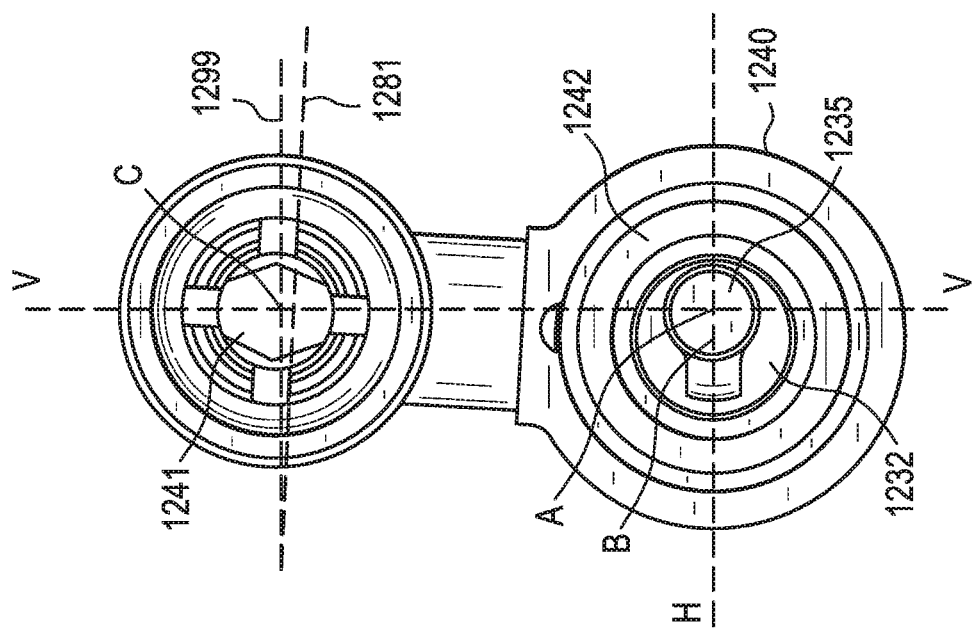

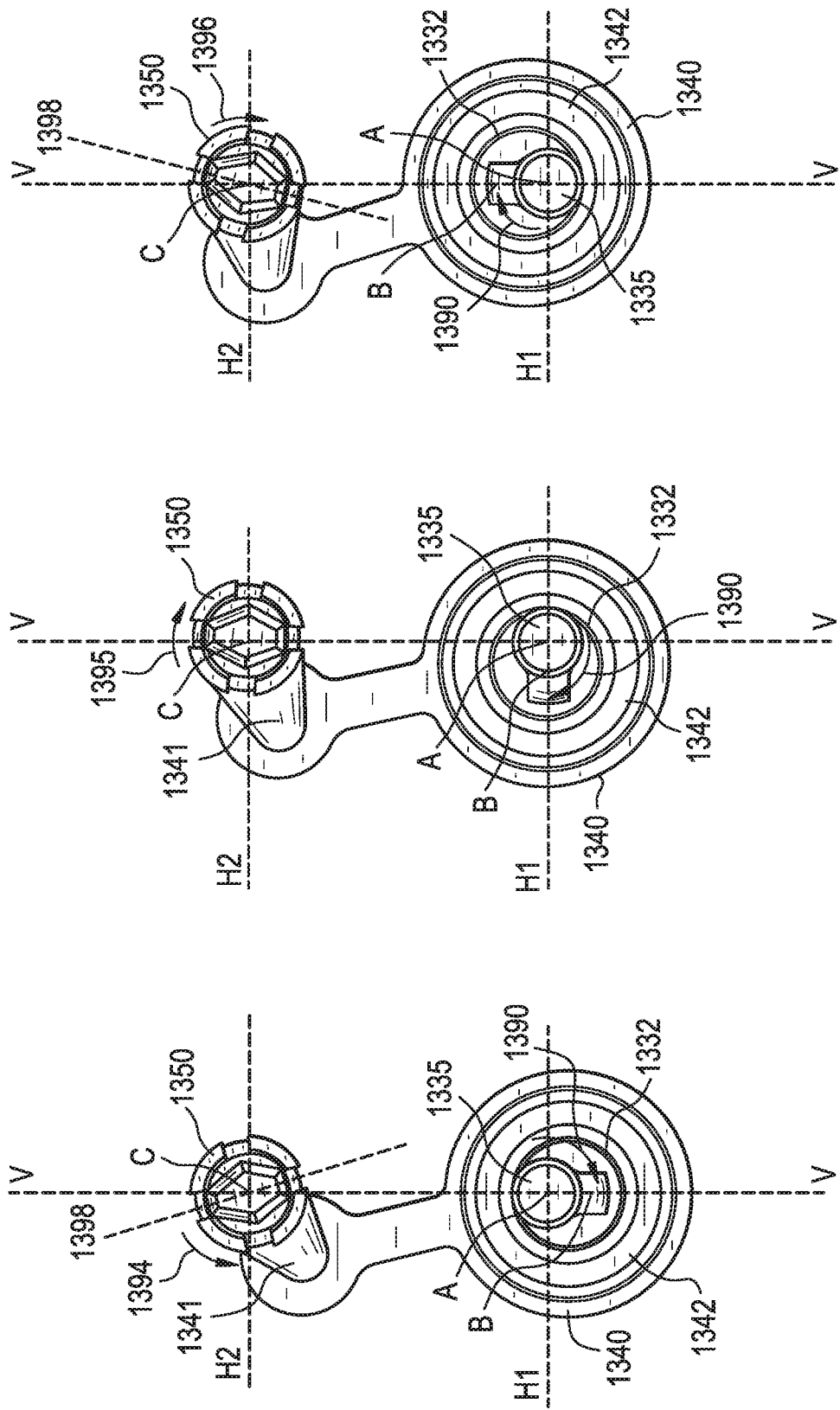

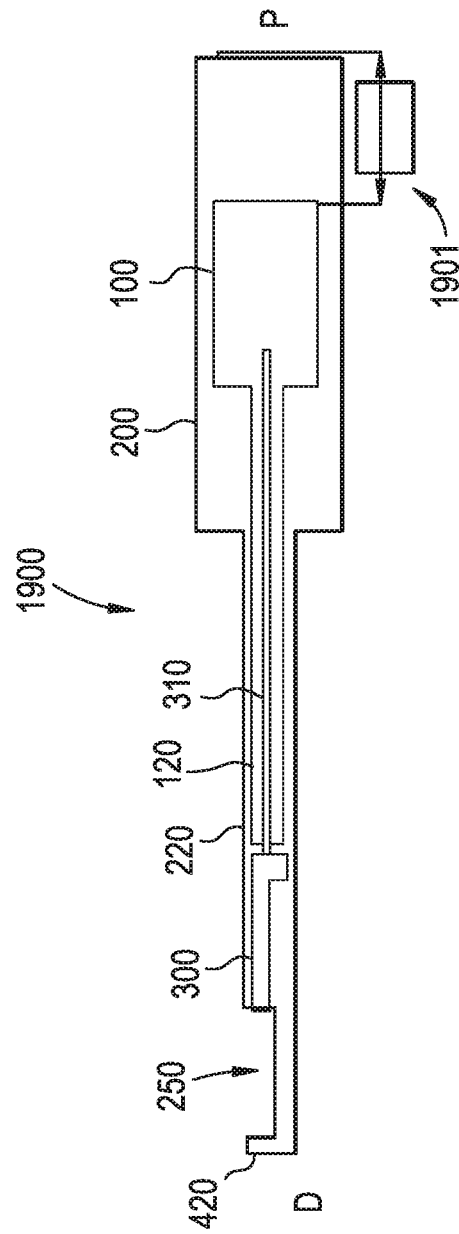
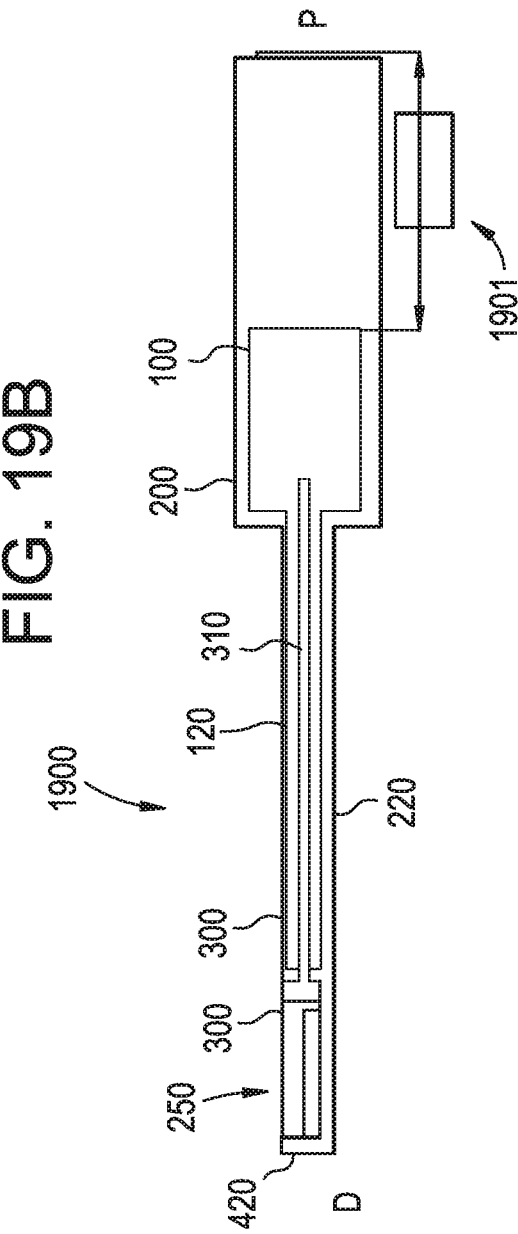

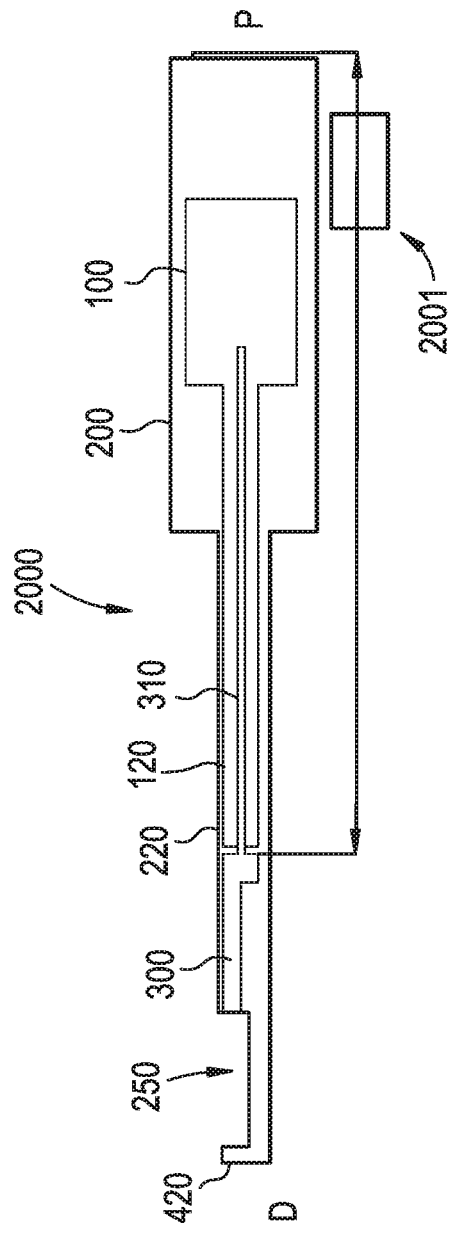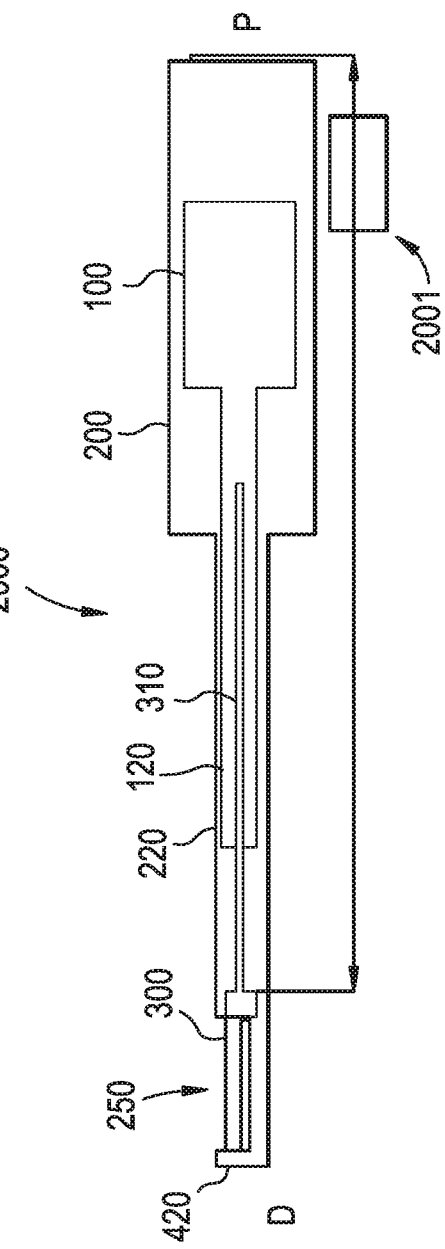

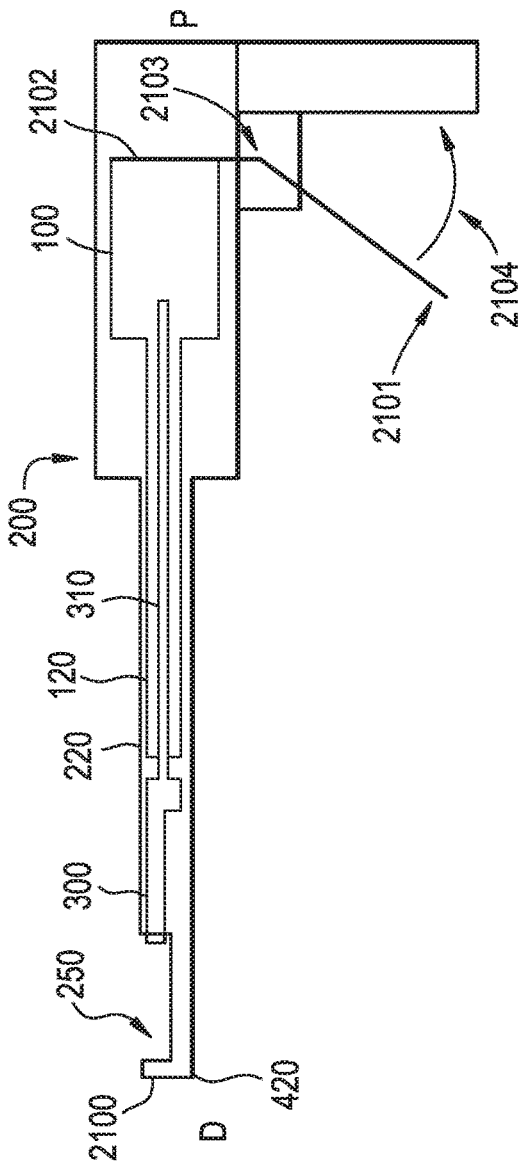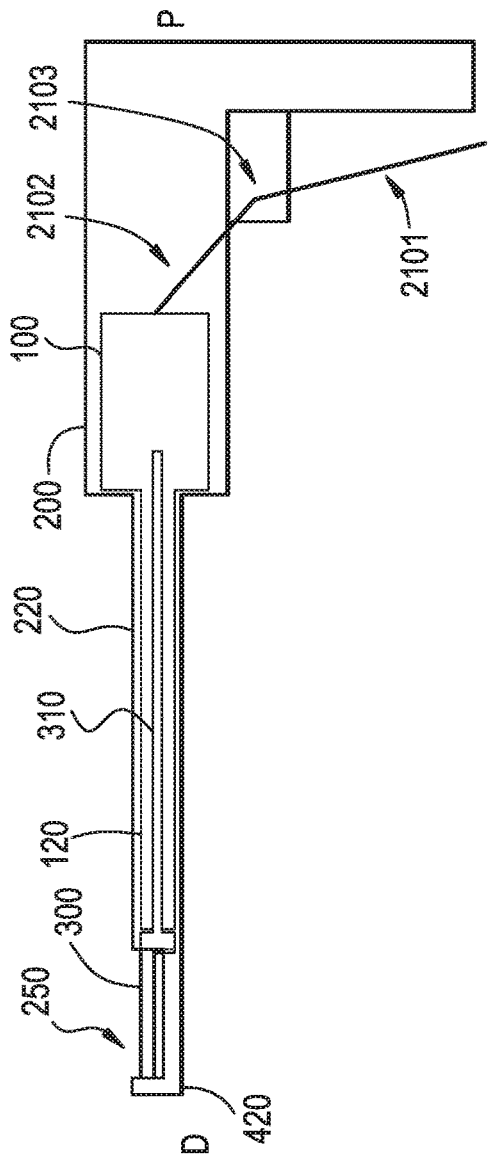

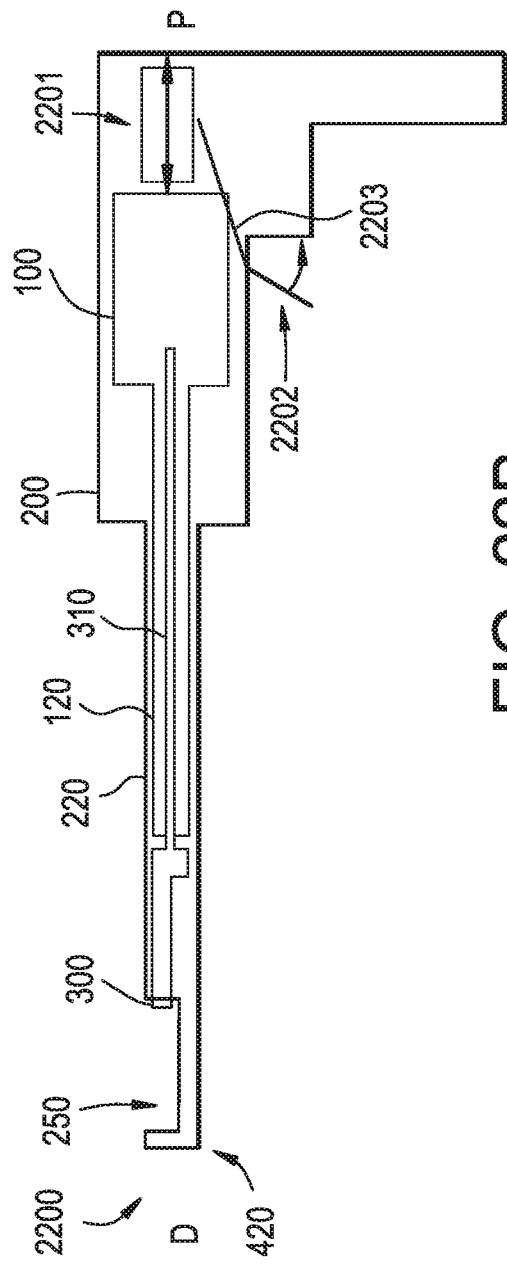
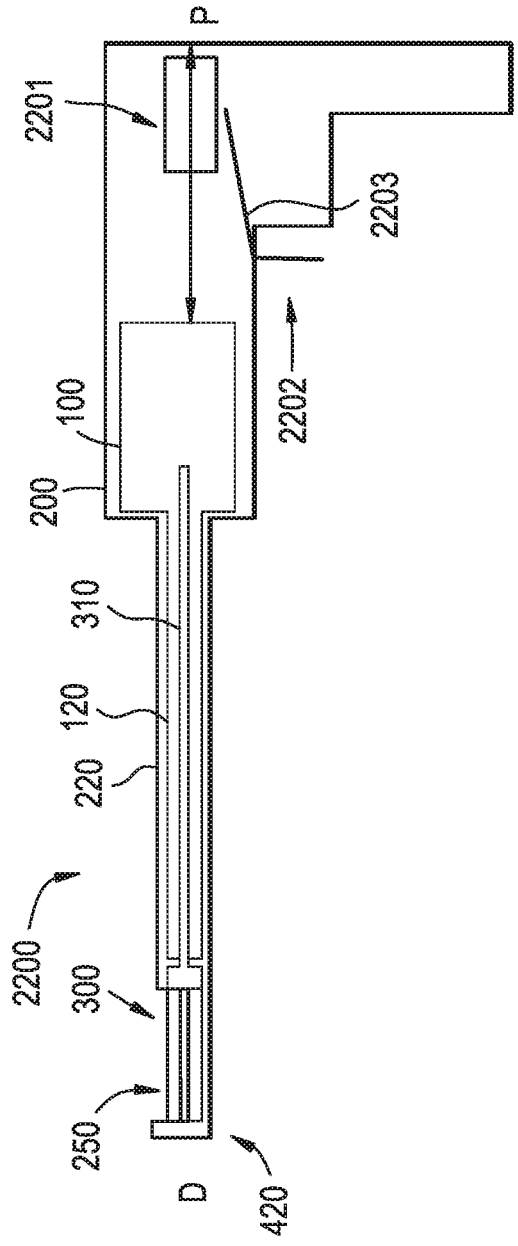
FIG. 22A
FIG. 22B

BONE AND TISSUE RESECTION DEVICES AND METHODS

FIELD

The present disclosure relates to systems, devices, and methods for resecting soft tissue or bone, and more particularly relates to such devices that can aid a user in resecting soft tissue in constrained environments, such as during minimally-invasive surgical procedures.

BACKGROUND

Various surgical procedures involve the removal or manipulation of tissue at a surgical site. For example, in spinal surgeries there is often a need to remove tissue, including bone, to achieve goals such as increasing or providing access to another site (e.g., an intervertebral space), relieving pressure on nerves, etc. A number of instruments exist to perform these tasks, but often have various shortcomings. For example, poor instrument ergonomics can lead to musculoskeletal disorders, surgeon fatigue and stress, and reduced accuracy. In some cases the devices can be manually operated, and therefore slow to complete the task while requiring high levels of muscle activation from the surgeon or other user. Whether manually actuated or not, slow overall resection rates can also be caused by the need for multiple instrument passes and repeated cleaning of tissue from the instrument. Still further, inaccurate removal can result from the instrument moving relative to the tissue being resected or manipulated, a factor that can also result in additional instrument passes or actuations being required.

There is also a potential to damage sensitive nerves and vessels with many prior devices due to movement of a cutting tool relative to soft tissue (e.g., a rotating blade) and the exposure of these tissues to the blade itself. With some devices, resected tissue can be pulverized or otherwise destroyed by a device, such that removal of the tissue more difficult and/or inspection of removed tissue is impossible. A further drawback of prior devices is that the surgeon's view of the bone or tissue being resected or manipulated can be obstructed by the tool itself, which can lead to unintentional iatrogenic trauma.

If a path is being cleared to make way for an implant or another instrument, then a constant cross section through cut is necessary. Current instruments such as a burr that perform resection tasks without making a straight cut like an osteotome run the risk of resecting either too much or too little bone in these circumstances.

Devices such as a burr that grind or otherwise convert targeted tissue to smaller sized particulate or slurry can damage the targeted tissue reducing the ability for it to be used as autograft in other aspects of the procedure.

Moreover, spine and other surgical procedures are increasingly performed using minimally invasive surgical (MIS) and/or microsurgical techniques, which can have a number of advantages, including reduced risk of patient injury, faster recovery time, etc. Such procedures are typically performed using various access ports or retractors that provide a passageway from the skin surface to the spine and intervertebral disc space. These ports and retractors often provide passageways of minimal size, perhaps about 30 mm in diameter or less, in order to minimize tissue trauma and successfully traverse narrow anatomical passages. While these procedures provide a number of benefits, they can increase the difficulty of performing various tissue resection or manipulation operations, as the surgical site is accessed through these narrow ports or retractors. The above-noted drawbacks of prior tissue resection or manipulation tools can therefore be exacerbated in minimally invasive or microsurgical procedures.

Accordingly, there is a need for improved devices and methods for performing bone and tissue resection or manipulation.

SUMMARY

Certain aspects of the present disclosure provide for devices and methods for resecting or manipulating bone and tissue that utilize powered cutting systems with an oscillating or continuously rotating blade, or an axially oscillating blade, to manipulate the border of targeted tissue. The blade can either be exposed or within a housing that can aid in preventing unintentional tissue resection. Aspects of the present disclosure include the mechanics of achieving said oscillating or continuous rotation, or axial oscillation, as well as various forms of user interface or ergonomics, activation methods for a powered cutting system, cut shapes made by the tool, features to navigate the tool to or within a surgical site, features to visualize the cut tissue, and features to provide monitoring feedback, among others.

Embodiments of the present disclosure can include a powered cutting system using a crescentic blade that cuts tissue or bone by oscillating without spinning through a complete rotation and being translated into the bone or tissue against a footplate. The oscillating blade can prevent or reduce nerve damage by avoiding excessive tangling of nerve tissue due to a small angular displacement oscillation and limiting the magnitude of the strain to the soft tissue. Additionally, high frequency oscillations can enable the blade to slice bone with less force and damage, as opposed to hydraulic or pneumatic systems for crushing of bone, which require large amounts of force, or burr systems that obliterate bone and can entangle and damage nerve tissue with the spinning burr.

Embodiments of the present disclosure can include a powered cutting system using a cylindrical blade that features a shroud to protect tissue that is not targeted from resection from the cutting element.

Certain embodiments of the present disclosure can include a mechanical transmission or oscillator that converts the rotation of a motor into oscillation. In one embodiment, the oscillator can use a linear sleeve and piston arrangement to provide blade oscillation rates of at least about 80,000 oscillations per minute. Other embodiments can include a four-bar linkage oscillator to achieve different ranges of oscillation rate and oscillation angle. Both oscillator systems can provide improvements over prior mechanisms, such as a Scotch yolk, which are not suited to high rates of oscillation as described herein. Certain embodiments of the oscillator can also include a torsional harmonic damper to separate oscillation from a motor.

Certain embodiments of the present disclosure include a cutting assembly comprising a footplate and crescentic blade configured to extend distally from a sleeve to the footplate. In some embodiments, the crescentic blade can enable a smaller form factor of the cutting assembly. Additionally, in some embodiments, the footplate can be attached to the sleeve with one or more support members that allow the blade to be viewed from either the top or bottom as it passes though the cutting region. In some embodiments, the blade can extend from a slot in the distal end of the sleeve such that, when retracted, the blade can be cleaned of debris as it passes though the slot.

Example embodiments of the present disclosure include a bone and tissue resection device including a blade having a distal cutting edge configured to perform a cutting action that produces a plug or core from a media being cut by the cutting edge, a drive mechanism arranged to transfer an oscillating force to the cutting edge for oscillating the cutting edge, a shield positioned to block contact with a portion of the cutting edge, and a depth adjustment mechanism configured to translate the cutting edge along a proximal-distal axis of the shield to adjust an axial position of the cutting edge relative to the shield. The drive mechanism can include a four bar linkage oscillator that converts rotation from a motor coupled to the drive mechanism into the oscillating force. The drive mechanism can include a motor that rotates in opposite directions to produce the oscillating force. The drive mechanism can include a scotch yoke mechanism. The drive mechanism can include an eccentric shaft having an offset bearing coupled with a linear bearing to generate the oscillating force, wherein the linear bearing is coupled to the cutting edge. The drive mechanism can produce an oscillating axial motion of the cutting edge along a proximal-distal axis of the cutting edge.

The drive mechanism can include a cam mechanism configured to produce the oscillating axial motion of the cutting edge. The drive mechanism can include a piezoelectric mechanism configured to produce the oscillating axial motion of the cutting edge. The oscillating force can cause oscillation of the cutting edge around a proximal-distal axis of the cutting edge. In some embodiments, the oscillating force causes oscillation of the cutting edge around a proximal-distal axis of the cutting edge, and wherein the drive mechanism is configured to produce an oscillating axial motion of the cutting edge along the proximal-distal axis of the cutting edge while the cutting edge oscillates around the proximal-distal axis of the cutting edge.

The cutting edge can define a crescentic shape such that the plug or core of the media being cut can be extracted through an open side of the blade. The cutting edge can define a shape matching an implant, such that the plug or core cut from a media clears a path for implantation of the implant in the media.

The shield can include a closed distal end configured to prevent contact with the cutting edge. In some embodiments, the shield includes an open distal end configured to enable the blade to be inserted from the distal end into drive mechanism. The shield can define one or more openings located radially from the cutting edge to expose the cutting edge.

In some embodiments, the cutting edge defines a crescent shape and the blade defines and concave surface and a convex surface opposite the concave surface, and the shield defines an opening radial to the convex surface of the blade and closed region radial to the concave surface, such that the opening of the shield enable a user to view the blade and the closed region contains media resected by the cutting edge.

In some embodiments, the cutting edge defines a crescent shape and the blade defines and concave surface and a convex surface opposite the concave surface, and the shield defines a first opening radial to the convex surface of the blade and a second opening radial to the concave surface of the blade, and the shield defines one or more posts separate the two openings, the one or more posts extending to a distal end of the shield. In some embodiments, the shield includes a protrusion extending towards the concave surface of the blade for extracting material from the concave surface the blade when the blade is translated in a proximal direction by the depth adjustment mechanism after be driven distally to cut the material. The depth adjustment mechanism can be configured to adjust the axial position of the cutting edge with respect to the shield without adjusting the axial position of the drive mechanism with respect to the shield. The depth adjustment mechanism can be configured to adjust the position of the cutting edge by translating the drive mechanism along the proximal-distal axis of the shield.

In some embodiments, the bone and tissue resection device includes a handle, and the depth adjustment mechanism is configured to be operated by a user via the handle, such that, when a user applies a force to the handle, the depth adjustment mechanism transfers the force from the handle to the blade to adjust the position of the cutting edge. The depth adjustment mechanism can include a powered mechanism operable by a user to adjust the position of the cutting edge relative to the shield.

In some embodiments, the drive mechanism includes an input shaft configured to continuously rotate about a first central axis, a portion of a length of the input shaft defining an eccentric section, the eccentric section defining a second central axis that is offset from the first central axis, a linkage disposed around the eccentric section at a first end thereof and having a lumen formed in a second end thereof that is parallel to and offset from the second central axis, a pin disposed within the lumen of the linkage, and an oscillating shaft coupled to and offset from the pin. Where continuous rotation of the input shaft about the first central axis creates an oscillating movement of the oscillating shaft. In some embodiments, the blade is coupled to the oscillating shaft. In some embodiments, the input shaft further comprises a counter weight to balance to rotation of the eccentric section about the first central axis.

In some embodiments, the bone and tissue resection device includes a bearing disposed around the input shaft. In some embodiments, the bone and tissue resection device includes a bearing disposed around the oscillating shaft. In some embodiments, the bone and tissue resection device includes a collet formed at a distal end of the oscillating shaft, the collet including a plurality of arms extending distally around a central axis of the oscillating shaft.

In some embodiments, the shield is configured to detect nerves within a path of the cutting edge using electromyography (EMG) or mechanomyography (MMG). In some embodiments, the shield is able to be navigated to enable alignment of a cut area of the cutting edge.

Another example embodiment is a bone and tissue resection device including a stationary assembly with a housing, an elongated sleeve extending distally from the housing, and a cutting region disposed distal to the sleeve, and a drive assembly including a blade shaft extending through the elongated sleeve, the blade shaft having a distal tip with a blade, wherein a cutting edge of the blade is configured to extend into the cutting region when the drive assembly advances distally relative to the stationary assembly, and a drive mechanism coupled to the blade shaft and configured to engage with a source of continuous rotational motion, the drive mechanism configured to convert the continuous rotational motion into oscillating motion of the drive shaft. Where the drive assembly is configured to slidably couple to the stationary assembly to permit selective proximal and distal translation of the drive assembly relative to the stationary assembly by the depth adjustment mechanism. The blade can be sized to span the depth of the cut-out of the elongated sleeve. In some embodiments, the stationary assembly includes a handle coupled to the housing, and the drive assembly includes a trigger configured to receive a force to move the drive assembly relative to the stationary assembly. The trigger can be positioned distal to the handle. The trigger can be positioned proximal to the handle.

The stationary assembly can include a handle coupled to the housing, and a trigger assembly configured to move with respect to the handle, the trigger assembly configured to receive a force to move the trigger assembly and transfer the force to the drive assembly to move the drive assembly. In some embodiments, the stationary assembly includes a linear actuator configured to deliver linear motion to the drive assembly, and wherein the trigger assembly is operatively coupled with the linear actuator. In some embodiments, the linear actuator is a rack and pinion system comprising a first rack configured to be moved by the trigger assembly and a second rack configured to move the drive assembly. In some embodiments, drive assembly comprises the second rack of the rack and pinion system.

The bone and tissue resection device of claim 8, wherein the rack and pinion system comprises a pinion assembly having first and second beveled pinions disposed along a common axis of rotation, wherein the first and second beveled pinions are biased towards each along the common axis of rotation by one or more biasing elements. In some embodiments, the trigger assembly comprises an actuation lever and a trigger, the actuation lever is configured to engage with the drive assembly and translate the drive assembly distally when the trigger is moved towards the handle. In some embodiments, the trigger assembly is configured to rotate about an axis perpendicular to a longitudinal axis of the stationary assembly.

In some embodiments, the handle extends along a longitudinal axis of the stationary assembly, and the trigger assembly is configured to translate along an axis perpendicular to the longitudinal axis of the stationary assembly.

In some embodiments, the drive assembly includes a housing having one or more mating features, the housing of the stationary assembly includes one or more corresponding mating features, and the corresponding mating features of the stationary assembly are arranged to be removably coupled with the mating features of the drive assembly and, when coupled, retain the drive assembly to the stationary assembly. In some embodiments, the corresponding mating features of the stationary assembly are configured to slidably couple to the mating features of the drive assembly such that the drive assembly is able to translate proximally and distally along a longitudinal axis of the stationary assembly. In some embodiments, the corresponding mating features of the stationary assembly include one or more guide rails, and the mating features of the drive assembly include one or more protrusions sized and shaped to travel along the guide rails.

In some embodiments, the drive assembly comprises a coupling configured to be mechanically connected with a motor providing the continuous rotational motion, the coupling configured to transfer rotational energy from the motor to the drive mechanism.

In some embodiments, the elongated sleeve is removably coupled to the stationary assembly.

The bone and tissue resection device can include a biasing element configured to bias the drive assembly proximally with relative to the stationary assembly. The bone and tissue resection device can include a powered actuator configured to move the drive assembly relative to the stationary assembly. In some embodiments, the powered actuator is any of electric, pneumatic, or hydraulic. In some embodiments, the device includes a trigger operatively coupled with the powered actuator and configured to control movement of the drive assembly using the powered actuator.

In some embodiments, the elongated sleeve comprises an electromyography (EMG) or mechanomyography (MMG) sensor configured to detect nerves within the cutting region. In some embodiments, the elongated sleeve is able to be navigated to align the cutting region.

Yet another example embodiment of the present disclosure is a cutting assembly for a bone and tissue resection device, including a blade shaft having a distal end with an arcuate blade, a sleeve surrounding the blade shaft and arcuate blade, the sleeve having a distal end defining an opening sized and shaped to allow the arcuate blade to translate distally beyond the distal end of the sleeve, a footplate positioned beyond the distal end of the sleeve and configured to resist distal movement of material being cut by the arcuate blade when the arcuate blade is translated distally against the material, and a support extending from the distal end of the sleeve to the footplate, the support element defining a cutting region between the distal end the sleeve and the footplate. The arcuate blade can be configured to oscillate about a longitudinal axis of the blade shaft. The arcuate blade can be a crescentic blade. In some embodiments, the distal end of the sleeve is partially closed and comprises a crescentic opening configured to allow the crescentic blade to pass through the crescentic opening. In some embodiments, the cutting region is further defined by a path of the exposed arcuate blade along the support when the arcuate blade is translated beyond the distal end of the sleeve towards the footplate. In some embodiments, the footplate defines an outer edge that extends radially beyond an outer edge of the arcuate blade. In some embodiments, the footplate defines an arcuate lip along the outer edge that extends towards the arcuate blade. In some embodiments, the footplate defines an arcuate trough formed in a proximal-facing surface of the footplate, where an outer edge of the trough is defined by the arcuate lip, and the arcuate trough is configured to receive the arcuate blade.

The support can include first and second beams extending distally from the sleeve to the footplate. In some embodiments, the arcuate blade is configured to translate between the first and second beams. The support can be configured to allow the arcuate blade to pass along an outside of the support beam as the arcuate blade is translated distally towards the footplate. The blade shaft can be configured to be removably coupled to a drive mechanism of the bone and tissue resection device. In some embodiments, the sleeve is configured to be removably coupled to a stationary component of the bone and tissue resection device at a proximal end thereof. In some embodiments, the sleeve defines an elongated tubular structure having an inner diameter sized to accept an outer diameter of the arcuate blade.

In some embodiments, at least one of the sleeve, the footplate, and the support includes a stop configured to contact any of the arcuate blade and the blade shaft to prevent the arcuate blade from contacting the footplate. In some embodiments, the footplate has a distal opening sized to allow the blade to be inserted from the distal end. In some embodiments, the footplate, sleeve, and support are formed in a tubular structure having one or more openings to expose tissue to a blade in desired directions allowing the blade to only cut material exposed through the openings.

Still another example embodiment of the present disclosure is an oscillator for converting continuous rotational motion into oscillating motion. The oscillator includes an input shaft configured to continuously rotate about a first central axis, a portion of a length of the input shaft defining an eccentric section, the eccentric section defining a second central axis that is offset from the first central axis, a connector rotatably coupled around the eccentric section, an oscillating shaft offset from the input shaft and configured to rotate about a third central axis, and a pin coupled to the oscillating shaft and extending towards the connector. Where the connector comprises a sleeve slidably receiving an end of the pin, and continuous rotation of the input shaft about the first central axis causes an eccentric movement of the connector, and the eccentric movement of the connector oscillates the sleeve along the pin and oscillates the pin with respect to the oscillating shaft, thereby oscillating the oscillating shaft about the third central axis.

The pin and sleeve can extend perpendicular to the axis of the eccentric section of the input shaft and the oscillating shaft. The pin and sleeve can be slidably connected such that the pin and sleeve are free to translate along each of their major axes. The pin can be connected to the eccentric section of the input shaft by a bearing or bushing such that the pin cannot translate radially away from the second central axis. The pin can be rigidly coupled to the oscillating shaft such that the pin cannot move radially with respect to the third central axis. The sleeve can be connected to the eccentric section of the input shaft by a bearing or bushing such that it cannot translate radially away from the second central axis. The sleeve can be directly connected to the oscillating shaft such that it cannot translate radially away from the second central axis. In some embodiments, input shaft is parallel to the oscillating shaft.

In some embodiments, the oscillator includes a cutting tool coupled to the oscillating shaft. In some embodiments, the input shaft includes a counter weight to balance to rotation of the eccentric section about the first central axis. In some embodiments, the oscillator includes a bearing disposed around the input shaft. In some embodiments, the oscillator includes a bearing disposed around the oscillating shaft. In some embodiments, the oscillator includes a collet formed at a distal end of the oscillating shaft, the collet including a plurality of arms extending distally around a central axis of the oscillating shaft.

In some embodiments, the oscillator includes a retainer having a central lumen, where the retainer is slidably disposed around the plurality of arms of the collet. In some embodiments, the oscillator includes a release actuator configured to translate the retainer relative to the plurality of arms of the collet. In some embodiments, a proximal surface of the retainer extends at an oblique angle to the central axis of the oscillating shaft, where the release actuator is configured to translate in a direction perpendicular to the central axis of the oscillating shaft and includes a surface that abuts the proximal surface of the retainer.

Another example embodiment of the present disclosure is a surgical instrument, including a housing, an elongated sleeve extending from the housing, an input configured to receive continuous rotational motion, an output configured to couple to an end effector extending through the sleeve beyond a distal end thereof, and an oscillator configured to convert the continuous rotational motion of the input into oscillating motion of the output. The instrument can include an end effector release with an actuator to operate the end effector release, the end effector release being configured to selectively couple and decouple the end effector to the output. In some embodiments, the end effector release comprises a collet. In some embodiments, the end effector is a blade. In some embodiments, the blade is crescentic.

In some embodiments, the oscillator input further comprises an input shaft having an eccentric section defining a central axis that is offset from a rotational axis of the shaft, the output includes an output shaft offset from the input shaft, and a linkage is disposed around the eccentric section of the input shaft at a first end thereof and coupled to the output shaft at a second end thereof to oscillate the output shaft in response to rotation of the input shaft. In some embodiments, the linkage is coupled to the output shaft by the second end of the linkage being slidably received within a bore of the output shaft. In some embodiments, the linkage is coupled to the output shaft by a pin extending through a lumen formed in the second end of the linkage, where the pin extends parallel to and is offset from a central axis of the output shaft.

In some embodiments, the instrument includes a frame slidably coupled to the housing. In some embodiments, the frame is coupled to a handle configured to be grasped by a user. In some embodiments, the handle extends parallel to a longitudinal axis of the instrument. In some embodiments, the handle extends transversely to a longitudinal axis of the instrument.

In some embodiments, the instrument includes a trigger configured to control translation of the housing relative to the frame. The trigger can translate relative to the frame along an axis parallel to a longitudinal axis of the instrument. The trigger can translate relative to the frame along an axis transverse to a longitudinal axis of the instrument. In some embodiments, the trigger pivots relative to the frame along an axis perpendicular to a longitudinal axis of the instrument. In some embodiments, frame is coupled to a second sleeve that receives the elongate sleeve within a lumen thereof. In some embodiments, the second sleeve has an opening formed at a distal end thereof to permit the end effector to extend beyond the distal end of the second sleeve.

In some embodiments, the instrument includes an actuator to control coupling of the second sleeve to the frame. In some embodiments, the instrument includes a biasing element to resist distal translation of the housing relative to the frame.

Any of the features or variations described above can be applied to any particular aspect or embodiment of the present disclosure in a number of different combinations. The absence of explicit recitation of any particular combination is due solely to the avoidance of repetition in this summary.

BRIEF DESCRIPTION OF DRAWINGS

This disclosure will be more fully understood from the following detailed description taken in conjunction with the accompanying drawings, in which:

FIG. 3A is an illustration of another embodiment of a bone and tissue resection device according to the present disclosure;

FIG. 3C is an illustration of the drive assembly of the bone and tissue resection device of FIG. 3A;

FIG. 3D is an illustration of the distal end of the drive assembly of FIG. 3C with a blade attached;

FIGS. 7A-7C are illustrations of one embodiment of a bone and tissue resection device having a pivoting trigger configured to actuate the movement of the drive assembly;

FIG. 8 is an illustration of another embodiment of a bone and tissue resection device having an alternative grip and trigger arrangement;

FIGS. 9A-9G are illustrations of embodiments of a bone and tissue resection device having a rack and pinion arrangement between the stationary assembly and the drive assembly;

FIGS. 11A-11C are illustrations of one embodiment of a bone and tissue resection device having a longitudinally extending handle and trigger arrangement;

FIGS. 12A-12H are illustrations of one embodiment of a drive assembly having a piston oscillator;

FIGS. 13A-13F are illustrations of one embodiment of a drive assembly having a four bar linkage oscillator;

FIGS. 19A and 19B are illustrations of one embodiment of a bone and tissue resection device with a depth adjustment mechanism for adjusting the position of a cutting edge by translating a drive mechanism.

FIGS. 20A and 20B are illustrations of one embodiment of a bone and tissue resection device with a depth adjustment mechanism configured to adjust the axial position of the cutting edge with respect to the shield without adjusting the axial position of the drive mechanism FIGS. 21A and 21B are illustrations of one embodiment of a bone and tissue resection device with a depth adjustment mechanism that includes handle configured to be operated by a user to apply a force to advance a cutting edge; and FIGS. 22A and 22B are illustrations of one embodiment of a bone and tissue resection device with a powered depth adjustment mechanism operable to adjust the position of a cutting edge.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Additionally, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can easily be determined for any geometric shape. Further, in the present disclosure, like-numbered components of the embodiments generally have similar features. Still further, sizes and shapes of the devices, and the components thereof, can depend at least on the anatomy of the subject in which the devices will be used, the size and shape of components with which the devices will be used, and the methods and procedures in which the devices will be used.

Example Powered Cutting Systems

Figure 1:
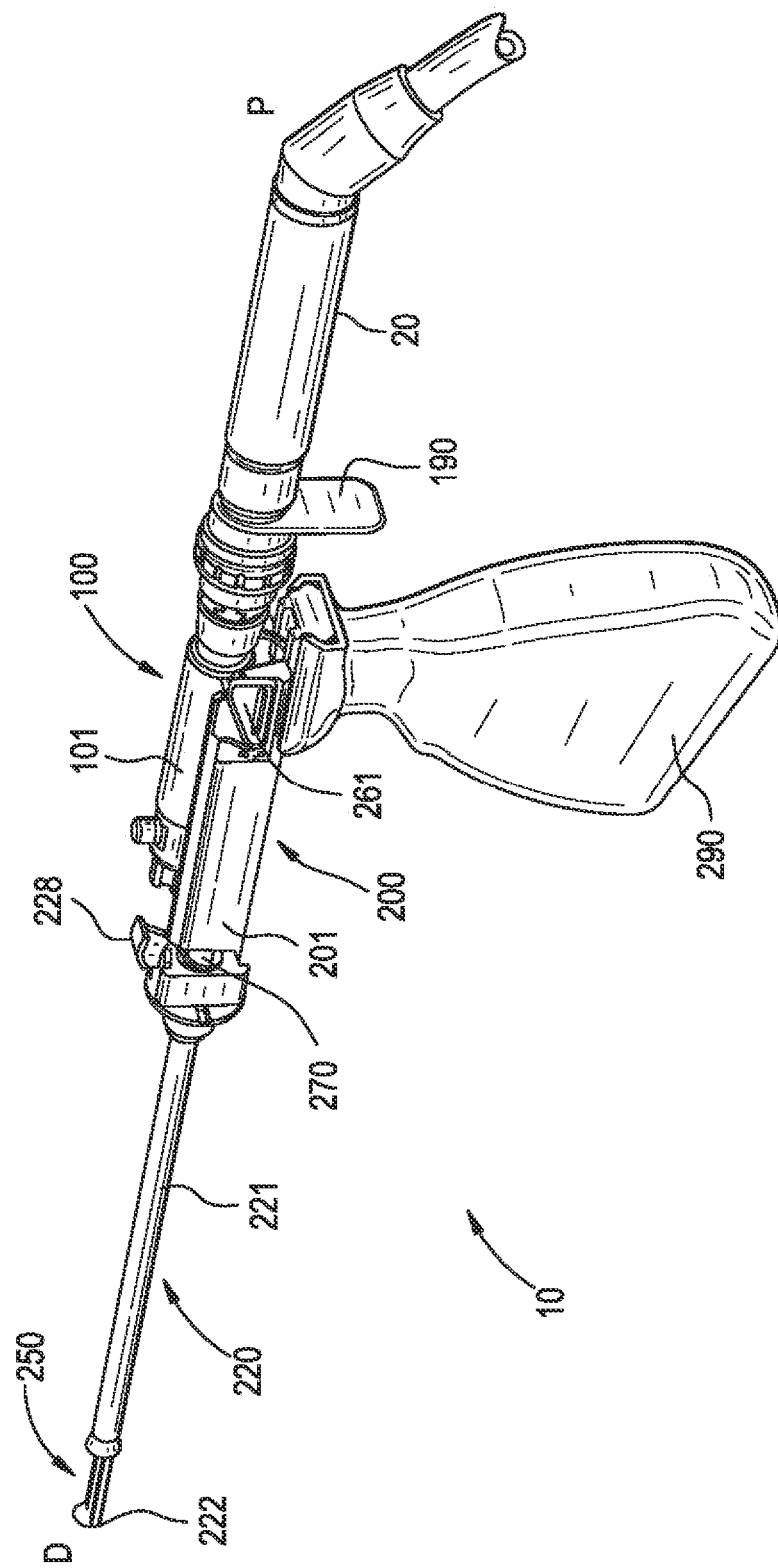
FIG. 1 is an illustration of one embodiment of a bone and tissue resection device according to the present disclosure.

FIG. 1 is an illustration of one embodiment of a bone and tissue resection device according to aspects of the embodiments disclosed herein. FIG. 1 shows a bone and tissue resection device 10 that includes a stationary assembly 200 and a drive assembly 100 slidably coupled with the stationary assembly 200. The drive assembly 100 includes a housing 101 that is coupled with a motor 20 (e.g., a source of continuous rotational motion) and a thumb trigger 190 positioned to allow a user to slide the drive assembly in the distal (D) direction with respect to the stationary assembly 200. The stationary assembly 200 includes a frame 201 that is slidably engaged with the housing 101 of the drive assembly and a handle 290 sized and shaped to allow a user's fingers and/or palm hold onto the handle 290 of the stationary assembly 200 while the user's thumb actuates the thumb trigger 190 of the drive assembly 190. The stationary assembly 200 includes a spring 270 positioned in the frame 201. The spring 270 is positioned to bias the drive assembly 100 in a proximal (P) direction against the force of the user against the thumb trigger 190, thus maintaining the normally open position of the cutting region 250. In some embodiments, the spring 270 is positioned to bias the oscillator 100 distally inside the stationary assembly 200 such that the cutting region 250 is normally closed. Actuating the oscillator 100 in this configuration forces the cutting region 250 open and releasing the trigger 190 would cause the spring 270 to provide a constant force on the blade until it closes and makes the cut in the cutting region 250.

The stationary assembly 200 includes a shield assembly 220 that extends from the frame 201 to a footplate 222 at the distal end. In some embodiments, the shield assembly 220 is integrated with the stationary assembly. FIG. 1 shows a shield assembly 220 that is coupled to a distal end of the frame 201 of the stationary assembly 200 with a clip 228. The shield assembly 220 includes an elongated sleeve 221 that extends distally from the frame 201 to a cutting region 250 where there is a window opening along the shield assembly 220 from a distal end of the elongated sleeve 221 to the footplate at the distal end of the shield assembly 220. The shield assembly 220 is configured to protect a blade (not visible) that is coupled to the drive assembly 100.

In operation, the drive assembly 100 transfers energy to the blade from the motor (e.g., causes the blade to oscillate or rotate inside the shield assembly 220) and actuation of the thumb trigger 190 (e.g., a force applied in the distal direction by a user holding the handle 290) slides the drive assembly 100 distally against the bias force of the spring 270. The distal movement of the drive assembly causes the blade to pass through the cutting region 250. Tissue or bone present in the cutting region 250 is contacted and resected by the blade as it passes though. In some embodiments, the blade is a crescentic blade that oscillates at a high frequency with a small angular deviation. In some embodiments, the blade is abrasive and will be less effective at cutting soft tissue than it will bone thus improving safety.

Figure 2:
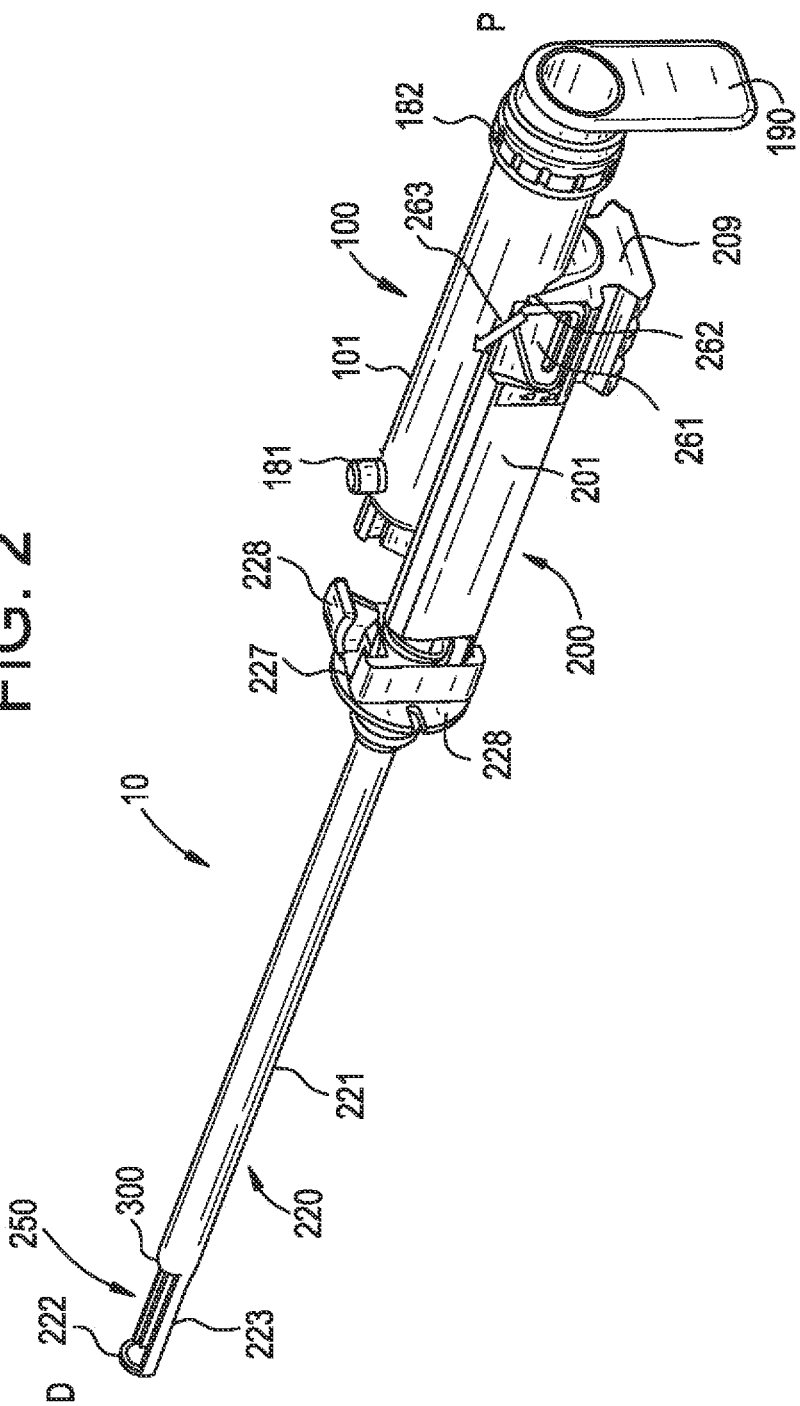
FIG. 2 is an illustration of the stationary and drive assemblies of the bone and tissue resection device of FIG. 1.

FIG. 2 is an illustration of the stationary and drive assemblies of the bone and tissue resection device of FIG. 1. FIG. 2 show the stationary assembly 200 and drive assembly 100 with the handle 290 of the stationary assembly detached from the frame 201 of the stationary assembly. In some embodiments, the handle 290 is integrated with the frame 201. FIG. 2 shows the frame 201 includes an interface 209 for securing a separate handle 290 to the stationary assembly 200. The shield assembly 220 is attached to the frame 201 of the stationary assembly 220 with a clip 228 that engages with a distal channel 227 formed in the frame 201. The cutting region 250 of the shield assembly 220 includes two support members 223 that connect the foot plate 222 to the distal end of the elongated sleeve 221. Also visible is a blade tip of a blade 300 disposed inside the shield assembly 220 and attached to the drive assembly via a blade shaft (not visible). The drive assembly 100 includes a button actuator 181 extending through the housing 101 for releasing the blade shaft from being coupled with the drive mechanism inside the housing 101. The proximal end of the drive assembly 100 includes a coupling mechanism 182 for attaching the motor 20 to the drive mechanism. When coupled, continuous rotational motion from the motor 20 is delivered to a drive mechanism inside the housing 101 of the drive assembly 100. Additionally, FIG. 2 shows the frame 201 of the stationary assembly includes a latch 261 that can prevent the drive assembly 100 from decoupling with the frame 201 when in the first illustrated position (e.g., via a protrusion 262 that interferes with proximal motion of the drive assembly 100 relative to the frame 201) and can be moved to a second position (e.g., by rotating a proximal end of the latch 261 in the direction of arrow 263) to allow decoupling of the drive assembly 100 from the frame 201 (e.g., by withdrawing the drive assembly 100 proximally with respect to the frame 201).

FIG. 3D is an illustration of how in operation, a disposable blade 300 can be attached to the drive assembly 100 while the drive assembly is separated from the stationary assembly 200 and a disposable shield assembly 220 is attached to the stationary assembly. Afterwards, the distal end of the blade 300 can be inserted into the shield assembly 220 and slid distally until the drive assembly 100 is engaged with the stationary assembly 200 and retained by the latch 261. In this position, the drive assembly can be biased proximally against the latch 261 by the spring 270, which positions the distal tip of the blade 300 at the proximal end of the cutting region 250. When a user presses on the thumb trigger 190 in the distal direction, the drive assembly moves against the bias force of the spring 270 to drive the blade 300 through the cutting region to conduct a cutting operation.

FIG. 3A is an illustration of another embodiment of a bone and tissue resection device 10 according to aspects of the embodiments disclosed herein. FIG. 3A shows a bone and tissue resection device 10 with a different handle 390 attached to the frame 201 of the stationary assembly 200. FIG. 3A shows the motor 20 is coupled to an external controller or power source via a line 22 connected to the motor 20 with an articulating coupling 21. FIG. 3A also shows that the blade 300 is a crescentic blade that is configured to be oscillated by an oscillator mechanism of the drive assembly 100. The crescentic blade can span the width of the two support beams 223 of the shield assembly 220 such that the cutting region 250 (e.g., the path of the blade 300) is an arc from one support beam 223 to the other support beam 223 across the width of the shield assembly 220 that extends from a distal end of the elongated sleeve 221 (e.g., where the distal end of the blade 300 is first exposed as it is move distally by the drive assembly) to the foot plate 222. In some embodiments, the cutting region 250 does not extend all the way to the foot plate 222 to prevent the blade 300 contacting the footplate 222. The blade 300 extends inside the support beams 223 but, in some embodiments, and as shown, has a crescentic or generally arcuate shape that forms the cutting region above the support beams 223, but not below, such that there is a window 224 extending between the support beams 223 opposite the blade 300. The window 224 can allow a user or imaging device to observe the cutting region 250 and blade 300 as it contacts and resects tissue. The open window configuration thus enables the blade 300 to be viewed from both sides (e.g., directly from above in the orientation of the figure and through the window 224 from below in the orientation of the figure) as it passes through the cutting region 250. This can be advantageous because, in use, a resection device such as a burr or Kerrison Rongeur is often positioned against bone or tissue in a manner that obstructs direct visualization of the blade 300 from above in the orientation of the figure. Therefore, in prior devices without any window 224, a surgeon or other user can be forced to perform final positioning for a resection cut without being able to see the blade directly.

In some embodiments, the an oscillator mechanism of the drive assembly 100 includes a mechanical arrangement configured to convert continuous rotational motion from a motor, which may be, for example, an internal motor or an external motor 20 attached to the drive assembly, into an oscillating movement for oscillating the blade 300. In some embodiments, the oscillator comprises a piezoelectric mechanism for oscillating the blade 300 at ultrasonic frequencies. In some embodiments, the oscillator oscillates the blade 300 around the proximal-distal axis of the blade 300. In other embodiments, the oscillator oscillates the blade 300 axially along proximal-distal axis of the blade 300. In other embodiments, the oscillator oscillates the blade 300 axially along proximal-distal axis of the blade 300 and around the proximal-distal axis of the blade 300.

Figure 3B:
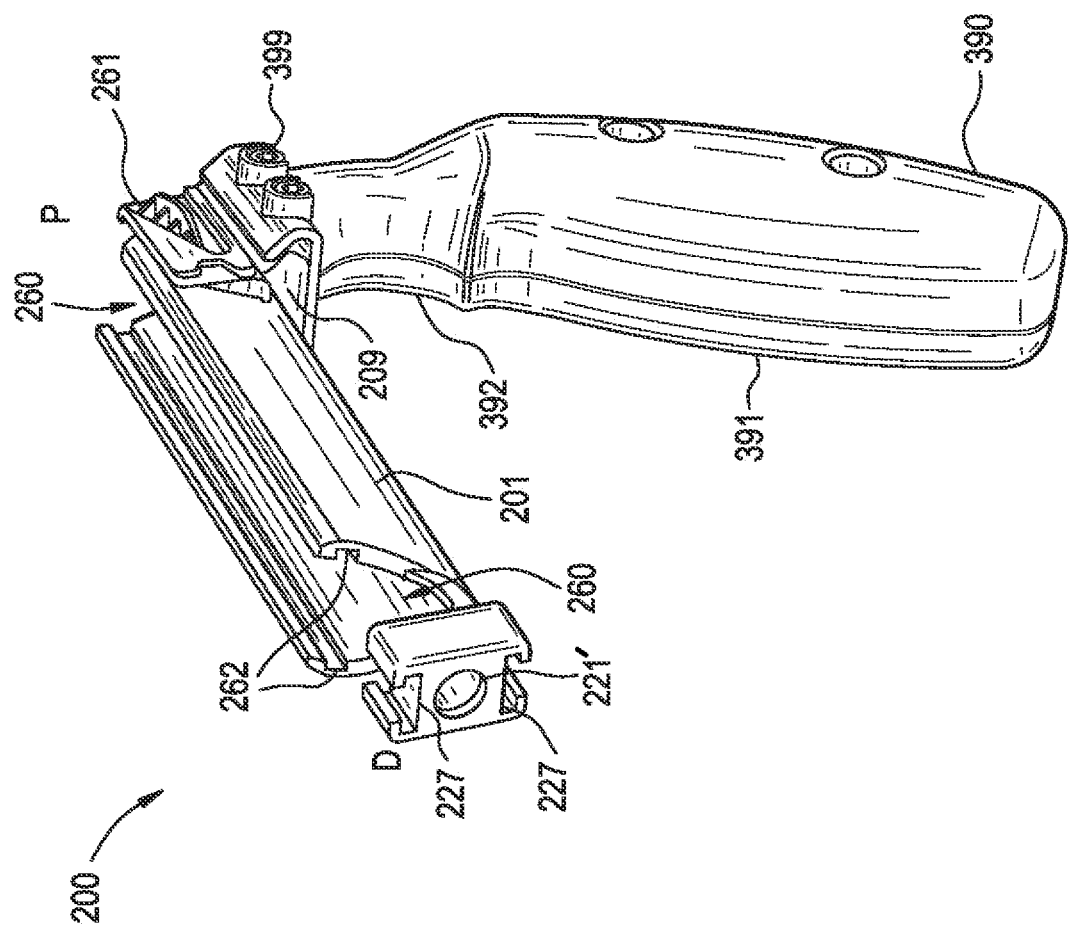
FIG. 3B is an illustration of the stationary assembly of the bone and tissue resection device of FIG. 3A.

FIG. 3B is an illustration of the stationary assembly 200 of the bone and tissue resection device 10 of FIG. 3A. FIG. 3B shows the frame 201 of the stationary assembly 200 with the drive assembly 100 removed or not yet inserted. The handle 390 is shown attached to the interface 209 of the frame 201 via a plurality of screws 399. The handle 390 includes a first gripping portion 391 and a second gripping portion 392, both on the distal face of the handle 390. The second gripping portion 392 is sized and shaped to be engaged by the index finger of a user's hand that is grasping the handle 390, and the first gripping portion 391 is sized and shaped to be engaged by one or more of the user's remaining fingers.

The frame 201 is shown to have a generally C-shaped cross-section that defines a channel 260 that accepts the exterior of the housing 101 drive assembly 100. The channel 260 includes rail features 262 along the channel 260. The rail features 262 permit the housing 101 to slide along a single axis of translation (e.g., along the proximal and distal directions). In some embodiments, the frame 201 can completely encapsulate the drive assembly 100 instead of just being a C-shaped cross-section. In these circumstances, the guide protrusions on the drive assembly 106 and mating rail feature on the frame 262 are no longer necessary but can still be used to constrain movement. The distal end of the frame 201 includes an opening 221' that is sized to accept the blade 300 when the drive assembly 100 is inserted into the stationary assembly 200. The distal end of the frame 201 also provides a surface to be engaged by the spring 270 for biasing the drive assembly 100 in the proximal direction. The distal end of the frame 201 also includes channels 227 for securing the clip 228 of the disposable shield assembly 220 to the stationary assembly 200. The proximal end of the frame 201 includes a latch 261 for retaining the drive assembly in the channel 260 of the frame 201. In operation, the drive assembly 100 is slid into the channel 260 and engaged with the rail features 262, and then the drive assembly slides distally along the path defined by the rail features 262 until secured by the latch 261, which prevents the drive assembly 100 from being removed (e.g., moved in the proximal direction to disengage from the rail features 262). To decouple the components, a user can toggle the latch 262 (e.g., as described above) to release the drive assembly 100 and retract the drive assembly 100 proximally to decouple the drive assembly 100 from the stationary assembly 200.

FIG. 3C is an illustration of the drive assembly 100 of the bone and tissue resection device 10 of FIG. 3A. FIG. 3C shows the drive assembly 100 separate from the stationary assembly 200. In some embodiments, the drive assembly 100 is configured to be used as a free-hand resection device without being coupled with a stationary assembly 200. In FIG. 3C, a blade shaft shield 120 is shown extending distally from the housing 101. The blade shaft shield 120 is configured to protect and constrain the blade shaft between the exit of the housing 101 and the blade 300 positioned at the distal end of the blade shaft (as shown in FIG. 3D). In operation, a proximal end of the blade shaft can be inserted at an opening 122 in the distal tip 121 of the blade shaft shield 120 and the blade shaft can be slid proximally until it engages with a drive mechanism inside the housing 101. In some embodiments, the user can first press the button actuator 181 to enable the blade shaft to be engaged with the drive mechanism. In other embodiments, the button actuator 181 may only need to be depressed to release the blade from the drive mechanism and an applied insertion force to the blade shaft can engage the coupling mechanism without actuation of the button actuator 181 (e.g., via a one-way latch, such as those commonly used on doors, etc.).

FIG. 3C shows the housing 101 of the drive assembly having guide protrusions 106 extending from the housing. The guide protrusions 106 are configured to engage with the rail features 262 of the frame 201 of the stationary assembly 200, as shown in FIG. 3B. The distal end of the housing 101 includes a protrusion 102 that engages the spring 270 of the stationary assembly 100. FIG. 3D is an illustration of the distal end of the drive assembly 101 of FIG. 3C with a blade 300 attached. FIG. 3D shows the crescentic blade 300 with a blade shaft 310 extending proximally from the blade 300 into the blade shaft shield 120. In the illustrated position, the blade 300 is fully inserted into the blade shaft shield 120 and a proximal end of the blade shaft 310 is coupled with the drive mechanism inside the housing 101. The blade 300 is free to oscillate or rotate about the major axis of the blade shaft 310, depending on the type of drive mechanism that is in the housing 101. In some embodiments, the blade can be a circular blade or a coring blade. In operation, a user can free-hand use the drive assembly in this configuration. It should also be noted that a user could change between using the drive assembly free-hand and in connection with a stationary, as well as perhaps using different blade types in each configuration, multiple times during a procedure.

Further, while the above-described embodiments illustrate configurations in which movement of the drive assembly 100 with respect to the stationary assembly 200 is manually actuated, in other embodiments a bone and tissue resection device 10 can include a powered actuator for moving the drive assembly 100 with respect to the stationary assembly 200. In such embodiments, a user of the bone and tissue resection device 10 can electrically or mechanically control the powered actuator to move the drive assembly 100 and thereby move the blade 300 in the cutting region 250.

Example Crescentic Blade Cutting Assemblies

Figure 4A:
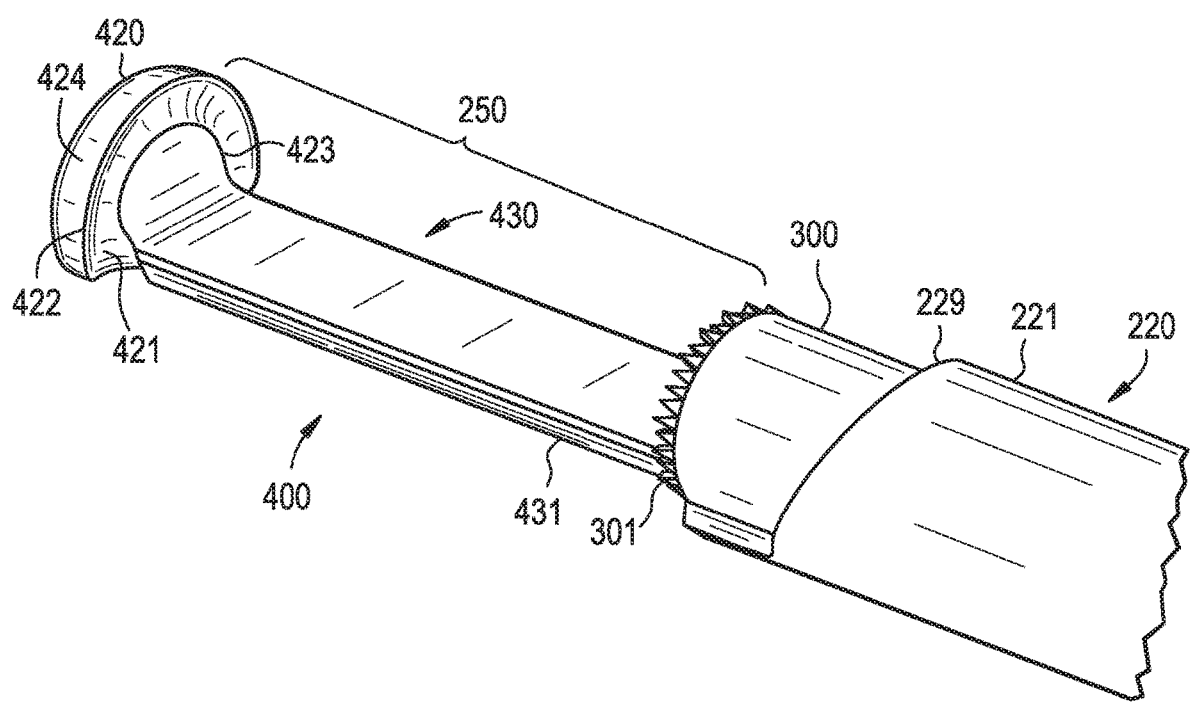
FIGS. 4A-4C are illustrations of one embodiment of a distal end of a drive assembly with a blade according to the present disclosure.
Figure 4B:
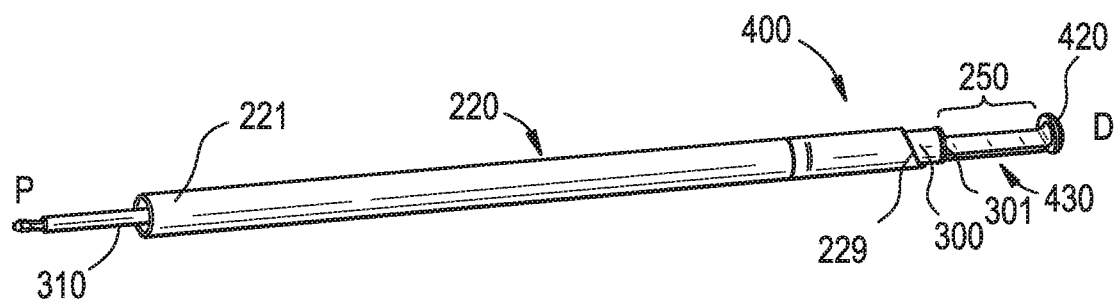
Figure 4C:
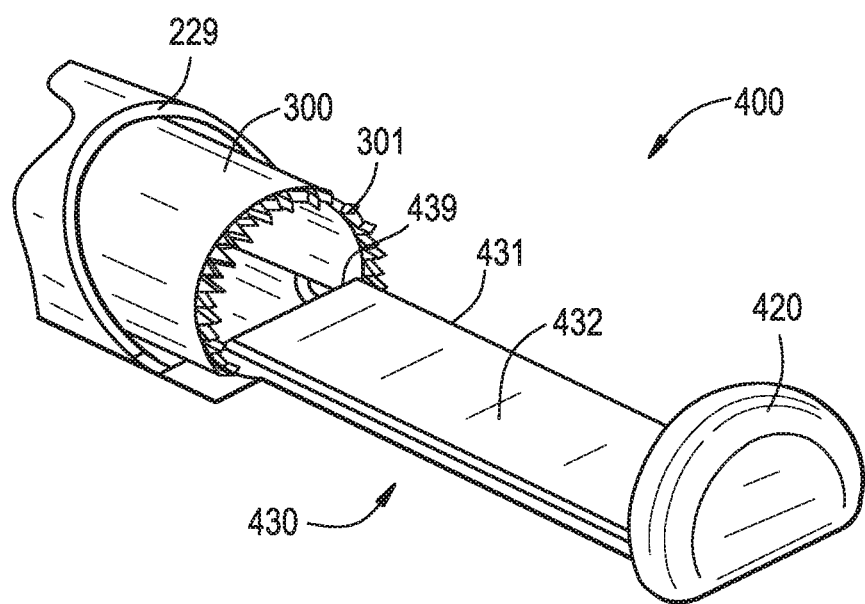

FIGS. 4A-4C are illustrations of an embodiment of a distal end of a device according to aspects of the embodiments disclose herein, such as the device 10 described above. FIG. 4A shows a first embodiment of a cutting assembly 400 that includes the disposable shield 220 and the blade 300. The cutting assembly 400 defines a cutting region 250 between a closed footplate 420 at the distal end and an opening 229 of the distal end of the elongated sleeve 221 of the shield assembly 220. The closed footplate 420 can be coupled to the shield assembly 220 by a single support beam 430 that spans a length of the cutting region 250. In some embodiments, the support beam 430 can be split into multiple support beams to allow for visualization of the cutting area. The support beam 430 can be sized and shaped to be inside of the path of the blade 300 as it transits the cutting region 250. In some embodiments, and as shown, the blade 300 can be a crescentic blade that surrounds the support beam 230. In some embodiments, a cutting tip 301 of the blade 300 cuts toward the closed footplate 420 but stops short of contacting the footplate due to a feature on the blade that abuts a corresponding feature on the shield 220 in order to prevent teeth of the cutting tip 301 from contacting the footplate 420 directly. In other embodiments, contact between the blade and footplate can be controlled in other ways, including by designing the length of longitudinal translation of the blade to make contact impossible, etc. In some embodiments, the blade 300 comprises a cutting tip 301 with any of a variety of toothed designs or a diamond grit blade, etc. In some embodiments, and as shown in more detail in FIG. 6B, the shield assembly 220 can include a feature attached to the support beam 430 that rests on or against an inside diameter of the crescentic blade to wipe off the inner diameter of the blade upon retraction of the blade proximally relative to the feature after a cut is made.

In operation, a drive assembly 100, to which the blade 300 is attached, can be moved distally with respect to a stationary assembly 200, to which the shield assembly 220 is attached, and this relative motion between the blade 300 and the shield assembly 220 can move the blade 300 though the cutting region 250. With the blade 300 being rotated or, as illustrated, oscillated, by a drive mechanism in the drive assembly 100, any tissue or bone present in the cutting region 250 can be contacted by the cutting tip 301 of the blade 300 and resected. In some embodiments, bone or tissue disposed in the cutting region 250 can be prevented from moving out of the path of the blade 300 contacting a proximal surface of the footplate 422.

The proximal surface of the footplate 422 can include a crescentic trough region 421 that forms an outer lip 422 and an inner lip 423. The outer lip 422 can extend to an outer peripheral edge 424 of the footplate such that the outer lip 422 can define a sharpness that is a function of the width of outer lip 422 at the peripheral edge 424 and the angle of the trough 421 as it approaches the peripheral edge 424. In operation, the cutting tip 301 of the blade 300 can approach the trough of the foot plate 421 and the outer lip 422 can engage with an outer edge of the cutting tip 301 in an overlapping jaw-like fashion, such that the fully extended position of the blade 300 locates the cutting tip 301 distally equal to or beyond the position of the outer lip 422 (while still allowing some separation between the blade tip 301 and the surface of the trough region 421). In some embodiments, the cutting tip 301 does not extend distally to the outer lip 422, but close enough to effectively cut tissue or bone therebetween. Similarly, the inner lip 423 engages with an inner edge of the cutting tip 301, such that the fully extended position of the blade 300 locates the cutting tip 301 distally equal to or beyond the position of the inner lip 423. In some embodiments, and as shown, the support beam 430 has a generally flat inner-facing surface and an outer edge 431 that has a width less than a corresponding inner cord section of the blade 300 to allow the blade to pass distally across the support beam 430. In some embodiments, this inner facing surface 432 is cupped or has an opening to increase the amount of material that is in the opening for resection.

FIG. 4B shows the full length of the elongated sleeve 221, from the opening 229 at the distal end to a proximal end configured to attach to the stationary assembly 200. Inside the elongated sleeve 221 is the blade shaft 310, showing the proximal edge extending beyond the elongated sleeve 221 to be coupled with the drive assembly 100 to actuate (e.g., oscillate) the blade 300. In operation, when the drive assembly 100 is moved distally, the blade shaft 310 is moved distally into the elongated sleeve 221 of the shield assembly 220. FIG. 4C shows the arrangement of the blade 300 around the support beam 430. In some embodiments, the proximal end 439 of the support beam 430 can be configured to abut a distal face of a proximal end of the blade (e.g., the opposite side of face 390 of FIG. 3A) when the blade reaches a designed maximum distal extension through the cutting region 250. This arrangement can prevent the cutting tip 301 of the blade 300 from contacting the footplate 420 by having the distal face of the blade contact the proximal end 439 of the support beam 430 before the cutting tip 301 contacts the footplate 420 and prevent further distal translation of the blade 300.

Figure 5:
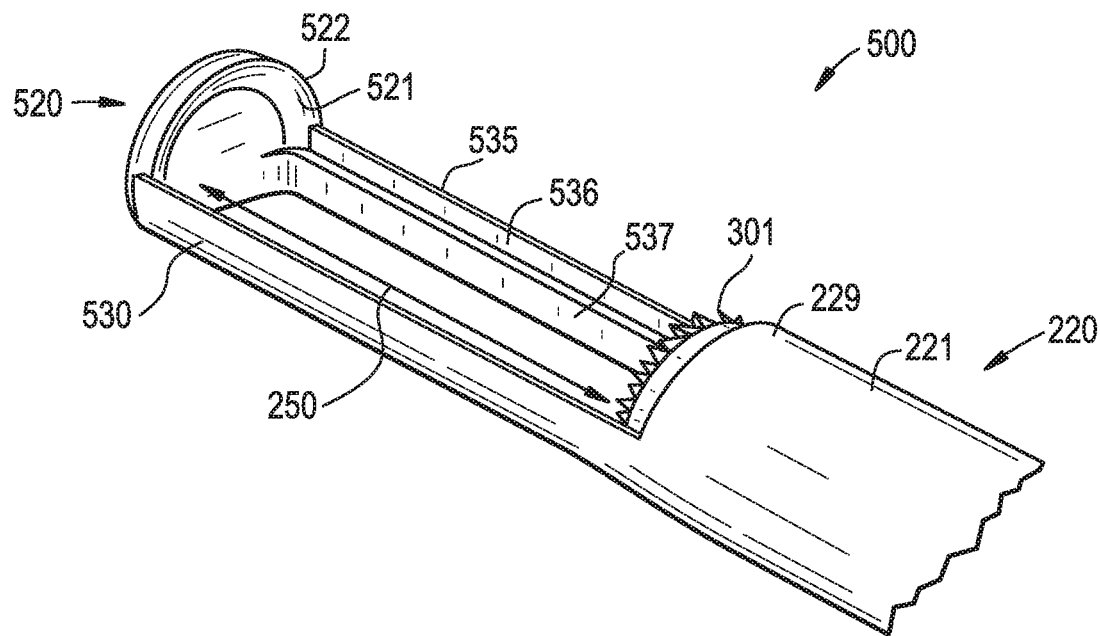
FIG. 5 is an illustration of another embodiment of a distal end of a drive assembly with a blade according to the present disclosure.
Figure 17A:
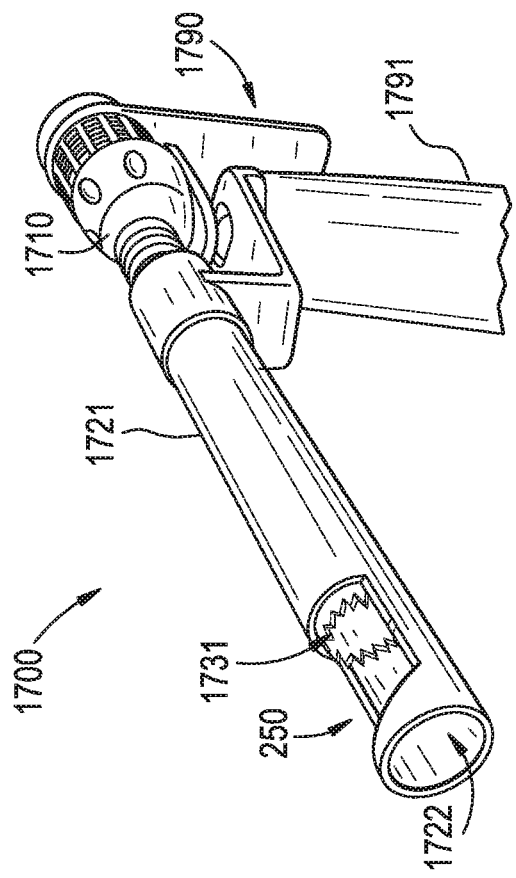
FIGS. 17A and 17B are illustrations of one embodiment of a bone and tissue resection device having a coring saw blade that rotates in a single direction.
Figure 17B:
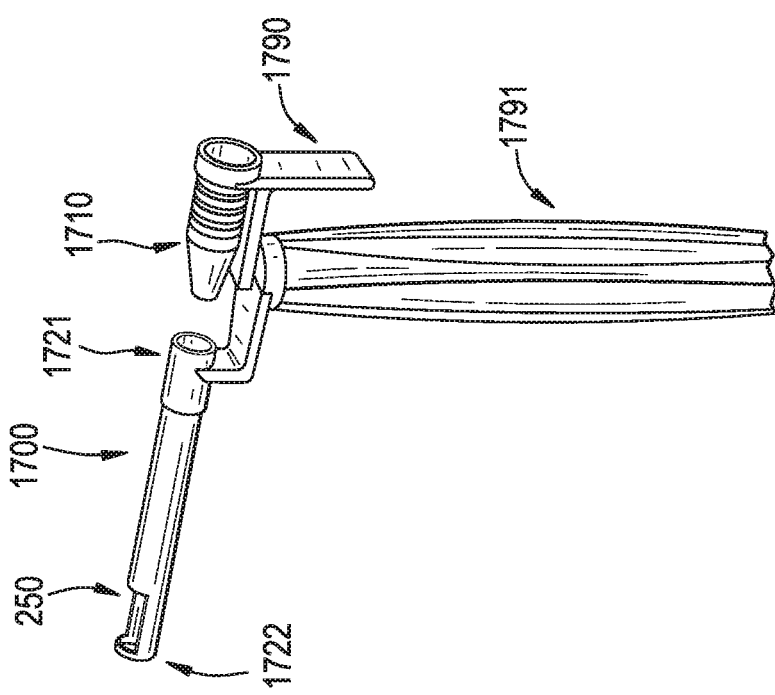

FIG. 5 is an illustration of another cutting assembly 500 according to aspects of the embodiments disclose herein. FIG. 5 shows the cutting assembly 500 includes the shield assembly 220 with an elongated tube 221 surrounding a blade 300 and a footplate 520 at a distal end of the shield assembly 220. The footplate 520 is connected to the distal end of the elongated tube 221 by two support beams 530. In some embodiments, the cutting assembly 500 includes only one support beam 530, however the use of two support beams can increase rigidity of the assembly and better resist deflection during use, etc. In some embodiments, a plate covers the opening created by the support beam(s) 530 to encapsulate the cutting region 250 allowing for tissue extraction after resection. The blade 300 can be nested inside the support beams 530 and configured to extend though the cutting region (indicated by arrow 250) during a cutting operation. The footplate 520 can include an outer lip 521 that extends to the peripheral edge 522 of the footplate to engage with the cutting tip 301 of the blade 300 as discussed above with respect to FIG. 4A. The footplate 520 can be totally closed or partially open. For example, an open footplate is shown in FIGS. 17A and 17B (e.g., open distal end 1722). The outer diameter of the support beams 530 are the same diameter as the elongated tube 221 in this embodiment.

In FIG. 5, the support beams 530 include an inner surface having a ridge 536 that marks a location where the support beam 530 transitions from a first sidewall thickness 535 to a second sidewall thickness 537 that is greater than the first thickness. More particularly, the support beam 530 can extend radially inward to achieve the second thickness 537 at points below the maximum angular reach of the oscillating blade 300 in order to add strength and stiffness to the support beams 530. Above the ridge 536, the support beam 530 can maintain the first sidewall thickness 536 that is configured to conform to or accommodate the outer diameter of the blade 300 as it passes through the cutting region 530. The support beams 530 rigidly locate the footplate 520 to enable the blade 300 to deliver a force to the tissue or bone in the cutting region 250 by pressing the tissue or bone against the footplate as the blade advances toward the footplate. Preventing deflection of the footplate 520 can enable the blade 300 to deliver a larger force to the tissue or bone and more successfully resect tissue.

Figure 6A:
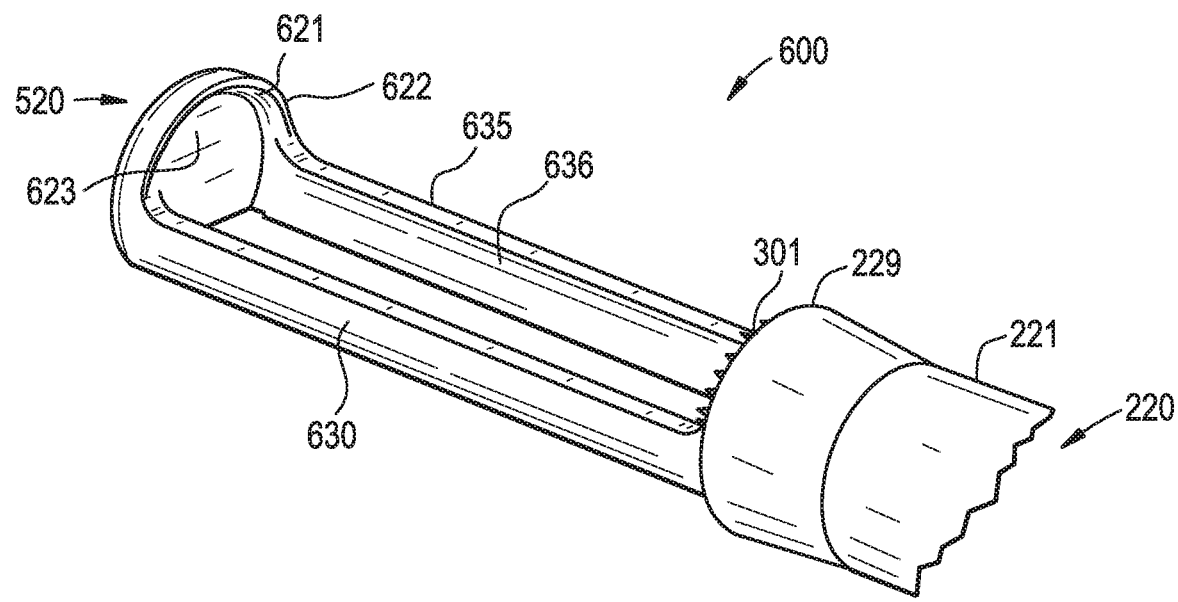
FIGS. 6A and 6B are illustrations of yet another embodiment of a distal end of a drive assembly with a blade according to the present disclosure.
Figure 6B:
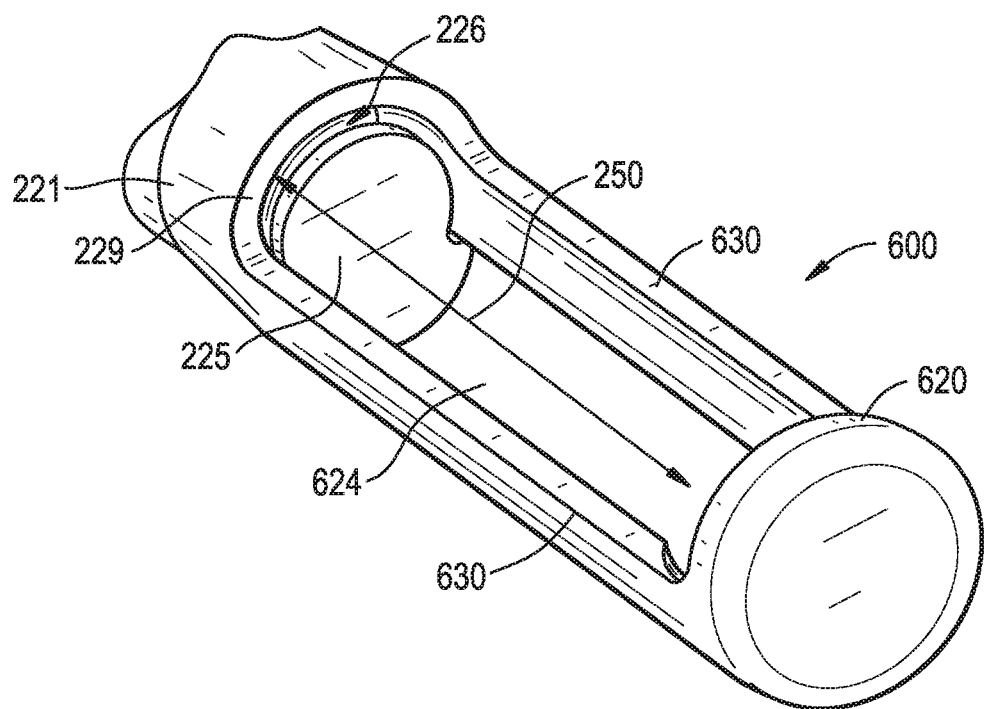

FIGS. 6A and 6B are illustrations of another embodiment of a cutting assembly 600 for use with a drive assembly 100 and stationary assembly 200 according to aspects of the embodiments disclosed herein. FIG. 6A shows a cutting assembly 600 that includes a shield assembly 220 and a footplate 620 connected to the distal end of the elongated sleeve 221 of the shield assembly 220 by two support beams 630. The support beams can include opposing inner faces 636 that are configured to allow the blade 300 to pass inside and along the inner faces 636 as the blade 300 moves through the cutting region 250. The support beams 630 can have a thickness 635 to provide the support beams 620 sufficient stiffness and strength to rigidly locate the footplate 620 with respect to the blade 300 during a cutting operation where the blade drives bone, for example, against the footplate 620 as the cutting tip 301 is advanced into the bone. The footplate 620 also includes a lip 621 that extends to a peripheral edge 622 of the footplate 620, similar to the embodiments described above. In some embodiments, the footplate can include an inner curved surface that curves proximally from a proximal face 623 of the footplate to the lip 621. The curved inner surface can be configured to allow the cutting tip 301 to move distally past the lip 621 without contacting proximal face 623 to improve the cutting action of the cutting tip 301. The outer diameter of the support beams 630 can be larger than the elongated tube 221, as shown in this embodiment.

FIG. 6B shows the cutting assembly 600 with the blade 300 removed to show that the cutting assembly includes a cleaning plate 225 in the opening 229 at the distal end of the elongated sleeve 221. The cleaning plate 225 and sidewall of the sleeve 221 define a crescentic opening 226 that the blade 300 passes through to enter the cutting region 250. The cleaning plate 225 therefor runs along the inner surface of the blade 300 and, as the blade is retracted proximally into the elongated sleeve 221, for example by the biasing force of the spring 270 moving the drive assembly proximally, the cleaning plate 225 can remove any resected tissue or debris attached to the blade 300 after a cutting stroke through the cutting region 250. In some embodiments, the improved cutting action of the oscillating blade 300 can cleanly resect a mass of tissue without pulverizing, fragmenting, or otherwise breaking it into several smaller pieces. In such embodiments, the cleaning plate 225 can serve to retain the resected mass of tissue between the cleaning plate and the footplate 620 as the blade 300 is retracted proximally. A grasping surgical instrument can then be used to remove the resected mass (e.g., through the window 624) and clear the cutting region 250 for another use. In other embodiments, the resected mass can be cleared using a suction instrument rather than a grasper, while in still other embodiments the instrument can simply be positioned for another use and movement of new tissue into the cutting region 624 can eject the resected tissue mass through the window 624. The outer diameter of the support beams 630 can be larger than the elongated tube 221, as shown in this embodiment.

In some embodiments, any of the various cutting assemblies or distal end assemblies described above can include one or more sensors to aid in positioning the instrument at a surgical site. For example, one or more sensors can be positioned along the footplate, blade, shield sleeve, or support arms to detect proximity to one or more anatomical structures, such as nerves, blood vessels, etc. Any of a variety of known sensors can be employed, including optical sensors, electromagnetic sensors (e.g., electrodes), pressure sensors, etc. Such sensors can be disposed along an exterior surface of the device or integrated into the device. In addition, embodiments formed from materials not readily visible in a particular type of medical imaging, e.g., fluoroscopy, etc. can include one or more markers attached thereto or embedded throughout made from a material visible with such imaging.

Example Drive Assembly Actuation

The following figures illustrate different configurations for the actuation of the drive assembly 100 with respect to the stationary assembly 200.

Figure 7B:
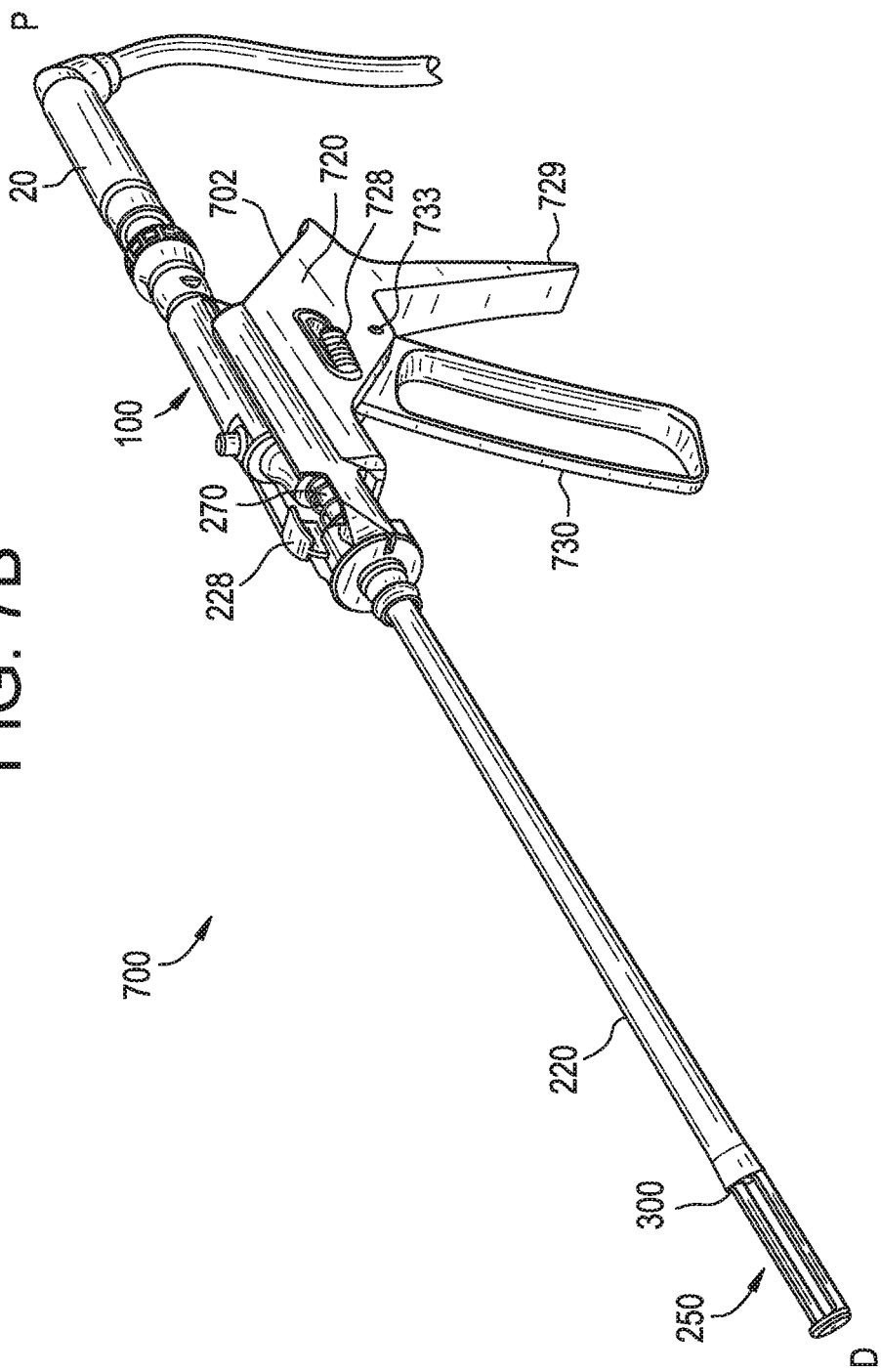

FIGS. 7A-7C are illustrations of one embodiment of a bone and tissue resection device 700 having a pivoting trigger 730 configured to actuate the movement of the drive assembly 100. FIG. 7A illustrates a bone and tissue resection device 700 having a stationary assembly 702 with a pistol grip handle 729 connected to a frame 720 and a pivoting trigger 730 configured pivot about an axis 733 and push the drive assembly 100 distally.

In operation, the pivoting trigger 730 can be moved (indicated by arrow 799) from an extended position 731*b* until a lever arm 732 of the pivoting trigger 730 contacts the drive assembly 100 (e.g., at a proximal lip 734, see FIG. 7C) directly or indirectly so that pulling the pivoting trigger 730 further advances the drive assembly 100 and the blade shaft shield 120 distally against the biasing force of a spring 270. The movement 799 can drive the blade (not shown, e.g., blade 300 described above) into the cutting region 250 in the shield assembly 220. The pivoting trigger 730 can be moved to a fully retracted position 731*a* where the drive assembly 100 is advanced distally as far as possible. In some embodiments, a stop mechanism in the shield assembly 220 can contact the blade 300 to prevent further distal movement of the drive assembly. A sliding or stationary stop block 728 can also prevent the trigger from overextending in the "locked" position (as shown). Sliding the stop block 728 to the "unlocked" position (indicated by arrow 797) can push the pivoting trigger 730 out of contact with the drive assembly 100, allowing the drive assembly 100 to be removed or inserted into the housing 720 of the stationary assembly 702. After inserting the drive assembly 100 into the stationary assembly 720, pulling the pivoting trigger 730 can push the stop block 728 back into the "locked" position. A spring 729 can be mounted in the frame 720 and can push on the drive assembly, taking up tolerances and reducing rattle between moving parts, for example, the drive assembly 101 and the frame 720. FIG. 7B is a perspective view of the bone and tissue resection device 700. FIG. 7C is a detail view of the bone and tissue resection device 700, where the stationary assembly 702 is translucent, showing the engagement of the pivoting trigger 730 with the drive assembly 100.

FIG. 8 is an illustration of another embodiment of a bone and tissue resection device 800 having an alternative grip and trigger arrangement. In particular, the embodiment of FIG. 8 includes a proximal handle 829 attached to the drive assembly 100 and a trigger 830 attached to a frame 820 of a stationary assembly 802. In operation, the handle 829 and trigger 830 can be squeezed together by a user's hand, thereby advancing the drive assembly 100 distally (e.g., against biasing force from spring 270 not visible in FIG. 8) to advance the blade 300 within the cutting region 250 toward the footplate 222. FIG. 8 shows the handle 829 and trigger 830 in their fully compressed position, wherein the blade 300 is advanced distally through the cutting region 250. Releasing the compression between handle 829 and trigger 830 from this position can allow a biasing force (e.g., from spring 270 not visible in FIG. 8) to withdraw the drive assembly 100 proximally with respect to the frame 820 and trigger 830, thereby withdrawing the blade 300 proximally through the cutting region and into the shield assembly 220.

Figure 9B:
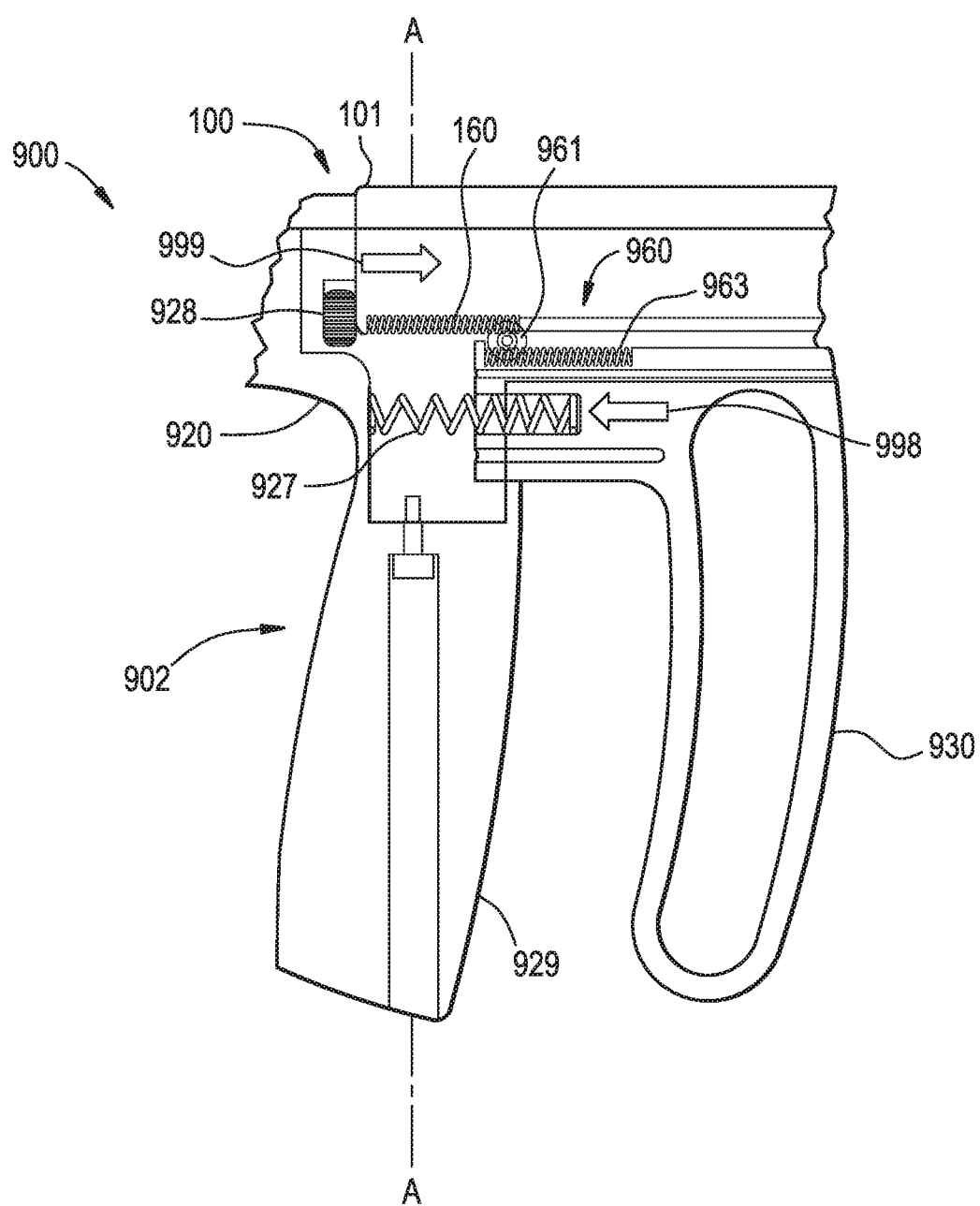

FIG. 9A-9D are illustrations of one embodiment of a bone and tissue resection device 900 having a rack and pinion that control movement between a stationary assembly 902 and a drive assembly 100. FIG. 9A shows a stationary assembly 902 that includes a frame 920 having a handle 929 and a trigger 930 that is slidably coupled to the frame 920. The trigger 930 can translate or slide proximally and distally with regard to the handle 929. An opposing rack-and-pinion mechanism 960 is configured to move the drive assembly 100 distally when pulling the trigger 930 proximally toward the handle 929 by interaction of one rack 963 on the trigger 930, one rack 160 on the drive assembly 100, and a pinion or gear 961 positioned between them and rotatably mounted to the frame 920, as shown in more detail in FIG. 9B. In some embodiments, two pinions 961, 961' can be utilized and can be spring-loaded or otherwise biased toward one other to engage two angled racks, as shown in more detail in FIGS. 9C and 9D. Biasing the pinions 961, 961' in this manner can help maximizes engagement with the racks and takes up tolerances, thereby reducing rattle between the various moving parts in the device 900.

FIG. 9B shows the rack and pinion mechanism 960 between the trigger 930 and the drive assembly 100 in greater detail. The stationary assembly 902 can include a spring 927 biasing the trigger 930 away from the handle 929. The rack and pinion mechanism 960 can include a bottom rack 963 on the trigger positioned below the housing 101 of the drive assembly, a top rack 160 on the housing 101 of the drive assembly 100 positioned above the bottom rack 963, and a pinion 961 positioned between the top rack 160 and the bottom rack 963. In operation, the trigger 930 can be driven proximally (as indicated by arrow 998) by the fingers of a user's hand squeezing together the handle 929 and trigger 930. As the trigger 930 translates proximally relative to the handle 929, the rack 963 also translates proximally. The pinion 961, which is coupled to the frame 920, rotates and causes the rack 160 to translate the drive assembly 100 distally (indicated by arrow 999). FIG. 9B also shows the drive assembly 100 secured in place by a latch mechanism 928, which is shown in more detail in FIGS. 10E and 10D.

Figure 9C:
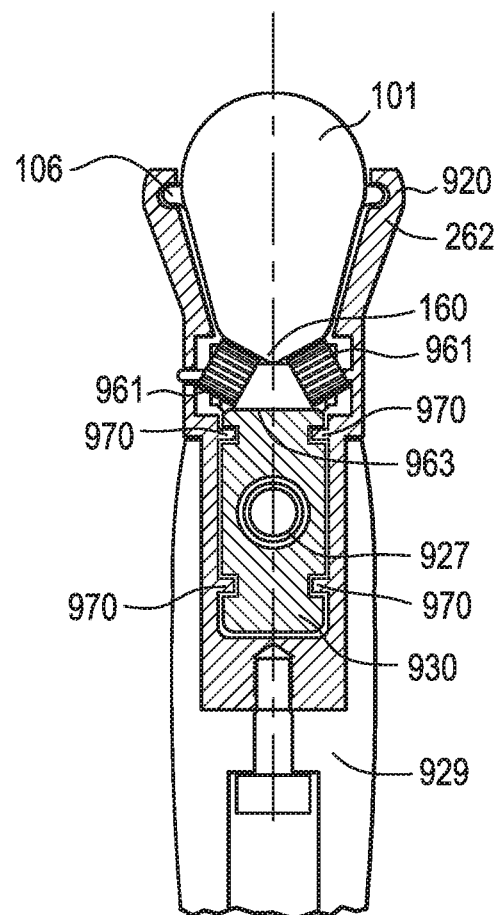
Figure 9D:
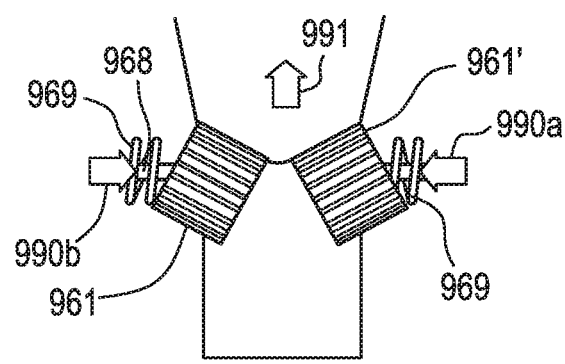

FIG. 9C is a cross-sectional view of the bone and tissue resection device 900 taken along the line A-A in FIG. 9B, showing one exemplary geometry of a rack and pinion mechanism 960. FIG. 9C shows the bottom rack 963 and top rack 160 each comprising two parallel racks, with a corresponding set of opposed tapered pinions 961, 961' between them. As shown in FIG. 9D, the pinions 961 are spring-loaded to be biased towards each other by springs 969. FIG. 9D shows two pinions 960 disposed along a common axis 968 between the trigger 930 and the housing 101 of the drive assembly 100. Each pinion 961 includes a spring 969 biasing the pinion 961 toward a midline of the device or toward the other pinion. The biasing force of the springs 969 (shown as arrows 990a, 990b) can apply an opposing force (shown as arrow 991) onto the trigger 930 and housing 101. These opposing force 991 can urge the housing 101 upward and the trigger 930 downward, which can press the guide protrusions 106 of the housing 101 and the protrusions 970 of the handle 920 into corresponding guide channels 262 and 970, respectively. By biasing these elements together, tolerances can be taken up and rattle created by the device during operation (e.g., when the components are vibrating due to the oscillating blade) can be minimized. These forces can also help maintain the coupling of the pinions 961, 961' to the racks 160, 963.

FIG. 9E-9G are illustrations of another embodiment of a bone and tissue resection device 900' having a handle 920' and a trigger 930' that fits into one or more grooves 931 formed therein that slide along one or more rails 970' formed in a frame 920' of the stationary assembly 902'. The device 900' can function similarly to the device 900 described above. FIG. 9F is a perspective view of the trigger 930' and its relation to the frame 920'. FIG. 9G is a cross-sectional view (taken along plane B of FIG. 9E) showing the trigger 930' coupled to the frame 920' via a pair of opposed protrusions or rails 970' of the frame 930'.

Figure 10A:
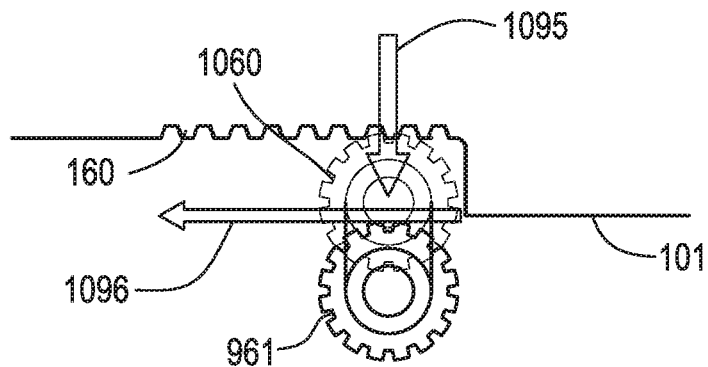
FIGS. 10A-10E are illustrations of different embodiments of engagement systems for removably coupling a drive assembly to a stationary assembly.
Figure 10B:
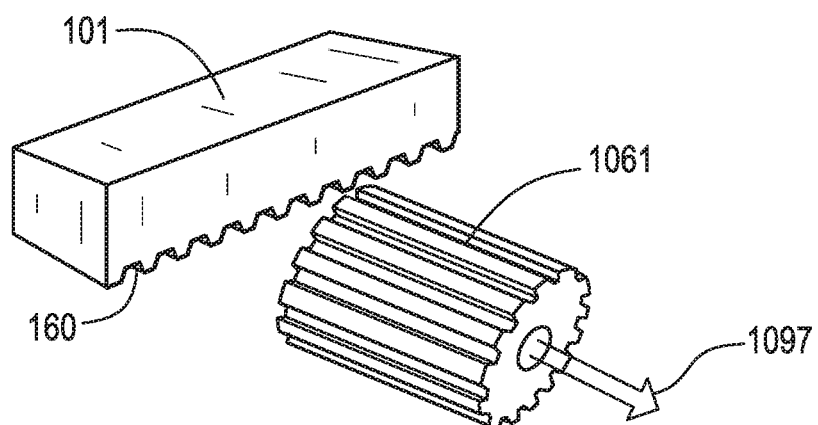
Figure 10C:
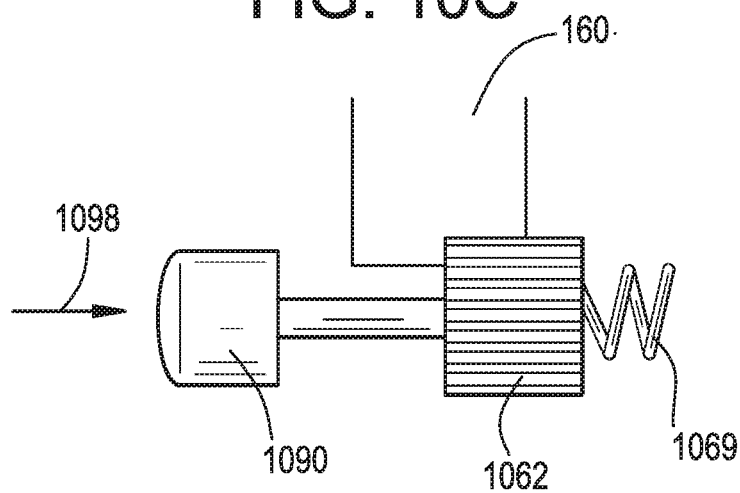

FIGS. 10A-10E are illustrations of different embodiments of engagement systems for removably coupling a drive assembly to a stationary assembly. FIG. 10A shows a rack and pinion system for releasably coupling a drive assembly 100 to a stationary assembly 902. The pinion 961 can be capable of translation (indicated by arrow 1095) from a first, locked position 1060, where the pinion 961 is engaged with the top rack 106 of the housing 101 of the drive assembly, to a second, release position where the pinion 961 is disposed below the housing 101 and clear of the rack 160 to enable the housing 101 to be inserted or removed from the frame 920 of the stationary assembly 920. FIG. 10B shows an alternative pinion release mechanism, where a straight pinion 1061 can be translated laterally (as indicated by arrow 1097) to disengage from the rack 160, thereby freeing the top rack 160 and allowing the housing 101 to be decoupled from the frame 920. FIG. 10C shows yet another embodiment of a pinion release mechanism, wherein a pinion 1062 can be biased with a spring 1069 against the top rack 160 of the housing 101. To decouple the housing 101 from the stationary assembly 920, a release button 1090 can be depressed (indicated by arrow 1098) to translate the pinion 1062 laterally against the bias of the spring 1069. This translation can disengage the pinion 1062 from the rack 160 and clear a path for the rack 160 (and housing 101 of the drive assembly) to be translated proximally for decoupling from the stationary assembly 902.

Figure 10D:
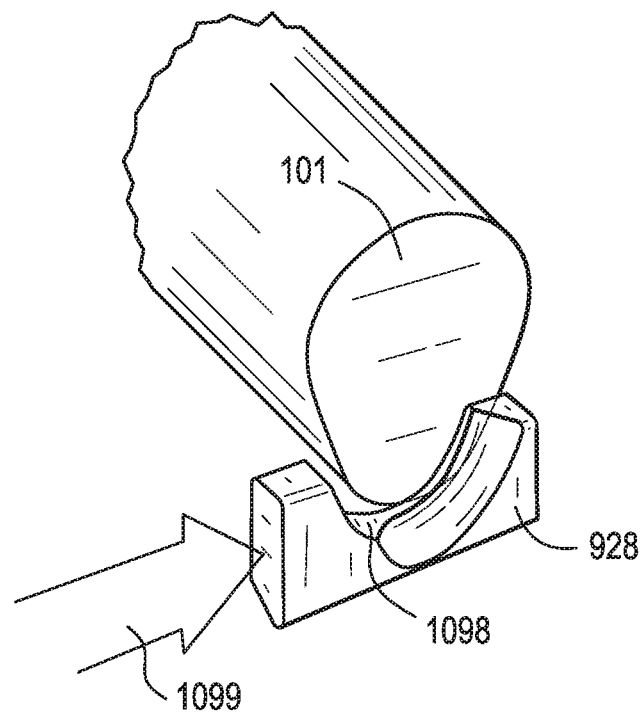
Figure 10E:
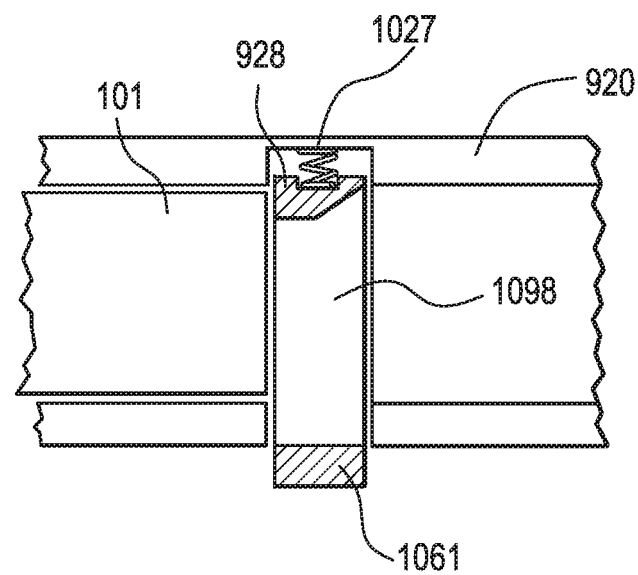

FIG. 10D illustrates operation of one embodiment of the latch 928 shown in FIG. 9B that can selectively prevent decoupling of the housing 101 relative to the frame 920. In operation, the housing 101 can be translated distally relative to the frame 920 until a proximal end thereof, or another proximal-facing surface or other surface feature thereof, contacts the latch mechanism 928 and deflects latch mechanism 928 laterally (in the direction of arrow 1099) to allow the housing 101 to pass into the channel of the frame 920. Once the housing 101 is advanced distally a sufficient amount, the latch 928 can move opposite the arrow 1099 in FIG. 10D to the position shown in the perspective view of FIG. 10D and the top view of FIG. 10E wherein a portion of the latch 928 interferes with proximal translation of the housing 101 along the channel in the frame 920 beyond the position of the latch. To decouple the housing 101 from the frame 920, the latch 928 can be moved in the direction of arrow 1099 until, for example, a channel 1098 formed in the latch aligns with the channel of the frame 920 along which the housing 101 translates. In some embodiments, and as shown in FIG. 10E, the latch 928 can include a spring 1027 that is either separate from or built into the latch 928 that biases the latch 928 in the locked position, as shown in FIGS. 10D and 10E, where the housing 101 is unable to move proximally in the frame 920 past the latch 928.

Example Longitudinally Extending Trigger Configurations

Figure 11B:
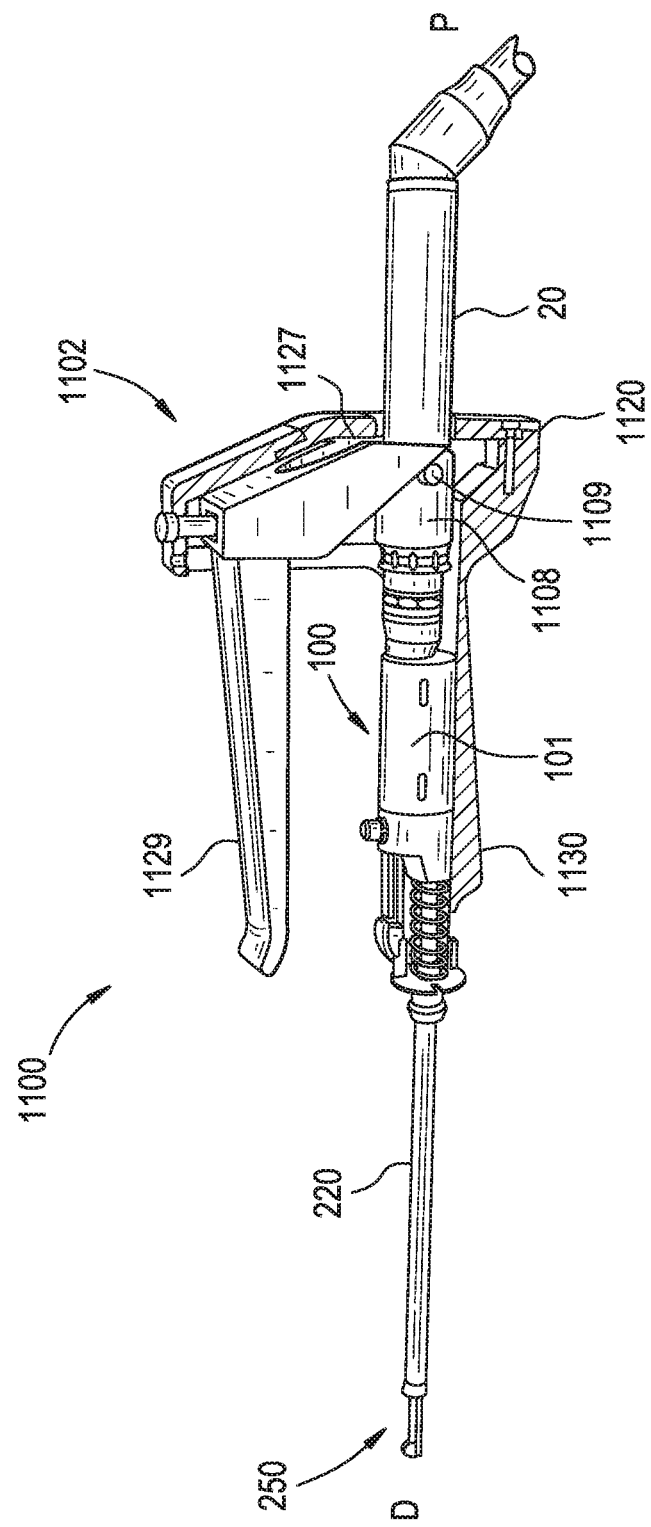

FIGS. 11A-11C are illustrations of one embodiment of a bone and tissue resection device 1100 having a longitudinally extending handle and trigger arrangement. Such embodiments include alternative handles for the powered cutting systems disclosed herein wherein the handle or trigger is arranged to extend longitudinally along the device. These embodiments can allow for pistol-grip or trigger-like actuation while holding the device 1100 in a vertical or near-vertical orientation without the need to bend and twist the wrist and arm.

FIG. 11A shows the bone and tissue resection device 1100 having a stationary assembly 1102 and a drive assembly 100 slidably coupled with the stationary assembly 1102. The stationary assembly includes a longitudinally extending trigger 1129 positioned above the drive assembly 100 and a grip 1130 integrated into a frame 1120 disposed around the drive assembly 100. In operation, and as shown in more detail in FIG. 11B, when the longitudinally extending trigger 1129 is moved towards the grip 1130, a wedge integrated into the trigger 1129 can contact a roller pin 1109 coupled to the drive assembly 100, thereby advancing the drive assembly 100 distally.

FIGS. 11B and 11C illustrate the inside of the frame 1120 of the stationary assembly, where the wedge 1127 of the vertical trigger 1129 is shown contacting the roller pin 1109 of an actuation sleeve 1108 coupled to the drive assembly 100. In operation, when the trigger 1129 moves towards the drive assembly 100 (as shown by arrow 1198 in FIG. 11C), the roller pin 1109 is driven along the face 1128 of the wedge 1127, thereby causing the sleeve 1108 and drive assembly 100 to advance distally against the biasing force of the spring 270. As described above, this distal advancement of the drive assembly 100 also advances the blade 300 along the cutting region 250 to conduct a cutting stroke and resect tissue.

Example Oscillator Mechanisms

Figure 12D:
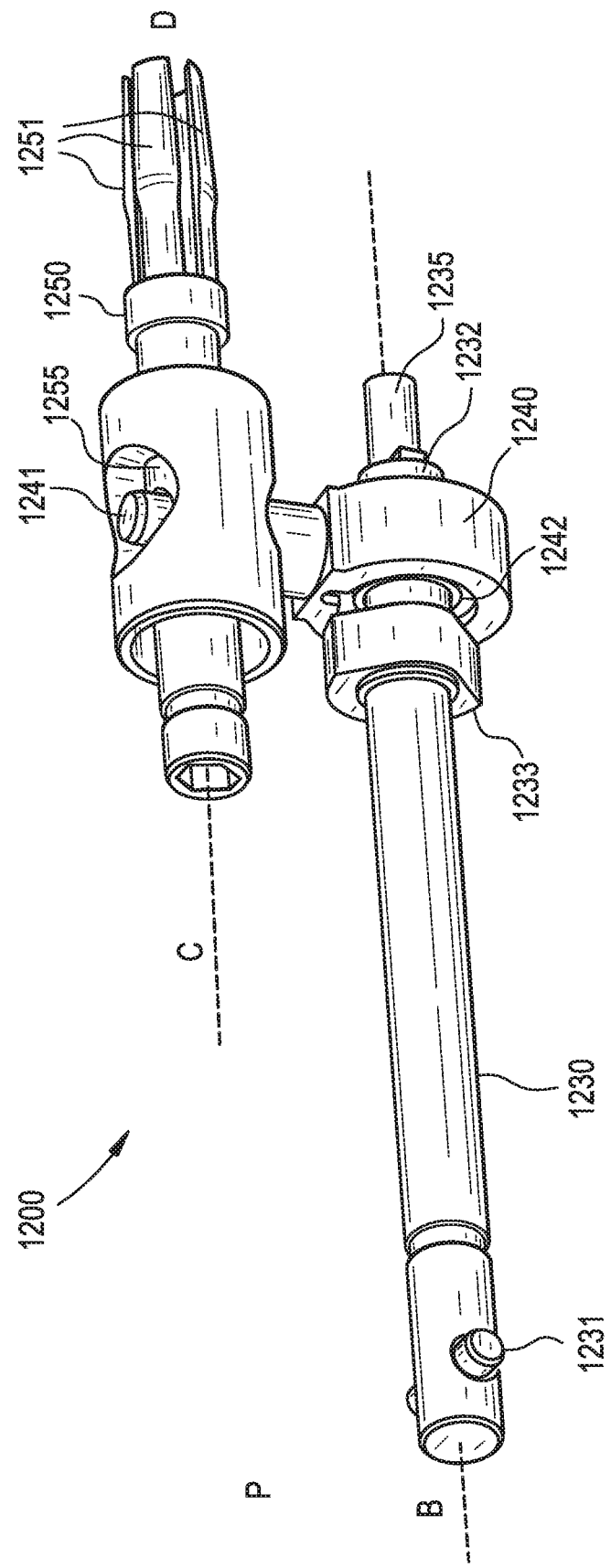
Figure 12E:
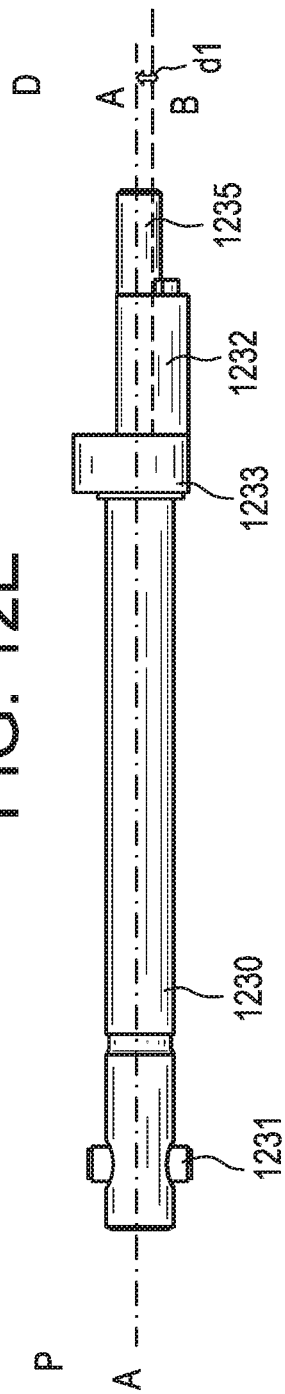

FIGS. 12A-12H are illustrations of a drive assembly having a piston oscillator mechanism. FIG. 12A shows an oscillator drive assembly 1200 having a housing 1201 that contains a piston oscillator mechanism, a blade shaft shield 120 extending distally from the housing 1201, an input shaft 1230 to the piston oscillator mechanism extending proximally from the housing 101, and a button release 181 for the blade shaft 310 (not shown in FIG. 12A). The input shaft 1230 can include a coupling element 1231 to be engaged by a corresponding element of a motor 20 to enable the motor 20 to spin the input shaft 1230. In operation, the piston oscillator mechanism converts the input rotational motion of the input shaft 1230 into an oscillating motion of an output shaft coupled to the blade shaft 310, as shown in FIGS. 12B-12H.

FIG. 12B shows the components of the oscillator drive assembly 1200 without the housing 1201. The oscillator drive assembly 1210 includes the input shaft 1230, an output shaft 1250, and a piston oscillator mechanism coupling the input shaft 1230 to the output shaft 1250, as explained in more detail below. The input shaft 1230 can rotate freely inside a plurality of bearings 1239, bushings, or directly against the housing 1201 to secure the input shaft 1230 in the housing 1201. The input shaft 1230 includes a cylindrical eccentric section 1232 that has a central axis B offset from, and parallel to, the central axis A of the input shaft 1230 (see d1 of FIG. 12E). The input shaft 1230 can also include a counterweight 1233 that counterbalances the eccentrically rotating components coupled to the eccentric section 1232 to reduce or prevent excessive vibration from rotation of the input shaft.

The output shaft 1250 can also rotate freely inside a plurality of bearings 1259, bushing, or directly against the housing 1201 to secure the output shaft 1250 in the housing 1201. The output shaft 1250 can be directly coupled to the blade shaft 310, or drive a blade coupling to transmit the oscillating torque to the blade shaft 310 indirectly. This embodiment includes a plurality of collet arms 1251 that define a central recess to accept a proximal end of a blade shaft 310 (not shown). A retainer 1281 is slidably disposed around the collet arms 1251 and configured to selectively lock the blade shaft (not shown) relative to the output shaft 1250 as the retainer 1281 translates relative to the output shaft 1250 collapsing the collet arms 1251 towards the blade shaft 310. The retainer 1281 can include an angled face 1283 that can interface with a corresponding angled face 1284 of a wedge 1280 extending towards the retainer. The wedge 1280 can be moved radially toward or away from the output shaft by actuation of the button release 181. Accordingly, in use, a user can depress the button 181 (i.e., move it in the upward direction of FIG. 12B) to advance the wedge 1284 radially toward or away from the output shaft 1250. This movement of the wedge 1284 can cause the retainer 1281 to translate away from the wedging surface of the collet arms 1251. As the retainer 1281 translates, it moves along a portion of the collet arms 1251 having a tapered diameter such that the retainer exerts less compressive pressure on the collet arms 1251. In this state a user can insert or remove a proximal end of a blade shaft 310 due to the reduced grip of the collet arms 1251. Upon release of the button 181, the wedge 1280 can move radially away from the output shaft 1250, resulting in the translation of the retainer 1281 towards the wedging surface of the collet arms 1251 that can urge the collet arms 1251 against any blade shaft disposed therebetween. This can lock the blade shaft, if present, to the output shaft 1250.

Turning to the piston oscillator mechanism that couples the input shaft 1230 to the output shaft 1250, FIG. 12B shows a connector 1240 disposed concentrically around a bearing 1242 (see FIG. 12D) that is disposed around the eccentric section 1232 of the input shaft 1230. The output shaft 1250 has a stationary pin 1241 either integrated into the output shaft 1250 or as a separate component extending therefrom into a bore 1255 formed in the output shaft. In operation, rotation of the input shaft 1230 can spin a central axis A (see FIG. 12E) of the eccentric section 1232 about the central axis B (see FIG. 12E) of the input shaft 1230, which is offset from the central axis of the eccentric section 1232 by a distance $d_1$ (see FIG. 12E). The eccentric rotation of the connector 1240 driven by the eccentric section 1232 moves the connector over the pin 1241 with respect to a central axis C of the output shaft 1250 (see FIG. 12B) in a manner similar to a piston connector rod being moved up and down by a crankshaft in an internal combustion engine. As the input shaft 1230 rotates, the angular position of the central axis B of the eccentric section 1232 of the input shaft moves relative to the central axis C of the output shaft 1250 creating an oscillation about the central axis C. Repeated rotations of the input shaft 1230 therefore cause repeated oscillating movement of the output shaft 1250 about its central axis C. The range of the oscillating motion is shown in more detail in FIGS. 12G and 12H, which provide an end-view of the shafts 1230, 1250 and connector 1240. In some embodiments, the pin 1241 can be integral to the connector 1240, and the output shaft 1250 will feature a bore for the pin 1241 to move within to create the oscillation.

Figure 12F:
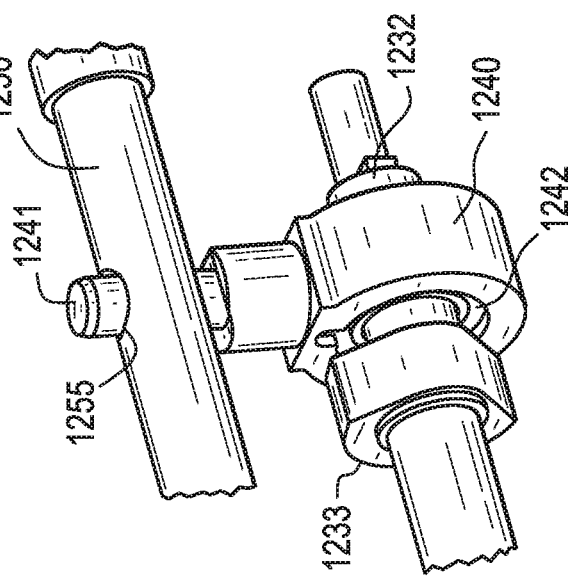

FIG. 12C shows a detail view of the input shaft 1230, output shaft 1250, connector 1240, and spacer 1258. Note that in the perspectives of each of FIGS. 12B and 12C, the input shaft is rotationally orientated such that the central axis B of the input shaft 1230 (see FIG. 12E) is aligned with the central axis A of the eccentric section 1232 (see FIG. 12E). FIG. 12D is a perspective view of the components shown in FIG. 12C. Visible in the perspective view is the bearing 1242 disposed inside the connector 1240 that allows the eccentric section 1232 to spin inside the connector 1240. In some cases, the bearing 1242 can be a bushing, or the connector can be directly contacting the eccentric section 1232. FIG. 12D also shows the pin 1241 extending from the bore 1255 in the output shaft 1250. In some embodiments, and as shown, the bore 1255 is a hole through the output shaft 1250 that is orthogonal to the output shaft's axis of rotation C. FIG. 12F is a detail view without the spacer 1258.

FIGS. 12G and 12H illustrate the conversion of rotational motion of the input shaft 1230 into oscillating motion of the output shaft 1250. FIGS. 12G and 12H each show the piston oscillator mechanism in a view orthogonal to the central axes B, C of the input shaft 1230 and the output shaft 1250, respectively. Horizontal (H) and vertical (V) axes are labeled in both figures (though these terms are relative, as rotating the instrument can reorient which axis is vertical vs. horizontal), and the intersection of the horizontal and vertical axes is placed at the central axis of rotation B of the input shaft 1230. Also shown in the figure is the central axis A of the eccentric section 1232. The intersection of the vertical axis with a second horizontal axis 1299 is the central axis C of the output shaft 1250. In operation, the input shaft 1230 spins, clockwise or counterclockwise, and the output shaft 1250 oscillates clockwise and counterclockwise between the positions shown in FIG. 12G and FIG. 12H. The difference between these positions therefore represents the range of oscillation of the output shaft 1250.

In FIG. 12G, the eccentric section 1232 is maximally extended in a first horizontal direction (e.g., to the left with respect to FIG. 12G) and the pin 1241 has rotated the output shaft 1250 clockwise by an angle represented by the angular relation of a reference line 1281 with respect to the second horizontal axis 1299. The reference line 1281 is chosen to be perpendicular with the second horizontal axis 1299 when the eccentric section 1232 is maximally extended in either vertical direction (e.g., up or down with respect to FIG. 12G). The angular difference between line 1299 and 1281 in FIG. 12G is a maximum clockwise the rotation of the output shaft 1250 induced by the rotation of the eccentric section 1232 about which the connector 1240 is disposed.

FIG. 12H illustrates the eccentric section 1232 maximally extended in a second horizontal direction (e.g., to the right with respect to FIG. 12G) opposite the first direction shown in FIG. 12G. In FIG. 12H, the pin 1241 has rotated the output shaft 1250 counterclockwise by an angle represented by the angular relation of the reference line 1281 with respect to the second horizontal axis 1299. The angular difference between line 1299 and 1281 in FIG. 12H is maximum counterclockwise the rotation of the output shaft 1250 induced by the rotation of the eccentric section 1232 about which the connector 1240 is disposed.

The angular range of oscillation shown in FIGS. 12G and 12H can be adjusted by, for example, adjusting various geometric parameters of the assembly. For example, adjusting the eccentric section to increase or decrease the distance di between the central axis B of the input shaft 1230 and the central axis A of the eccentric section 1232 can adjust the angular range of oscillation. Similarly, adjusting a distance between input and output shafts 1230, 1250, respectively, can influence the angular range of oscillation. Generally speaking, the above-described configuration can be well suited to applications that require a smaller angular range of oscillation at a higher rate of oscillation. By way of example only, the total angular range of oscillation shown in FIGS. 12G and 12H can be less than about 10° in some embodiments. In some embodiments, the total angular range can be about 7°.

The piston oscillator mechanism of FIGS. 12A-12H has a number of advantages over known oscillators. For example, the piston oscillator mechanism can convert high input RPMs (revolutions per minute) into high output OPMs (oscillations per minute) due to low friction and backlash generated during the movements of the piston oscillator mechanism. For example, the input shaft 1230 can be counter balanced such that rotation of the connector 1240 and pin 1241 generate minimal vibration, and the movement of the pin 1241 in the bore 1255 is the only point of contact between moving parts outside of the bearings. In some embodiments, the pin and/or the bore 1255 can be made formed of, or coated with, a material having low friction, or the pin 1241 and/or the bore 1255 can be lubricated to further reduce friction. Further, in some embodiments, the bore 1255 can be lined with a sleeve or insert that can aid in reducing frictional forces. Exemplary rotation and oscillation rates can be quite high, e.g., as high as about 80,000 OPM in some embodiments. Operating at such high oscillation rates can enable superior cutting performance from the blade 300 or other instrument coupled to the output shaft 1250.

Figure 13A:
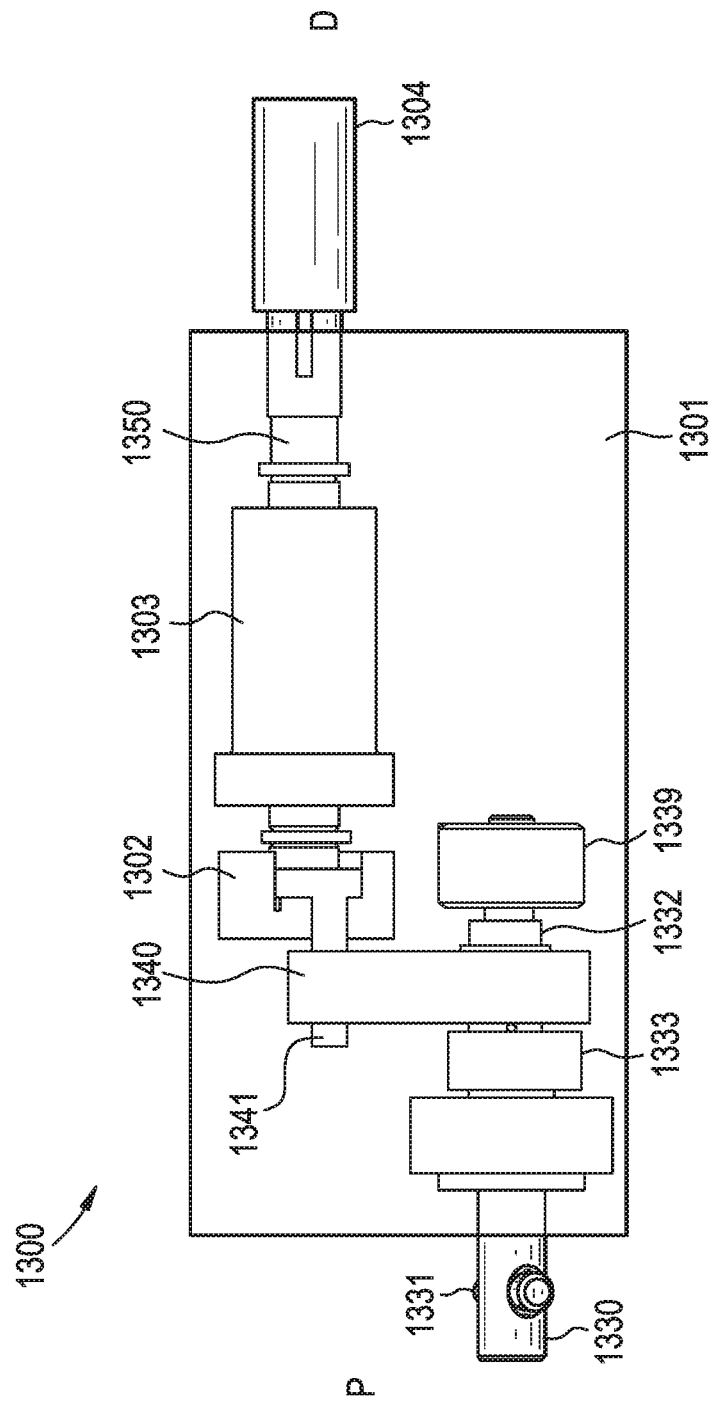

FIGS. 13A-13F are illustrations of an oscillator drive assembly 1300 having a four bar linkage oscillator. FIG. 13A shows the oscillator drive assembly 1300 with a housing 1301 that contains that an input shaft 1330, an output shaft 1350, and a four bar linkage oscillator that connects the input shaft 1330 to the output shaft 1350. The input shaft 1330 extends proximally from the housing 1301 of the drive assembly 1300 with a coupling element 1331 that can be engaged by a corresponding element of a motor 20 (not shown) to enable the motor 20 to spin the input shaft 1330. The output shaft 1350 can be configured to couple with a blade shaft 310 (not shown) such that oscillations of the output shaft 1350 are transferred to the blade shaft 310. The four-bar linkage oscillator can couple an offset or eccentric section of the continuously spinning input shaft 1330 to the output shaft 1350 by means of a linkage 1340. The input shaft 1330 can be rotatably secured in the housing 1301 by bearings 1339, bushings, or directly contacting the housing and can include an eccentric section 1332 with a counterweight 1333. Further, the output shaft 1350 can include collet arms 1355 disposed at a distal end thereof, as well as a translating retainer 1304 that can selectively lock a blade or other instrument shaft between the collet arms 1355 in a manner similar to the retainer 1281 described above. In some embodiments, the output shaft 1350 can be directly coupled to the blade shaft 310. In some embodiments, the output shaft 1350 can be indirectly coupled to the blade shaft 310 through means of a temporary mechanical, or magnetic connection. In some embodiments, the offset pin 1341 can be directly coupled to, or part of the blade shaft 310 to minimize reciprocating mass.

Figure 13B:
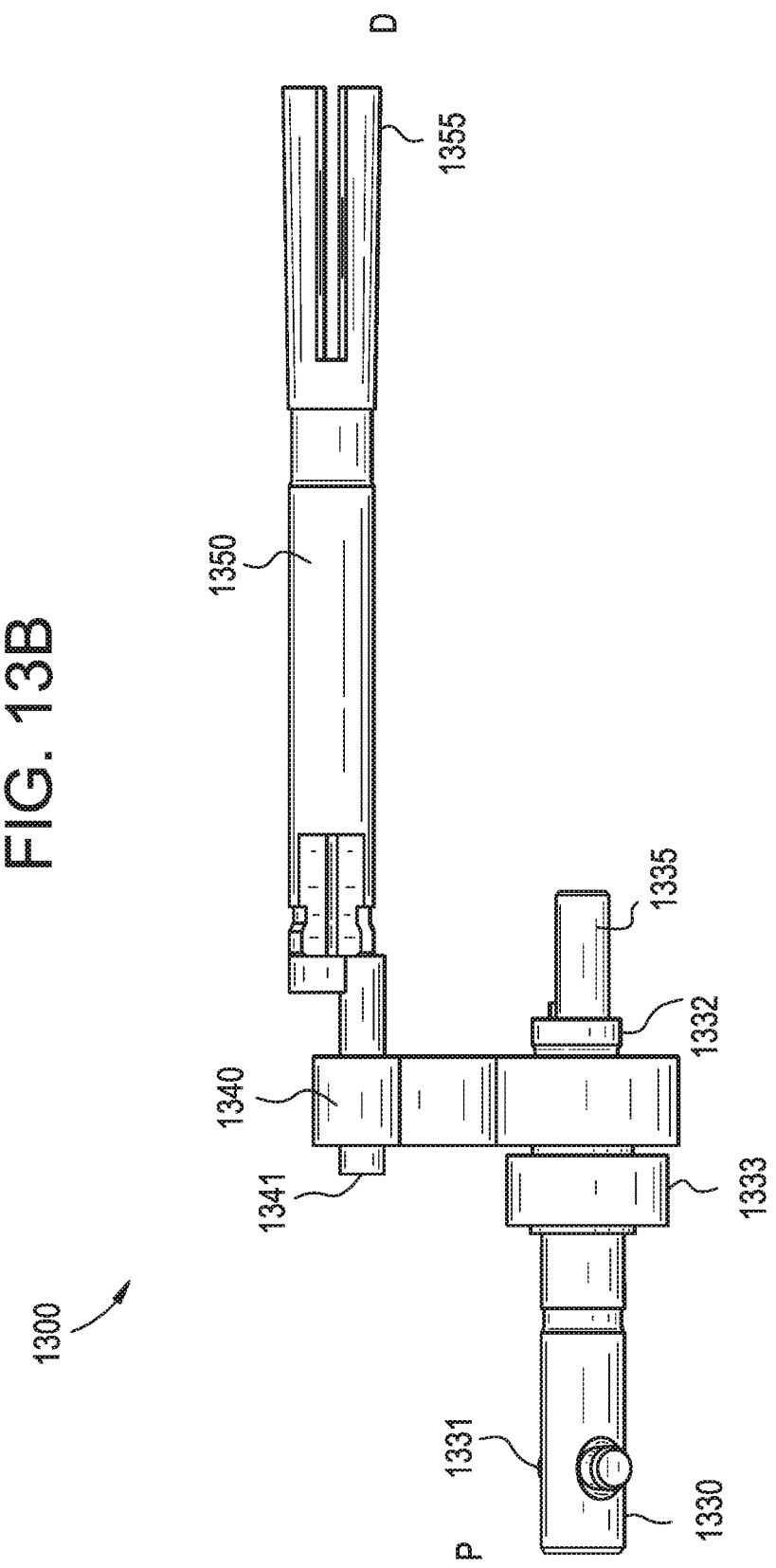
Figure 13C:
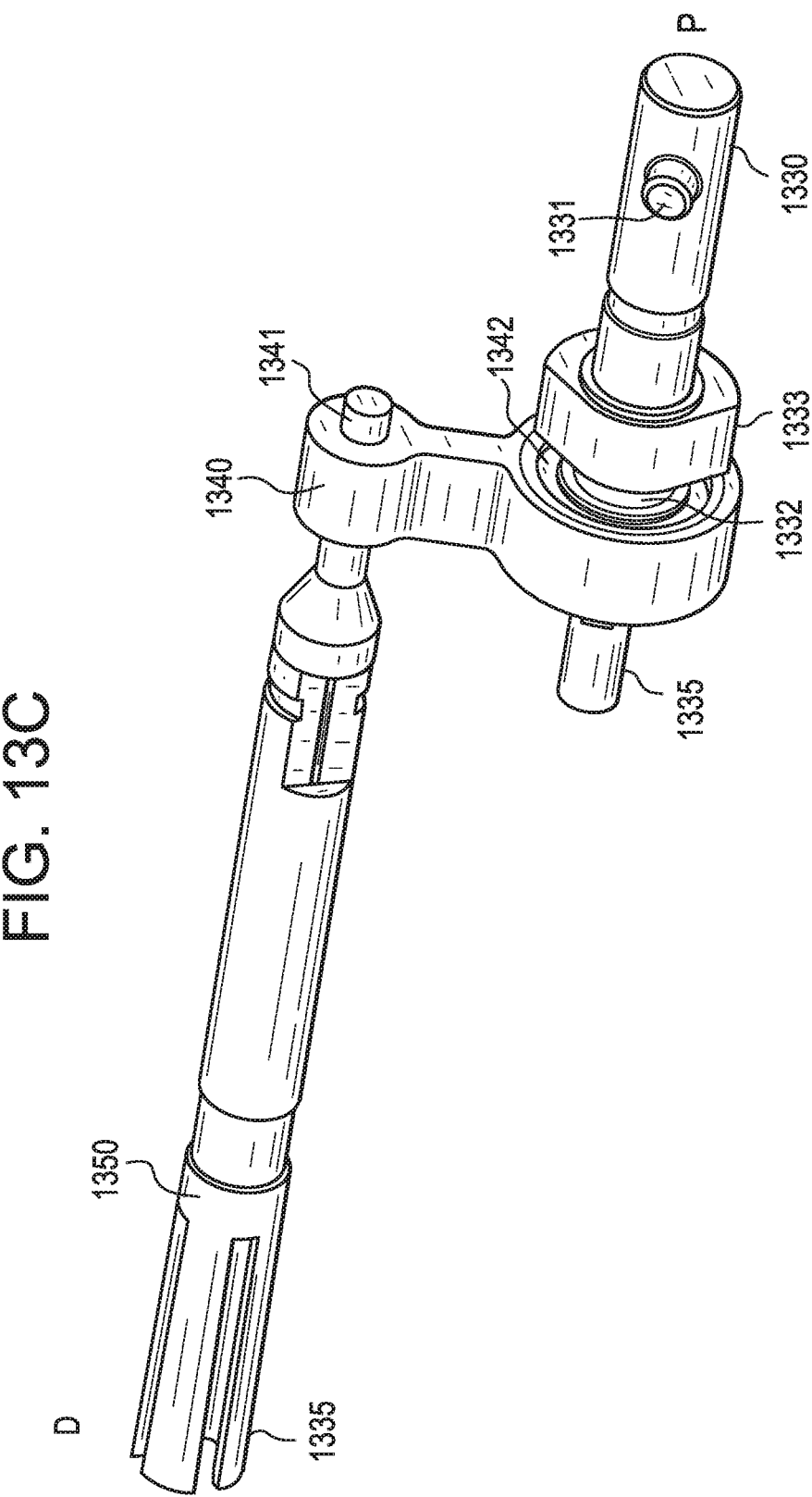

FIGS. 13B and 13C show the moving components of the four-bar linkage oscillator drive assembly 1300 without the housing 1301, bearings 1339, bushings 1302, 1303, or retainer 1304. In operation, the output shaft 1350 oscillates as the central axis of the eccentric section 1332 moves close to and then away from the central axis of the output shaft 1350. The linkage 1340 is connected to the eccentric section 1332 by a bearing 1342, bushing, or direct contact to the eccentric section 1332 at one end and to an offset pin 1341 coupled to the output shaft 1350 at an opposite end of the linkage 1340 by a bearing, bushing, or direct contact. In some embodiments, the offset pin 1341 is part of the linkage 1340 and travels inside a bearing, bushing, or direct contact offset from the central axis of the output shaft 1350.

FIGS. 13D-13F show the motion of the four bar linkage oscillator 1310 as it converts the clockwise rotational motion of the input shaft 1330 (arrows 1390) to oscillating motion of the output shaft 1350 (arrows 1394, 1396). In FIGS. 13D-13F, the intersections of the first horizontal (H1) axis with the vertical (V) axis (as noted above, horizontal and vertical are relative terms depending on an orientation of the device) represent the central axis of rotation B of the input shaft 1330, and the intersections of the second horizontal axis (H2) with the vertical (V) axis represent the central axis of rotation C of the output shaft 1350. In FIG. 13D, the eccentric section 1332 is minimally extended in the vertical direction away from the output shaft 1350 (in other words, the central axis A of the eccentric section 1332 is rotated to a position where it is disposed a maximum distance away from the output shaft 1350), which represents a near maximum oscillation of the output shaft 1350 in the counterclockwise direction (as indicated by arrow 1394). This oscillation is represented by an angular deviation of a reference line 1398 through the center of output shaft 1350 that is chosen such that the reference line 1398 aligns with the vertical axis V between the maximum and minimum oscillation points, as shown in FIG. 13E. As FIG. 13D represents the near maximum counterclockwise oscillation of the output shaft 1350, continued clockwise rotation 1390 of the input shaft 1330 eventually moves the eccentric section 1332 vertically towards the output shaft 1350, which rotates the offset pin 1341 and the output shaft 1350 clockwise about the central axis C of the output shaft 1350, as shown in FIG. 13E.

FIG. 13E represent about 90 degrees of clockwise rotation 1390 of the eccentric section 1332 from the position of FIG. 13D. Continued rotation of the input shaft 1330 rotates the eccentric section to a near maximum vertical position, as shown in FIG. 13F, where a central axis A of the eccentric shaft 1332 is closest to the output shaft 1350 and the linkage 1340 has been driven upwards (in the plane of FIG. 13F). This motion of the linkage 1340 can rotate the input shaft 1350 clockwise to a maximum oscillation in the clockwise direction (as indicated by arrow 1396). Continued rotation of the input shaft 1330 rotates the eccentric shaft 1332 to move the linkage 1340 away from the output shaft 1350 and induces counterclockwise rotation in the output shaft 1350. Therefore, as the input shaft 1330 spins, the output shaft 1350 oscillates between the positions shown in FIGS. 13D and 13F. The ratios between the distances between the pivot points can change the amplitude of this oscillation (e.g., changing the offset distance between the central axis of the input shaft 1330 and eccentric section 1332, the length of the linkage 1340, the offset of the pin 1341, etc.).

The four bar linkage oscillator can also provide advantages over known oscillators. For example, in comparison to a traditional Scotch yoke the four bar linkage oscillator lacks a bearing that slaps between sides of a yoke, which can fatigue the yoke and radially impact a bearing on the offset shaft. Thus, in traditional Scotch yoke, as the RPM/OPM increases the likelihood for fatigue of the yoke and bearing wear on the offset shaft increases. The four bar linkage oscillator, in contrast, has only rotational bearing surfaces that remain in contact at all times, allowing for improved durability and more predictable wear. In some embodiments, the linkage 1340 can be made of a bearing grade material, thereby negating the need for a separate bearing between the linkage 1340 and either of the offset pin 1341 and/or the eccentric section 1332 of the input shaft 1330.

In comparison to the piston oscillator described above, the four bar linkage can in some embodiments be configured to provide a greater angular range of oscillation, but may not be capable of operating at the very high speeds achievable with the piston oscillator. For example, in some embodiments the range of angular oscillation for the four bar linkage oscillator can be up to about 40°. In the illustrated embodiment, the range of angular oscillation can be about 31°.

In some embodiments, the output shaft 1250 or 1350 or blade shaft 310 can also be forced to oscillate axially about their axis of rotation in order to improve debris clearing during the cutting operation. This axial motion can be created through use of a cam mechanism to drive the output shaft 1250 or 1350 or blade shaft 310 proximally and distally during the course of a single stroke.

Alternative Configurations

Figure 14:
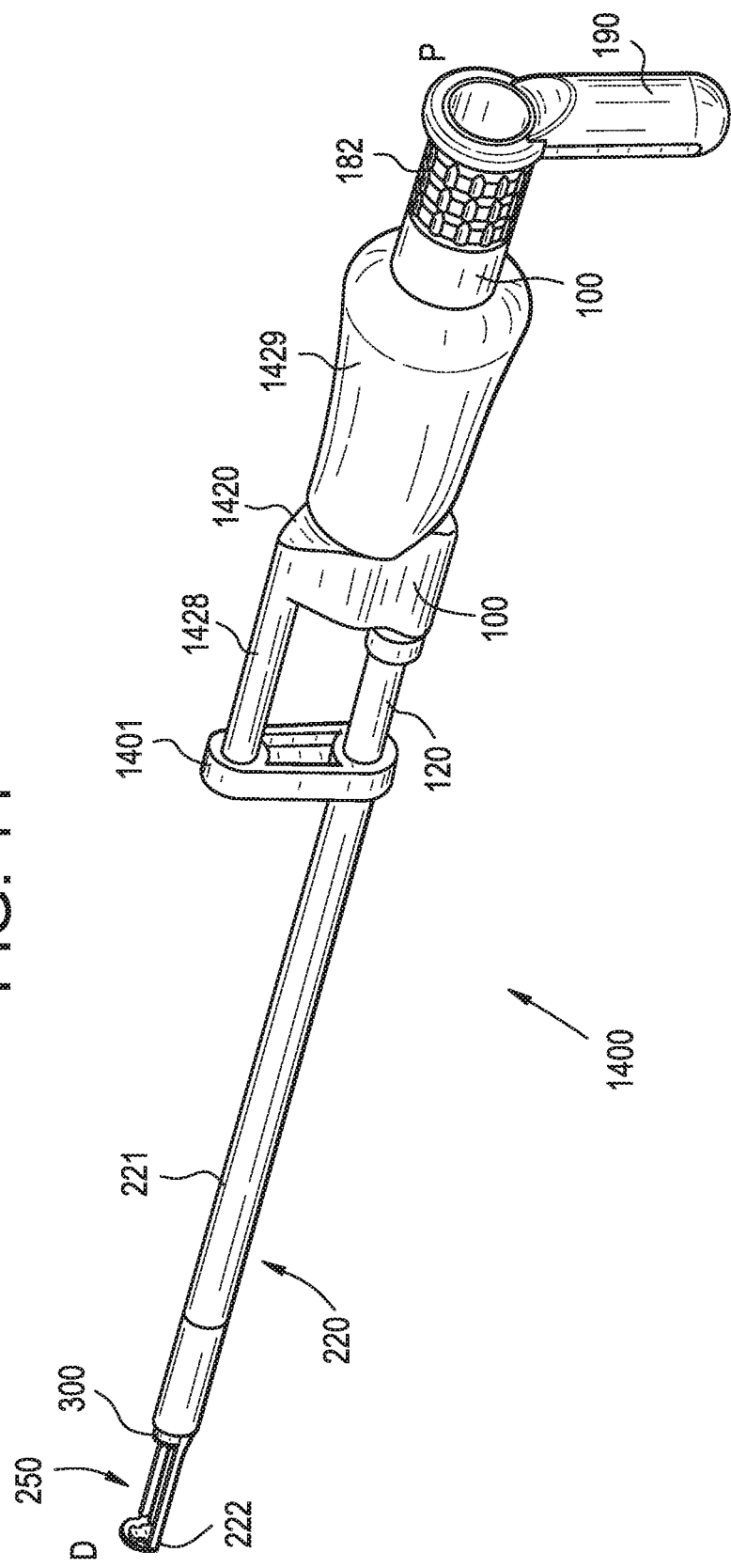
FIG. 14 is an illustration of one embodiment of a bone and tissue resection device having an alternative axial grip arrangement that is integral to the oscillator.

FIG. 14 is an illustration of one embodiment of a bone and tissue resection device having an alternative longitudinally extending grip arrangement. FIG. 14 shows the bone and tissue resection device 1400 includes a drive assembly 100 and a stationary frame 1420 around the drive assembly 100 and a disposable shield assembly 220 temporarily attached to the stationary frame 1420. The stationary frame 1420 includes an attachment beam 1428 for connecting a coupling element 1401 of the shield assembly 220 and preventing rotation of the shield assembly 220 with respect to the stationary frame 1420. The coupling element 1401 includes a clip feature at one end thereof that engages with the attachment beam 1428 by being rotated around the shield assembly 220. The stationary frame 1420 has a grip 1429 disposed around the stationary frame 1420 and shaped to allow a user to grasp the stationary frame 1420 in their hand, with their thumb resting against the thumb trigger 190 of the drive assembly 100. In some embodiments, the stationary frame 1420 is connected to the oscillator assembly 100 and cannot be removed from the oscillator assembly 100. In some embodiments, the stationary frame 1420 can be separated from the oscillator assembly 100 allowing the user to handle the oscillator assembly 100 directly. In some embodiments, a spring can be used to retract the blade 300 inside of the disposable shield assembly 220.

Figure 15:
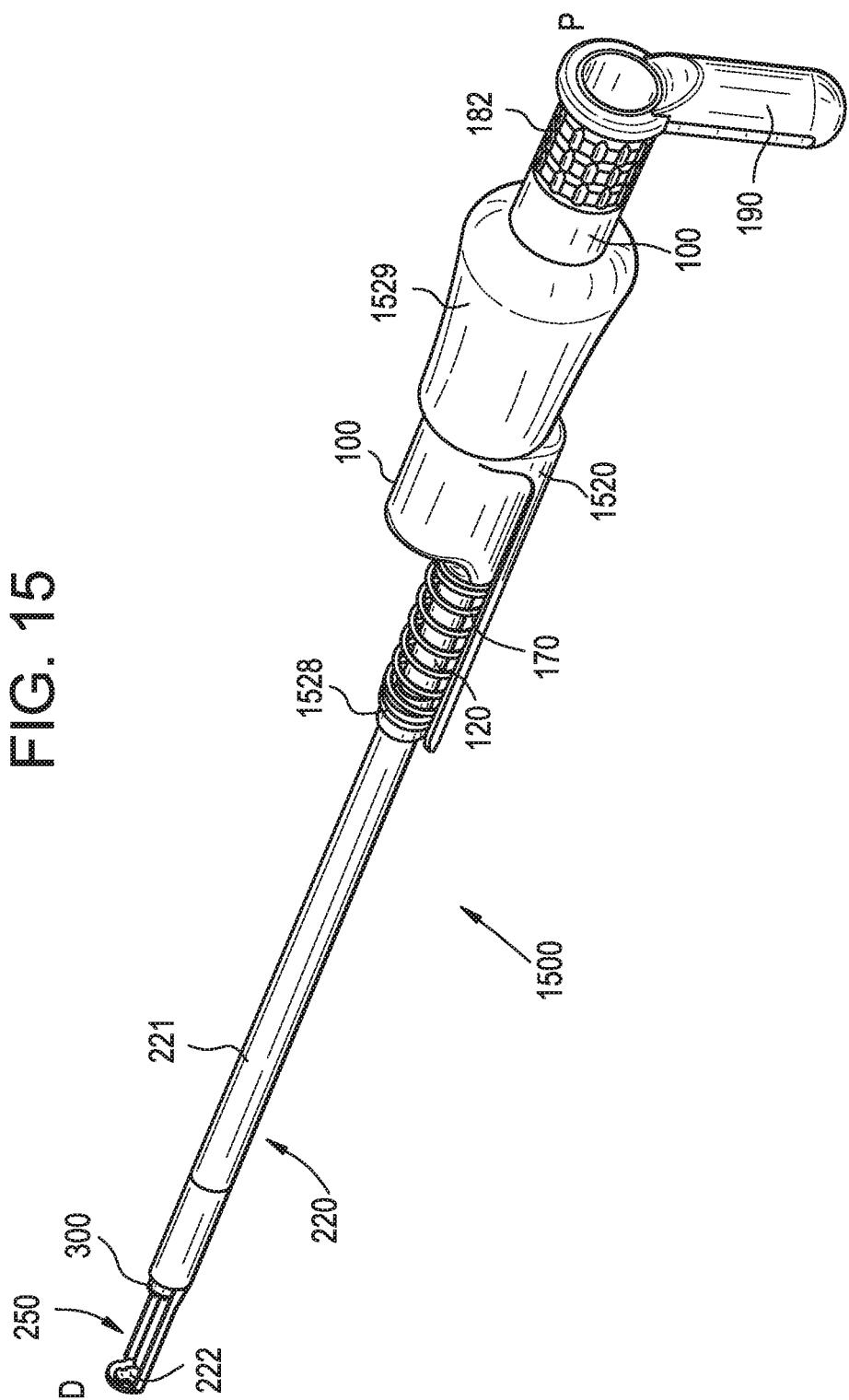
FIG. 15 is an illustration of one embodiment of a bone and tissue resection device having yet another alternative axial grip arrangement that is detachable from the oscillator.

FIG. 15 is an illustration of a bone and tissue resection device having yet another alternative longitudinally extending grip arrangement. The bone and tissue resection device 1500 includes a drive assembly 100 and a stationary frame 1520 around the drive assembly 100 and a disposable shield assembly 220 attached to the stationary frame 1520. The stationary frame 1420 includes a coupling 1528 for connecting the shield assembly 220. In some embodiments, the shield assembly 220 is integral to the stationary frame 1520. The stationary frame 1520 has a grip 1529 disposed around the stationary frame 1520 and shaped to allow a user to grasp the stationary frame 1520 in their hand, with their thumb resting against the thumb trigger 190 of the drive assembly 100. The stationary frame 1520 includes a spring 270 that biases the drive assembly 100 in the proximal direction and against, for example, the user's force against the thumb trigger 190 to move the drive assembly 100 in the distal direction and translate the blade 300 through the cutting region 250 at the distal end of the shield assembly 220.

Figure 16:
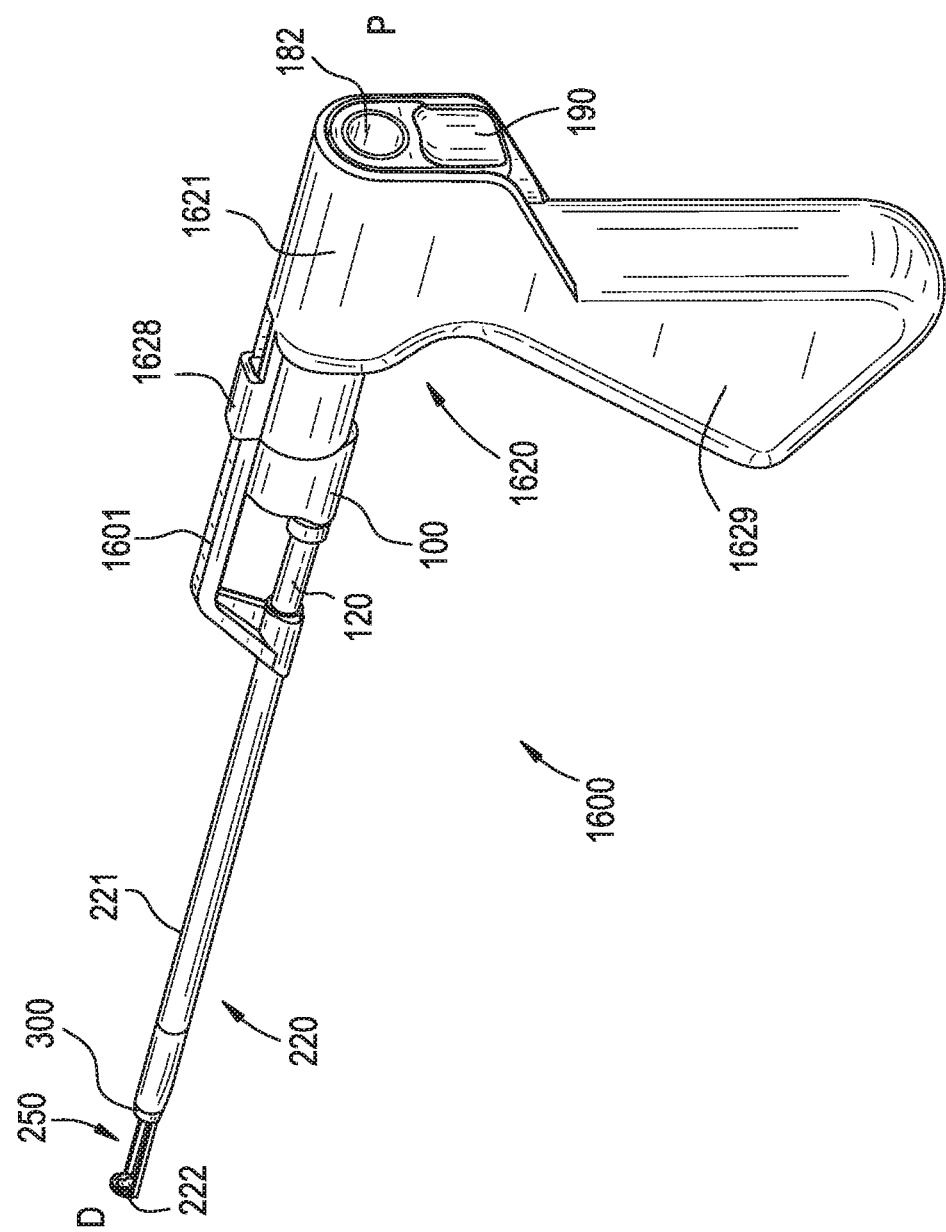
FIG. 16 is an illustration of one embodiment of a bone and tissue resection device having a thumb-actuated trigger.

FIG. 16 is an illustration of a bone and tissue resection device having a thumb-actuated trigger. The bone and tissue resection device 1600 includes a stationary assembly 1620 and a drive assembly 100 slidably engaged directly or indirectly with a frame 1621 of the stationary assembly 1620. A shield assembly 220 is attached to the stationary assembly with an offset elongated arm 1601 that engages with a coupler 1628 on the frame 1621 to retain the shield assembly 220 in place. The elongated arm 1601 extends radially from the shield assembly to increase the ability of the coupler 1628 to prevent rotation of the elongated tube 221 of the shield assembly if any rotational energy is transferred to the footplate 222 during use. In some embodiments, a spring can be used to retract the blade 300 inside of the disposable shield assembly 220.

The frame 1621 of the stationary assembly includes an integrated handle 1629 shaped to be grasped by a user's hand, with their thumb against the thumb trigger 190 of the drive assembly 100 to actuate the movement of the drive assembly 100 with respect to the frame 1621. In some embodiments the shape fills the palm to enable the user to guide the footplate 222 with their hand but leaves the thumb free to advance the oscillator assembly 100. Here, the frame 1621 surrounds the thumb trigger 190 such depressing the thumb trigger distally to move the drive assembly 100 advances the thumb trigger 190 toward the stationary assembly 1620. In some embodiments, the thumb trigger 190 being recessed into the frame 1621 can further secure the position of the user's thumb against the thumb trigger 190 and prevent a user's finger from being pinched or trapped between the trigger 190 and the stationary housing 1620. In some embodiments, the bone and tissue resection device 1600 can include a powered actuation mechanism to move the drive assembly 100, and the thumb trigger 190 can be a button that the user engages to control the powered actuation mechanism to move the drive assembly 100 distally or proximally. In some embodiments, the powered actuation mechanism can move the drive assembly 100 proximally when the thumb trigger 190 is released.

In some embodiments the feature a user presses to advance the blade 300 towards the footplate 222 to cut can activate the motor that causes the oscillator assembly 100 to oscillate.

Coring Saw Device Examples

FIGS. 17A and 17B are illustrations of a bone and tissue resection device 1700 having a rotating coring saw blade 1731. A continuously spinning coring saw can be nested inside a housing with an opening to allow the blade to be exposed to the tissue to be cut. FIG. 17A shows a shield sleeve 1721 fixedly attached to a handle 1791 and a drive assembly 1710 slidably attached to the handle 1791. The drive assembly 1710 can be configured to be coupled with a motor 20 and a coring blade 1731. The drive assembly 1710 can include a thumb trigger 1790 for pushing the drive assembly 1710 distally using the thumb of a user's hand that is holding the handle 1791. The shield sleeve 1721 can include an open distal end 1722 and one or more cutting region(s) 250 through which the coring blade 1731 passes as it is driven distally by the drive assembly being advanced with respect to the shield sleeve 1721. FIG. 17B shows the bone and tissue resection device 1700 with the blade 1731 attached. While shown with an open distal end 1722, in some embodiments the shield sleeve 1721 can have a closed end. In some embodiments, the shield sleeve 1721 can be detached from the handle to allow for a variety of shield options to be used. In some embodiments, the drive assembly 1710 can be advanced through means of a manual squeeze style trigger or automated through use of an actuator to drive the motion forward and backward. In some embodiments, the drive assembly 1710 can have a spring to return the blade 1731 to the starting position.

Counter-Rotating Blade Examples

Figure 18:
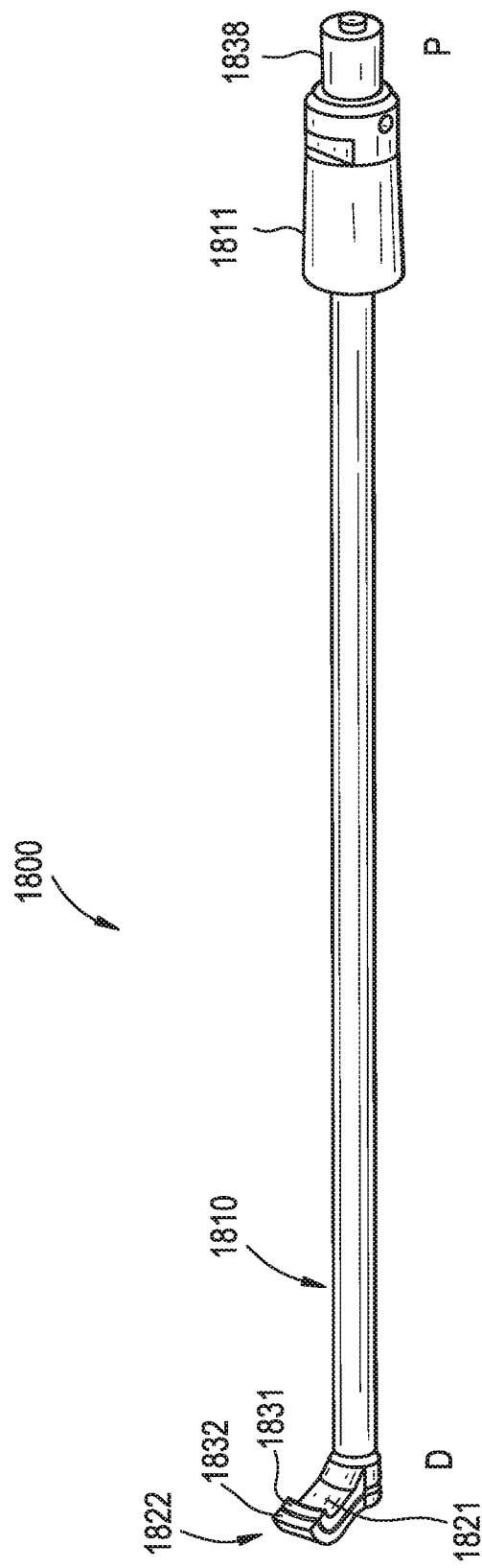
FIG. 18 is an illustration of one embodiment of a counter-rotating blade device for use with an oscillating drive assembly.

FIG. 18 is an illustration of a counter-rotating blade device 1800 for use with an oscillating drive assembly, such as the drive assembly 100 of FIG. 1. FIG. 18 shows the counter-rotating blade device 1800 includes a distal end with dual counter rotating blades 1821, 1822 with either toothed or diamond grit ends 1831, 1832. The counter-rotating blade device 1800 includes a coupling mechanism 1938 at a proximal end for coupling the counter-rotating blade device 1800 with the output of an oscillating drive assembly. In operation, counter rotation stabilizes the blades 1821, 1822 to ensure maximum cutting efficiency. In some embodiments, the counter rotation of the blades 1821, 1822 can be driven through use of a planetary gear mechanism 1811 attached to the coupling mechanism 1838. In some embodiments, the counter rotation of the blades 1821, 1822 can be driven through two separate oscillating mechanisms.

Alternative Depth Adjustment Mechanism Arrangements

FIGS. 19A and 19B are illustrations of one embodiment of a bone and tissue resection device 1900 with a depth adjustment mechanism 1901 for adjusting the position of a blade 300 by translating a drive assembly 100. The bone and tissue resection device 1900 includes a stationary assembly 200 with a shield assembly 220 extending to a cutting region 250 proximal to a footplate 420 at the distal end of the shield assembly 220. The bone and tissue resection device 1900 also includes a drive assembly 100 configured to move with respect to the stationary assembly 200, the drive assembly 100 including a blade shaft 310 extending distally from the drive assembly 100 to a blade 300 through a blade shaft shield 120. The depth adjustment mechanism 1901 is configured to move the drive assembly 100 along a proximal-distal axis of the bone and tissue resection device 1900, whereby the movement of the drive assembly 100 causes the blade 300 to move through the cutting region 250 at the distal end of the shield assembly 220. FIG. 19A shows the bone and tissue resection device 1900 with the drive assembly 100 in a proximal position with the blade 300 retracted from the cutting region 250. In FIG. 19B, the depth adjustment mechanism 1901 has moved the drive assembly 1901 distally until the blade 300 has crossed the entire cutting region 250.

FIGS. 20A and 20B are illustrations of one embodiment of a bone and tissue resection device 2000 with a depth adjustment mechanism 2001 is configured to adjust the axial position of the blade 300 with respect to the cutting region 250 without adjusting the axial position of the drive mechanism 100. The depth adjustment mechanism 2001 is configured to move the blade 300 and blade shaft 310 with respect to the drive assembly 100 along a proximal-distal axis of the bone and tissue resection device 3000, whereby the depth adjustment mechanism 2001 causes the blade 300 to move into and out of the cutting region 250 at the distal end of the shield assembly 220. FIG. 20A shows the bone and tissue resection device 2000 with the blade 300 and blade shaft 310 in a proximal position with the blade 300 retracted from the cutting region 250. In FIG. 20B, the depth adjustment mechanism 2001 has moved the blade 300 distally until the blade 300 has crossed the entire cutting region 250.

FIGS. 21A and 21B are illustrations of one embodiment of a bone and tissue resection device 2100 with a depth adjustment mechanism 2102 that includes handle 2101 configured to be operated by a user to apply a force to advance a blade 300 through a cutting region 250. In operation, as shown in FIG. 22A, the depth adjustment mechanism 2102 can, for example pivot about a point 2103 in the bone and tissue resection device 2100 such that the force applied to the handle 2101 by the user in a servers to rotate the handle 2101 about the pivot point 2103, as shown by arrow 2104. In rotation, the handle 2101 drive the depth adjustment mechanism 2102 distally against the drive assembly 100, which moves the blade 300 through the cutting region 250, as shown in FIG. 22B. In other embodiments, the drive assembly 100 is stationary depth adjustment mechanism 2102 is configured to drive the blade 300 through the cutting region 250 and the blade 300 and the blade shaft 310 move with respect to the drive assembly 100.

FIGS. 22A and 22B are illustrations of one embodiment of a bone and tissue resection device 2200 with a powered depth adjustment mechanism 2201 operable to adjust the position of a blade 300 with respect to a cutting region 250. The bone and tissue resection device 2200 includes a trigger 2202 configured to be operable by a user holding the bone and tissue resection device 2200. The trigger 2202 is configured to send a signal via a control wire 2203 to the depth adjustment mechanism 2201. FIG. 22A shows the depth adjustment mechanism 2201 is coupled to the drive assembly 100 in order to move the drive assembly 100 along a proximal-distal axis and thereby move the blade 300 into and out of the cutting region 250. In some embodiments, the depth adjustment mechanism 2201 can move the drive assembly 100 distally when a user engages the trigger 2202 and then move the drive mechanism 100 proximally when the user releases the trigger 2202. In other embodiments, the trigger 2202 can be configured to be operable in more than one direction, such that the user can actively control both the distal and proximal movement of the blade 300 in the cutting region 250. In some embodiments, the depth adjustment mechanism 2201 includes an electric motor. In some embodiments, the drive assembly 100 is not driven by the depth adjustment mechanism 2201, and instead the depth adjustment mechanism 2201 moves the blade 300 with respect to the drive assembly 100.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The instruments disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the instruments disclosed herein can have varying degrees of rigidity or flexibility, as appropriate for their use. Device sizes can also vary greatly, depending on the intended use and surgical site anatomy. Furthermore, particular components can be formed from a different material than other components. One or more components or portions of the instrument can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context of spinal surgery on a human patient, it will be appreciated that the methods and devices disclosed herein can be used in any of a variety of surgical procedures with any human or animal subject, or in non-surgical procedures.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc.

One skilled in the art will appreciate further features and advantages of the disclosure based on the above-described embodiments. Accordingly, the disclosure is not to be limited by what has been particularly shown and described. All publications and references cited herein are expressly incorporated herein by reference in their entirety.

What is claimed is:

1. A bone and tissue resection device, comprising:
    a blade having a distal cutting edge configured to perform a cutting action that produces a plug or core from a media being cut by the cutting edge;
    a drive mechanism arranged to transfer an oscillating force to the cutting edge for oscillating the cutting edge the drive mechanism comprising:
        an input shaft configured to continuously rotate about a first central axis, a portion of a length of the input shaft defining an eccentric section, the eccentric section defining a second central axis that is offset from the first central axis,
        a linkage disposed around the eccentric section at a first end thereof and having a second end, and
        an oscillating shaft defining a central axis thereof, the oscillating shaft coupled to the second end of the linkage at a location offset from the central axis of the oscillating shaft, wherein continuous rotation of the input shaft about the first central axis creates an oscillating rotational movement of the oscillating shaft about the central axis of the oscillating shaft;
    a shield positioned to block contact with a portion of the cutting edge; and
    a depth adjustment mechanism configured to translate the cutting edge along a proximal-distal axis of the shield to adjust an axial position of the cutting edge relative to the shield.

2. The bone and tissue resection device of claim 1, wherein the drive mechanism is configured to produce an oscillating axial motion of the cutting edge along a proximal-distal axis of the cutting edge.

3. The bone and tissue resection device of claim 2, wherein the drive mechanism comprises a cam mechanism configured to produce the oscillating axial motion of the cutting edge.

4. The device of claim 2, wherein the drive mechanism comprises a piezoelectric mechanism configured to produce the oscillating axial motion of the cutting edge.

5. The bone and tissue resection device of claim 1, wherein the oscillating force causes oscillation of the cutting edge around a proximal-distal axis of the cutting edge.

6. The bone and tissue resection device of claim 1, wherein the oscillating force causes oscillation of the cutting edge around a proximal-distal axis of the cutting edge, and wherein the drive mechanism is configured to produce an oscillating axial motion of the cutting edge along the proximal-distal axis of the cutting edge while the cutting edge oscillates around the proximal-distal axis of the cutting edge.

7. The bone and tissue resection device of claim 1, wherein the cutting edge defines a crescentic shape such that the plug or core of the media being cut can be extracted through an open side of the blade.

8. The bone and tissue resection device of claim 1, wherein the cutting edge defines a shape matching an implant, such that the plug or core cut from a media clears a path for implantation of the implant in the media.

9. The bone and tissue resection device of claim 1, wherein the shield comprises a closed distal end configured to prevent contact with the cutting edge.

10. The bone and tissue resection device of claim 1, wherein the shield comprises an open distal end configured to enable the blade to be inserted from the distal end into the drive mechanism.

11. The bone and tissue resection device of claim 1, wherein the shield defines one or more openings located radially from the cutting edge to expose the cutting edge.

12. The bone and tissue resection device of claim 1, wherein the cutting edge defines a crescent shape and the blade defines and concave surface and a convex surface opposite the concave surface, and wherein the shield defines an opening radial to the convex surface of the blade and closed region radial to the concave surface, wherein the opening of the shield enables a user to view the blade and the closed region contains media resected by the cutting edge.

13. The bone and tissue resection device of claim 1, wherein the cutting edge defines a crescent shape and the blade defines a concave surface and a convex surface opposite the concave surface, and wherein the shield defines a first opening radial to the convex surface of the blade and a second opening radial to the concave surface of the blade, and wherein the shield defines one or more posts separating the two openings, the one or more posts extending to a distal end of the shield.

14. The bone and tissue resection device of claim 13, wherein the shield comprises a protrusion extending towards the concave surface of the blade for extracting material from the concave surface of the blade when the blade is translated in a proximal direction by the depth adjustment mechanism after being driven distally to cut the material.

15. The bone and tissue resection device of claim 1, wherein the depth adjustment mechanism is configured to adjust the axial position of the cutting edge with respect to the shield without adjusting the axial position of the drive mechanism with respect to the shield.

16. The device of claim 1, wherein the depth adjustment mechanism is configured to adjust the position of the cutting edge by translating the drive mechanism along the proximal-distal axis of the shield.

17. The bone and tissue resection device of claim 1, comprising a handle, and wherein the depth adjustment mechanism is configured to be operated by a user via the handle, wherein, when a user applies a force to the handle, the depth adjustment mechanism transfers the force from the handle to the blade to adjust the position of the cutting edge.

18. The bone and tissue resection device of claim 1, wherein the depth adjustment mechanism comprises a powered mechanism operable by a user to adjust the position of the cutting edge relative to the shield.

19. The bone and tissue resection device of claim 1, wherein the drive mechanism comprises:
the linkage having a lumen formed in the second end thereof that is parallel to and offset from the second central axis; and
a pin disposed within the lumen of the linkage;
wherein the oscillating shaft is coupled to and offset from the pin such that the oscillating shaft is coupled to linkage via the pin.

20. The bone and tissue resection device of claim 19, wherein the blade is coupled to the oscillating shaft.

21. The bone and tissue resection device of claim 19, wherein the input shaft further comprises a counter weight configured to balance rotation of the eccentric section about the first central axis.

22. The bone and tissue resection device of claim 19, further comprising a bearing disposed around the input shaft.

23. The bone and tissue resection device of claim 19, further comprising a bearing disposed around the oscillating shaft.

24. The bone and tissue resection device of claim 19, further comprising a collet formed at a distal end of the oscillating shaft, the collet including a plurality of arms extending distally around a central axis of the oscillating shaft.

25. The bone and tissue resection device of claim 1, wherein the shield is configured to detect nerves within a path of the cutting edge using EMG or MMG.

26. The bone and tissue resection device of claim 1, wherein the shield is able to be navigated to enable alignment of a cut area of the cutting edge.

27. A bone and tissue resection device, comprising:
a blade having a distal cutting edge configured to perform a cutting action that produces a plug or core from a media being cut by the cutting edge;
a drive mechanism arranged to transfer an oscillating force to the cutting edge for oscillating the cutting edge the drive mechanism comprising:
an input shaft configured to continuously rotate about a first central axis, a portion of a length of the input shaft defining an eccentric section, the eccentric section defining a second central axis that is offset from the first central axis,
a linkage disposed around the eccentric section at a first end thereof and having a second end, and
an oscillating shaft defining a central axis thereof, the oscillating shaft coupled to the second end of the linkage at a location offset from the central axis of the oscillating shaft, wherein continuous rotation of the input shaft about the first central axis creates an oscillating rotational movement of the oscillating shaft about the central axis of the oscillating shaft;
a shield positioned to block contact with a portion of the cutting edge; and
a depth adjustment mechanism configured to translate the cutting edge along a proximal-distal axis of the shield to adjust an axial position of the cutting edge relative to the shield.

28. A bone and tissue resection device, comprising:
a blade having a distal cutting edge configured to perform a cutting action that produces a plug or core from a media being cut by the cutting edge;
a drive mechanism arranged to transfer an oscillating force to the cutting edge for oscillating the cutting edge;
a shield positioned to block contact with a portion of the cutting edge; and
a depth adjustment mechanism configured to translate the cutting edge along a proximal-distal axis of the shield to adjust an axial position of the cutting edge relative to the shield
wherein the cutting edge defines a crescent shape and the blade defines a concave surface and a convex surface opposite the concave surface, and wherein the shield defines a first opening radial to the convex surface of the blade and a second opening radial to the concave surface of the blade, and wherein the shield defines one or more posts separating the two openings, the one or more posts extending to a distal end of the shield.

29. The bone and tissue resection device of claim 28, wherein the shield comprises a protrusion extending towards the concave surface of the blade for extracting material from the concave surface of the blade when the blade is translated in a proximal direction by the depth adjustment mechanism after being driven distally to cut the material.

\* \* \* \* \*